US 11,845,985 B2

United States Patent
Salk et al.

(10) Patent No.: US 11,845,985 B2
(45) Date of Patent: *Dec. 19, 2023

(54) METHODS AND REAGENTS FOR CHARACTERIZING GENOMIC EDITING, CLONAL EXPANSION, AND ASSOCIATED APPLICATIONS

(71) Applicant: TwinStrand Biosciences, Inc., Seattle, WA (US)

(72) Inventors: Jesse J. Salk, Seattle, WA (US); Charles Clinton Valentine, III, Seattle, WA (US)

(73) Assignee: TwinStrand Biosciences, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/741,183

(22) Filed: May 10, 2022

(65) Prior Publication Data

US 2023/0002820 A1     Jan. 5, 2023

Related U.S. Application Data

(63) Continuation of application No. 17/259,501, filed as application No. PCT/US2019/041735 on Jul. 12, 2019.

(60) Provisional application No. 62/697,397, filed on Jul. 12, 2018.

(51) Int. Cl.
*C12Q 1/6869* (2018.01)
*G16B 30/10* (2019.01)
*G16B 20/20* (2019.01)

(52) U.S. Cl.
CPC ........... *C12Q 1/6869* (2013.01); *G16B 20/20* (2019.02); *G16B 30/10* (2019.02)

(58) Field of Classification Search
CPC ............... C12Q 1/6869; C12Q 1/6855; C12Q 2525/191; C12Q 2535/119; G16B 30/10; G16B 20/20

See application file for complete search history.

(56) References Cited

U.S. PATENT DOCUMENTS

| | | | |
|---|---|---|---|
| 5,308,751 A | 5/1994 | Ohkawa et al. |
| 5,589,337 A | 12/1996 | Farr |
| 6,251,610 B1 | 6/2001 | Gupte et al. |
| 6,498,023 B1 | 12/2002 | Abarzua |
| 6,582,908 B2 | 6/2003 | Fodor et al. |
| 6,958,225 B2 | 10/2005 | Dong |
| 7,214,490 B2 | 5/2007 | Su et al. |
| 7,267,966 B2 | 9/2007 | Dong et al. |
| 7,297,778 B2 | 11/2007 | Matsuzaki et al. |
| 7,406,385 B2 | 7/2008 | Sorenson |
| 7,452,699 B2 | 11/2008 | Makrigiorgos |
| 7,459,273 B2 | 12/2008 | Jones et al. |
| 7,476,503 B2 | 1/2009 | Turner et al. |
| 7,741,463 B2 | 6/2010 | Gormley et al. |
| 8,029,993 B2 | 10/2011 | Mikawa |
| 8,148,068 B2 | 4/2012 | Brenner |
| 8,153,375 B2 | 4/2012 | Travers et al. |
| 8,318,434 B2 | 11/2012 | Cuppens |
| 8,715,967 B2 | 5/2014 | Casbon et al. |
| 8,741,606 B2 | 6/2014 | Casbon et al. |
| 9,080,210 B2 | 7/2015 | Van et al. |
| 9,085,798 B2 | 7/2015 | Chee |
| 9,249,460 B2 | 2/2016 | Pushkarev et al. |
| 9,260,753 B2 | 2/2016 | Xie et al. |
| 9,476,095 B2 | 10/2016 | Vogelstein et al. |
| 9,598,731 B2 | 3/2017 | Talasaz |
| 9,745,627 B2 | 8/2017 | Van et al. |
| 9,752,188 B2 | 9/2017 | Schmitt et al. |
| 9,783,847 B2 | 10/2017 | Chee |
| 9,834,822 B2 | 12/2017 | Talasaz |
| 9,862,995 B2 | 1/2018 | Patel |
| 9,898,577 B2 | 2/2018 | Van Eijk et al. |
| 9,920,366 B2 | 3/2018 | Eltoukhy et al. |
| 10,000,800 B2 | 6/2018 | Chee |
| 10,011,871 B2 | 7/2018 | Bielas |
| 10,023,907 B2 | 7/2018 | Van et al. |
| 10,119,165 B2 | 11/2018 | Chee |
| 10,202,646 B2 | 2/2019 | Fodor et al. |
| 10,266,883 B2 | 4/2019 | Chee |
| 10,266,884 B2 | 4/2019 | Chee |
| 10,287,630 B2 | 5/2019 | Xie et al. |
| 10,287,631 B2 | 5/2019 | Salk et al. |

(Continued)

FOREIGN PATENT DOCUMENTS

| | | |
|---|---|---|
| CN | 102877136 B | 3/2014 |
| CN | 106367485 A | 2/2017 |

(Continued)

OTHER PUBLICATIONS

Boyd, D.S., et al., "Measurement and clinical monitoring of human lymphocyte clonality by massively parallel VDJ pyrosequencing," Science Translational Medicine 1(12): 12ra23, 16 pages, American Association for the Advancement of Science, United States (Dec. 2009).

(Continued)

*Primary Examiner* — David C Thomas
(74) *Attorney, Agent, or Firm* — STERNE, KESSLER, GOLDSTEIN & FOX P.L.L.C.

(57) ABSTRACT

Methods for characterizing genome editing, clonal expansion and associated reagents for use in such methods are disclosed herein. Some embodiments of the technology are directed to characterizing a population of cells following an engineered genomic editing event, that includes in some embodiments characterizing genomic alterations occurring at both intended and unintended genomic loci within the genome of the populations of cells. Other embodiments are directed to utilizing Duplex Sequencing for assessing a clonal selection in mixed cell populations and/or cell populations following a genomic editing event. Further examples of the present technology are directed to methods for detecting and assessing clonal expansion of cells following a genomic editing event.

26 Claims, 10 Drawing Sheets

(56) References Cited

U.S. PATENT DOCUMENTS

| | | |
|---|---|---|
| 10,370,713 B2 | 8/2019 | Salk et al. |
| 10,385,393 B2 | 8/2019 | Salk et al. |
| 10,501,793 B2 | 12/2019 | Chee |
| 10,570,451 B2 | 2/2020 | Salk et al. |
| 10,689,700 B2 | 6/2020 | Salk et al. |
| 10,711,304 B2 | 7/2020 | Salk et al. |
| 10,752,951 B2 | 8/2020 | Salk et al. |
| 10,760,127 B2 | 9/2020 | Salk et al. |
| 10,844,428 B2 | 11/2020 | Gnerre et al. |
| 10,870,882 B2 | 12/2020 | Otwinowski et al. |
| 11,118,225 B2 | 9/2021 | Salk et al. |
| 11,198,907 B2 | 12/2021 | Salk et al. |
| 11,242,562 B2 | 2/2022 | Salk et al. |
| 2003/0165923 A1 | 9/2003 | Li et al. |
| 2004/0209299 A1 | 10/2004 | Pinter et al. |
| 2005/0100900 A1 | 5/2005 | Kawashima et al. |
| 2007/0020640 A1 | 1/2007 | McCloskey et al. |
| 2007/0128624 A1 | 6/2007 | Gormley et al. |
| 2007/0172839 A1 | 7/2007 | Smith et al. |
| 2007/0172873 A1 | 7/2007 | Brenner et al. |
| 2008/0167195 A1 | 7/2008 | Li et al. |
| 2008/0261204 A1 | 10/2008 | Lexow |
| 2009/0298075 A1 | 12/2009 | Travers et al. |
| 2010/0069263 A1 | 3/2010 | Shendure et al. |
| 2010/0222238 A1 | 9/2010 | Smith et al. |
| 2010/0331204 A1 | 12/2010 | Jeddeloh et al. |
| 2011/0160078 A1 | 6/2011 | Fodor et al. |
| 2011/0301042 A1 | 12/2011 | Steinmann et al. |
| 2012/0058468 A1 | 3/2012 | McKeown |
| 2012/0071331 A1 | 3/2012 | Casbon et al. |
| 2012/0094847 A1 | 4/2012 | Warthmann et al. |
| 2012/0165202 A1 | 6/2012 | Porreca et al. |
| 2012/0208724 A1 | 8/2012 | Steemers et al. |
| 2012/0220494 A1 | 8/2012 | Samuels et al. |
| 2012/0238738 A1 | 9/2012 | Hendrickson |
| 2012/0244125 A1 | 9/2012 | Hendrickson |
| 2012/0322666 A1 | 12/2012 | Pham et al. |
| 2013/0079231 A1 | 3/2013 | Pushkarev et al. |
| 2013/0303461 A1 | 11/2013 | Iafrate et al. |
| 2014/0030704 A1 | 1/2014 | Mikawa |
| 2014/0057799 A1 | 2/2014 | Johnson et al. |
| 2014/0134610 A1 | 5/2014 | Pham et al. |
| 2014/0155274 A1 | 6/2014 | Xie et al. |
| 2014/0329282 A1 | 11/2014 | Nelson et al. |
| 2014/0329698 A1 | 11/2014 | Bignell et al. |
| 2015/0024950 A1 | 1/2015 | Bielas et al. |
| 2015/0044687 A1 | 2/2015 | Schmitt et al. |
| 2015/0119261 A1 | 4/2015 | Richard |
| 2015/0197786 A1 | 7/2015 | Osborne et al. |
| 2015/0275289 A1 | 10/2015 | Otwinowski et al. |
| 2015/0284803 A1 | 10/2015 | Lindley |
| 2016/0026758 A1 | 1/2016 | Jabara et al. |
| 2016/0046986 A1 | 2/2016 | Eltoukhy et al. |
| 2016/0130649 A1 | 5/2016 | Xie et al. |
| 2016/0153039 A1 | 6/2016 | Amorese et al. |
| 2016/0319345 A1 | 11/2016 | Gnerre et al. |
| 2016/0362751 A1 | 12/2016 | Shin et al. |
| 2017/0107560 A1 | 4/2017 | Peter et al. |
| 2017/0136433 A1 | 5/2017 | Sun et al. |
| 2017/0211140 A1 | 7/2017 | Schmitt et al. |
| 2017/0247687 A1 | 8/2017 | Shendure et al. |
| 2017/0253925 A1 | 9/2017 | Dobosy et al. |
| 2017/0260583 A1 | 9/2017 | Dobosy et al. |
| 2018/0023135 A1 | 1/2018 | Van Eijk et al. |
| 2018/0291438 A1 | 10/2018 | Jamshidi et al. |
| 2018/0363048 A1 | 12/2018 | Bielas |
| 2018/0363049 A1 | 12/2018 | Bielas |
| 2018/0363051 A1 | 12/2018 | Schmitt et al. |
| 2018/0363052 A1 | 12/2018 | Schmitt et al. |
| 2018/0363053 A1 | 12/2018 | Schmitt et al. |
| 2019/0093160 A1 | 3/2019 | Schmitt et al. |
| 2019/0093161 A1 | 3/2019 | Schmitt et al. |
| 2019/0093162 A1 | 3/2019 | Schmitt et al. |
| 2019/0119748 A1 | 4/2019 | Schmitt et al. |
| 2019/0119749 A1 | 4/2019 | Schmitt et al. |
| 2019/0271040 A1 | 9/2019 | Salk et al. |
| 2019/0284626 A1 | 9/2019 | Salk et al. |
| 2019/0284627 A1 | 9/2019 | Salk et al. |
| 2019/0292597 A1 | 9/2019 | Salk et al. |
| 2019/0323082 A1 | 10/2019 | Salk et al. |
| 2019/0338358 A1 | 11/2019 | Salk et al. |
| 2019/0352714 A1 | 11/2019 | Salk et al. |
| 2020/0040378 A1* | 2/2020 | Beatty .................. C12Q 1/6806 |
| 2020/0048701 A1 | 2/2020 | Chee |
| 2020/0048702 A1 | 2/2020 | Chee |
| 2020/0048703 A1 | 2/2020 | Chee |
| 2020/0131561 A1 | 4/2020 | Kennedy et al. |
| 2020/0318185 A1 | 10/2020 | Salk et al. |
| 2020/0362390 A1 | 11/2020 | Salk et al. |
| 2020/0392580 A1 | 12/2020 | Salk et al. |
| 2021/0002711 A1 | 1/2021 | Otwinowski et al. |
| 2021/0010065 A1 | 1/2021 | Salk et al. |
| 2021/0207210 A1 | 7/2021 | Otwinowski et al. |
| 2021/0269873 A1 | 9/2021 | Salk et al. |
| 2021/0277461 A1 | 9/2021 | Glezer et al. |
| 2021/0292836 A1 | 9/2021 | Salk et al. |
| 2021/0324470 A1 | 10/2021 | Salk et al. |
| 2021/0355532 A1 | 11/2021 | Salk et al. |
| 2021/0371920 A1 | 12/2021 | Salk et al. |
| 2021/0371921 A1 | 12/2021 | Salk et al. |
| 2021/0371922 A1 | 12/2021 | Salk et al. |
| 2021/0371923 A1 | 12/2021 | Salk et al. |
| 2021/0371924 A1 | 12/2021 | Salk et al. |
| 2021/0381048 A1 | 12/2021 | Salk et al. |
| 2022/0010376 A1 | 1/2022 | Salk et al. |
| 2022/0017961 A1 | 1/2022 | Salk et al. |
| 2022/0195523 A1 | 6/2022 | Salk et al. |

FOREIGN PATENT DOCUMENTS

| | | |
|---|---|---|
| GB | 2533882 B | 10/2016 |
| WO | WO-2006113422 A2 | 10/2006 |
| WO | WO-2010112821 A1 | 10/2010 |
| WO | WO-2010148115 A1 | 12/2010 |
| WO | WO-2011021102 A2 | 2/2011 |
| WO | WO-2012042374 A2 | 4/2012 |
| WO | WO-2012061832 A1 | 5/2012 |
| WO | WO-2012129363 A2 | 9/2012 |
| WO | WO-2012142213 A2 | 10/2012 |
| WO | WO-2013123442 A1 | 8/2013 |
| WO | WO-2013142389 A1 | 9/2013 |
| WO | WO-2013181170 A1 | 12/2013 |
| WO | WO-2014142850 A1 | 9/2014 |
| WO | WO-2015075056 A1 | 5/2015 |
| WO | WO-2015100427 A1 | 7/2015 |
| WO | WO-2015175040 A1 | 8/2015 |
| WO | WO-2016040901 A1 | 3/2016 |
| WO | WO-2017037656 A1 | 3/2017 |
| WO | WO-2017079428 A1 | 5/2017 |
| WO | WO-2017100441 A1 | 6/2017 |
| WO | WO-2018013598 A1 | 1/2018 |
| WO | WO-2018031588 A1 | 2/2018 |
| WO | WO-2018175997 A1 | 9/2018 |
| WO | WO-2019094651 A1 | 5/2019 |
| WO | WO-2019160998 A1 | 8/2019 |
| WO | WO-2019200228 A1 | 10/2019 |
| WO | WO-2020014693 A1 | 1/2020 |

OTHER PUBLICATIONS

Haapaniemi , E., et al., "CRISPR-Cas9 genome editing induces a p53-mediated DNA damage response," Nature Medicine 24(7):927-930, Nature Publishing Group, United Kingdom (Jul. 2018).

Ihry, R.J., et al., "p53 inhibits CRISPR-Cas9 engineering in human pluripotent stem cells," Nature Medicine 24(7):939-946, Nature Publishing Group, United Kingdom (Jul. 2018).

International Search Report and Written Opinion for International Application No. PCT/US2019/041735, Alexandria, VA, dated Oct. 16, 2019, 11 pages.

(56) References Cited

OTHER PUBLICATIONS

Kennedy, S.R., et al., "Ultra-sensitive sequencing reveals an age-related increase in somatic mitochondrial mutations that are inconsistent with oxidative damage," PLoS Genetics 9(9):e1003794, Public Library of Science, United States (2013).

Kennedy, S.R., et al., "Detecting ultralow-frequency mutations by Duplex Sequencing," Nature Protocols 9(11):2586-2606, Nature Publishing Group, United Kingdom (Nov. 2014).

Saitoh, A., et al., "Most tumors in transgenic mice with human c-Ha-ras gene contained somatically activated transgenes," Oncogene 5(8):1195-200, Nature Publishing Group, United Kingdom (Aug. 1990).

Salk, J.J., et al., "Passenger mutations as a marker of clonal cell lineages in emerging neoplasia," Seminars in Cancer Biology 20(5):294-303, Academic Press Inc., United States (Oct. 2010).

Schmitt, M.W., et al., "Detection of ultra-rare mutations by next-generation sequencing," Proc Natl Acad Sci USA 109(36):14508-14513, National Academy of Sciences, United States (Sep. 2012).

Schmitt, M.W., et al., "Sequencing small genomic targets with high efficiency and extreme accuracy," Nature Methods 12(5):423-425, Nature Publishing Group, United Kingdom (May 2015).

Ahn, E.H., et al., "Decreased Mitochondrial Mutagenesis during Transformation of Human Breast Stem Cells into Tumorigenic Cells," Cancer Research, 76(15):4569-4578, American Association of Cancer Research, United States (Aug. 2016).

Akogwu, I., et al., "A Comparative Study of K-Spectrum-Based Error Correction Methods for Next-Generation Sequencing Data Analysis Human Genomics," Human Genomics, 2(20):50-59, BioMed Central, United Kingdom (Jul. 2016).

Ameur, A., et al., "Ultra-Deep Sequencing of Mouse Mitochondrial DNA: Mutational Patterns and Their Origins," PLoS Genetics 7(3):e1002028, Public Library of Science, United States (Mar. 2011).

Bainbridge, N.M., et al., "Whole Exome Capture in Solution With 3 Gbp of Data," Genome Biology 11(6): R62, BioMed Central Ltd, United Kingdom (2010).

Bentley, R.D., et al., "Accurate Whole Human Genome Sequencing Using Reversible Terminator Chemistry," Nature, 456(7218):53-59, Nature Publishing Group, United Kingdom (Nov. 2008).

Besaratinia, A., et al., "A High-throughput Next-Generation Sequencing-based Method for Detecting the Mutational Fingerprint of Carcinogens," Nucleic Acids Research 40(15):e116, Oxford University Press, United Kingdom (Aug. 2012).

Bielas, H.J., et al., et al., "Quantification of Random Genomic Mutations," Nature Methods 2(4):285-290, Nature Publishing Group, United States (Apr. 2005).

Borodina, T., et al., "A Strand-Specific Library Preparation Protocol for RNA Sequencing," Methods in Enzymology, 500:79-98, Academic Press, United States (2011).

Campbell, J.P., et al., "Subclonal Phylogenetic Structures in Cancer Revealed by Ultra-Deep Sequencing," Proc Natl Acad Sci USA 2;105(35):13081-13086, National Academy of Sciences, United States (Aug. 2008).

Carlson, C.A., "Decoding Cell Lineage From Acquired Mutations Using Arbitrary Deep Sequencing," Nature Methods ,9:78-80, Nature Publication Group, United States (2012).

Casbon, A.J., et al., "A Method for Counting PCR Template Molecules With Application to Next-Generation Sequencing," Nucleic Acids Research 39(12):e81, Oxford University Press, United Kingdom (Jul. 2011).

Cervantes, B.R., et al., "Embryonic Stem Cells and Somatic Cells Differ in Mutation Frequency and Type," Proc Natl Acad Sci USA 19;99(6):3586-3590, National Academy of Sciences United States (Mar. 2002).

Chen, L., et al., "DNA Damage Is a Pervasive Cause of Sequencing Errors, Directly Confounding Variant Identification," Science, 355(6326):752-756, American Association for the Advancement of Science, United States (Feb. 2017).

Chiu, K.W.R., et al., "Non-Invasive Prenatal Diagnosis of Fetal Chromosomal Aneuploidy by Massively Parallel Genomic Sequencing of DNA in Maternal Plasma," Proceedings of the National Academy of Sciences of the United States of Americ, 23;105(51):20458-20463, National Academy of Sciences, United States (Dec. 2008).

Chiu, K.W.R., et al., "Non-Invasive Prenatal Assessment of Trisomy 21 by Multiplexed Maternal Plasma DNA Sequencing: Large Scale Validity Study," BMJ (Clinical research ed.) 11;342:c7401, British Medical Association, United Kingdom (Jan. 2011).

Clark, A.T., et al., " Direct Detection and Sequencing of Damaged DNA Bases," Genome Integrity, 20;2:10, Medknow, United Kingdom (Dec. 2010).

De Grassi, A., et al., "Ultradeep Sequencing of a Human Ultraconserved Region Reveals Somatic and Constitutional Genomic Instability," PLoS Biology 8(1):e1000275, Public Library of Science, United States (Jan. 2010).

Diehl, F., et al., "Detection and Quantification of Mutations in the Plasma of Patients With Colorectal Tumors," Proc Natl Acad Sci USA 8;102(45):16368-71633, National Academy of Sciences, United States (Nov. 2005).

Diehl, F., et al., "Analysis of Mutations in DNA Isolated From Plasma and Stool of Colorectal Cancer Patients," Gastroenterology 135(2):489-498, W.B. Saunders, Baltimore (Aug. 2008).

Ding, L., et al., "Analysis of Next-Generation Genomic Data in Cancer: Accomplishments and Challenges," Human Molecular Genetics 15;19(R2):R188-R196, IRL Press at Oxford University Press, United Kingdom (Oct. 2010.

Ding, L., et al., "Clonal Evolution in Relapsed Acute Myeloid Leukaemia Revealed by Whole-Genome Sequencing," Nature 481;(7382):506-510, Nature Publishing Group, United Kingdom (Jan. 2012).

Druley, E.T., et al., "Quantification of Rare Allelic Variants From Pooled Genomic DNA," Nature Methods 6(4):263-265, Nature Publication Group, United States (Apr. 2009).

Ehrich, M., et al., "Noninvasive Detection of Fetal Trisomy 21 by Sequencing of DNA in Maternal Blood: A Study in a Clinical Setting," American Journal of Obstetrics and Gynecology 204(3):205.e1-11, Elsevier, United States (Mar. 2011).

Ewing, B., Green, P., et al., "Base-calling of Automated Sequencer Traces Using Phred. Ii. Error Probabilities," Genome Research 8(3):186-194, Cold Spring Harbor Laboratory Press, United States (Mar. 1998).

Fan, C.H., et al., "Noninvasive Diagnosis of Fetal Aneuploidy by Shotgun Sequencing DNA From Maternal Blood, "Proc Natl Acad Sci USA 21;105(42):16266-16271, National Academy of Sciences, United States (Oct. 2008).

Flaherty, P., et al., "Ultrasensitive Detection of Rare Mutations Using Next-Generation Targeted Resequencing," Nucleic Acids Research 40(1):e2, Oxford University Press, United Kingdom (Jan. 2012).

Fleischhacker, M and Schmidt, B., Circulating Nucleic Acids (CNAs) and Cancer—a Survey, Biochimica Et Biophysica Acta 1775(1):181-232, Elsevier Pub. Co, Netherlands (Jan. 2007).

Fong, L.S., et al., "Comparison of 7 Methods for Extracting Cell-Free DNA From Serum Samples of Colorectal Cancer Patients," Clinical Chemistry 55(3):587-589, Oxford University Press, United Kingdom ( Mar. 2009).

Fordyce, L.S., et al., "High-throughput Sequencing of Core Str Loci for Forensic Genetic Investigations Using the Roche Genome Sequencer Flx Platform," BioTechniques 51(2):127-133, Future Science, United Kingdom (Aug. 2011).

Forshew, T., et al., "Noninvasive Identification and Monitoring of Cancer Mutations by Targeted Deep Sequencing of Plasma DNA," Science Translational Medicine 30;4(136):136ra68, American Association for the Advancement of Science, United States (May 2012).

Fu, K.G., et al., "Counting Individual DNA Molecules by the Stochastic Attachment of Diverse Labels," Proceedings of the National Academy of Sciences 108(22):9026-9031, National Academy of Sciences, United States (May 2011).

Garcia-Garcerà, M., et al., "Fragmentation of Contaminant and Endogenous DNA in Ancient Samples Determined by Shotgun Sequencing; Prospects for Human Palaeogenomics," Plos One 6(8):e24161, Public Library of Science, United States (2011).

(56) References Cited

OTHER PUBLICATIONS

Goodwin, S., et al., "Coming of Age: Ten Years of Next-Generation Sequencing Technologies," Nature Reviews. Genetics, 17(6):333-351, Nature Publishing Group, United Kingdom (May 2016).
Gordon, J.D., et al., "Causes and Consequences of Aneuploidy in Cancer," Nature Reviews 24;13(3):189-203, Nature Pub. Group, United Kingdom (Jan. 2012).
Greaves, C.L., et al., "Quantification of Mitochondrial DNA Mutation Load," Aging Cell 8(5):566-572, Blackwell Pub, United Kingdom (Sep. 2009).
Haag-Liautard, H.C., et al., "Direct Estimation of the Mitochondrial DNA Mutation Rate in Drosophila Melanogaster," PLoS Biology 19;6(8):e204, Public Library of Science, United States (Aug. 2008).
Havens, J., "The technology and clinical applications of hybrid capture," NGSMedical Laboratory Observer retrieved from: https://www.mlo-online.com/home/article/13008809/the-technology-and-clinical-applications-of-hybrid-capture-ngs, published Jul. 2016, 5 pages.
He, Y., et al., "Heteroplasmic Mitochondrial DNA Mutations in Normal and Tumour Cells," Nature 25;464(7288):610-614, Nature Publishing Group, United Kingdom (Mar. 2010).
Hiatt, J.B., et al., "Single Molecule Molecular Inversion Probes for Targeted, High-Accuracy Detection of Low-Frequency Variation," Genome Research, 23(5):843-854, Cold Spring Harbor Laboratory Press, United States (May 2013).
Hodgkinson, A., et al., "Variation in the Mutation Rate Across Mammalian Genomes," Nature Reviews 4;12(11):756-766, Nature Publication Group, United Kingdom (Oct. 2011).
Howell, N., et al., "How Rapidly Does the Human Mitochondrial Genome Evolve?," American Journal of Human Genetics 59(3):501-509, American Society of Human Genetics, United States (Sep. 1996).
Hyman, W.R., et al., "The Dynamics of the Vaginal Microbiome During Infertility Therapy With in Vitro Fertilization-Embryo Transfer," Journal of Assisted Reproduction and Genetics 29(2): 105-115, Springer, Netherlands (Feb. 2012).
International Search Report and Written Opinion for PCT/US2018/024194 dated Jul. 7, 2018. 10 pages.
Jabara, B.C., et al., "Accurate Sampling and Deep Sequencing of the HIV-1 Protease Gene Using a Primer Id," Proc Natl Acad Sci USA 13;108(50):20166-20171, National Academy of Sciences, United States (Dec. 2011).
Jazin, E.E., et al., "Human Brain Contains High Levels of Heteroplasmy in the Noncoding Regions of Mitochondrial DNA," Proc Natl Acad Sci USA 29;93(22):12382-123827, National Academy of Sciences, United States (Oct. 1996).
Jiang, H., et al., "Seqmap: Mapping Massive Amount of Oligonucleotides to the Genome," Bioinformatics 15;24(20):2395-2396, Oxford University Press, United Kingdom (Oct. 2008).
Jung, H., et al., "The DNA Integrity Number (DIN) Provided by the Genomic DNA Screen Tape Assay Allows for Streamlining of NGS of FFPE Tissue Samples Application Note Nucleic Acid Analysis," Agilent Technologies, 4 pages, Korea (Dec. 2015).
Kanagawa, T., " Bias and Artifacts in Multitemplate Polymerase Chain Reactions (Pcr)," Journal of Bioscience and Bioengineering 96(4):317-323, Society for Biotechnology, Japan (2003).
Kao, C.W., et al., "Bayescall: A Model-based Base-Calling Algorithm for High-throughput Short-Read Sequencing," Genome Research 19(10):1884-1895, Cold Spring Harbor Laboratory Press, United States (Oct. 2009).
Kasai, H., et al., "Formation, Inhibition of Formation, and Repair of Oxidative 8-hydroxyguanine DNA Damage," Basic Life Sciences 61:257-262, Plenum Press, United States (1993).
Kaur, M., and Makrigiorgos, M.G., "Novel Amplification of DNA in a Hairpin Structure: Towards a Radical Elimination of PCR Errors From Amplified DNA," Nucleic Acids Research 15;31(6):e26, Oxford University Press, United Kingdom (Mar. 2013).
Kebschull, J.M and Zador, A.M., "Sources of PCR-Induced Distortions in High-throughput Sequencing Data Sets," Nucleic Acids Research, 43(21):e143, Oxford University Press, United Kingdom (Dec. 2015).
Kennedy, R.S., et al., "Somatic Mutations in Aging, Cancer and Neurodegeneration," Mechanisms of Ageing and Development, 133(4):118-126, Elsevier Science Ireland, Ireland (Apr. 2012).
Khaidakov, M., et al., "Accumulation of Point Mutations in Mitochondrial DNA of Aging Mice," Mutation Research 15;526(1-2):1-7, Elsevier, Netherlands (May 2003).
Kinde, I., et al., "Detection and Quantification of Rare Mutations With Massively Parallel Sequencing," Proc Natl Acad Sci USA, 108(23):9530-9535, National Academy of Sciences, United States (Jun. 2011).
Kircher, M., et al., "Improved Base Calling for the Illumina Genome Analyzer Using Machine Learning Strategie," Genome Biologys 10(8):R83, BioMed Central Ltd, United Kingdom (2009).
Kirsch, S., and Klein, A.C., "Sequence Error Storms and the Landscape of Mutations in Cancer," Proc Natl Acad Sci USA 4;109(36):14289-14290, National Academy of Sciences, United States (Sep. 2012).
Kivioja, T., et al., "Counting Absolute Numbers of Molecules Using Unique Molecular Identifiers," Nature Methods 20;9(1):72-74, Nature Publication Group, United States (Nov. 2011).
Kozarewa, I., et al., Amplification-Free Illumina Sequencing-Library Preparation Facilitates Improved Mapping and Assembly of (G+c)-biased Genomes, Nature Methods 6(4):291-295, Nature Pub. Group, United States (Apr. 2009).
Kraytsberg, Y., et al., "Single Molecule PCR in MtDNA Mutational Analysis: Genuine Mutations Vs. Damage Bypass-derived Artifacts," Methods 46(4):269-273, Academic Press, United States (Dec. 2008).
Krimmel, J.D., et al., "Ultra-Deep Sequencing Detects Ovarian Cancer Cells in Peritoneal Fluid and Reveals Somatic TP53 Mutations in Noncancerous Tissues," Proc Natl Acad Sci USA, 113(21):6005-6010, United States National Academy of the Sciences, United States (May 2016).
Kunkel, A.T., "Mutational Specificity of Depurination," Proc Natl Acad Sci USA 81(5):1494-1498, National Academy of Sciences, United States (Mar. 1984).
Latuga, S.M., et al., "Beyond Bacteria: A Study of the Enteric Microbial Consortium in Extremely Low Birth Weight Infants," PLoS One 6(12):e27858, Public Library of Science, United States (2011).
Lecroq, B., et al., "Ultra-Deep Sequencing of Foraminiferal Microbarcodes Unveils Hidden Richness of Early Monothalamous Lineages in Deep-Sea Sediments,"Proc Natl Acad Sci USA 9;108(32):13177-13182, National Academy of Sciences, United States (Aug. 2011).
Ledergerber, C., and Dessimoz, C., "Base-Calling for Next-Generation Sequencing Platforms," Briefings in Bioinformatics 12(5):489-497, Stewart Publications, United Kingdom (Sep. 2011).
Li, H., et al., "Mapping Short DNA Sequencing Reads and Calling Variants Using Mapping Quality Scores," Genome Research 18(11):1851-1858, Cold Spring Harbor Laboratory Press, United States (Nov. 2008).
Li, H., and Durbin, R., "Fast and Accurate Short Read Alignment With Burrows-wheeler Transform," Bioinformatics, 15;25(14):1754-1760, Oxford University Press, United Kingdom (Jul. 2009).
Li, H., and Durbin, R., "Fast and Accurate Long-Read Alignment With Burrows-wheeler Transform," Bioinformatics, 26(5):589-595, Oxford University Press, United Kingdom (Mar. 2010).
Liang, C.K., et al., "Bayesian Basecalling for DNA Sequence Analysis Using Hidden Markov Models," IEEE/ACM Transactions on Computational Biology and Bioinformatics 4(3):430-440, IEEE Computer Society, United States (Sep. 2007).
Liao, W.J.G., et al. "Targeted Massively Parallel Sequencing of Maternal Plasma DNA Permits Efficient and Unbiased Detection of Fetal Alleles," Clinical Chemistry 57(1):92-101, Oxford University Press, United Kingdom (Jan. 2011).

(56) References Cited

OTHER PUBLICATIONS

Lin, T.M., et al., "High Aggregate Burden of Somatic MtDNA Point Mutations in Aging and Alzheimer's Disease Brain," Human Molecular Genetics 15;11(2):133-145, Press at Oxford University Press, United Kingdom (Jan. 2002).
Lindahl, T., Wood, D.R., "Quality Control by DNA Repair," Science 3;286(5446):1897-1905, American Association for the Advancement of Science, United States (Dec. 1999).
Lo, M.Y., et al., Quantitative Analysis of Fetal DNA in Maternal Plasma and Serum: Implications for Noninvasive Prenatal Diagnosis, American Journal of Human Genetics 62(4):768-775, Cell Press, United States (Apr. 1998).
Lou, D.I., et al., "High-Throughput DNA Sequencing Errors Are Reduced by Orders of Magnitude Using Circle Sequencing," Proc Natl Acad Sci USA, 110(49):19872-19877, National Academy of Sciences, United States (Dec. 2013).
Lunter, G and Goodson, M., "Stampy: A Statistical Algorithm for Sensitive and Fast Mapping of Illumina Sequence Reads," Genome Research 21(6):936-939, Cold Spring Harbor Laboratory Press, United States (Jun. 2011).
Lynch, M., "Rate, Molecular Spectrum, and Consequences of Human Mutation," Proc Natl Acad Sci USA 19;107(3):961-968, National Academy of Sciences, United States (Jan. 2010).
Lynch, M.A., et al., "New and Emerging Technologies for Genetic Toxicity Testing," Environmental and Molecular Mutagenesis, 52(3):205-223, Wiley-Liss, United States (Apr. 2011).
Mackelprang, R., et al., "Metagenomic Analysis of a Permafrost Microbial Community Reveals a Rapid Response to Thaw," Nature 6;480(7377):368-71, Nature Publishing Group, United Kingdom (Nov. 2011).
Makarova, K.S., "Annotation and Classification of CRISPR-Cas Systems," Methods in Molecular Biology, 1311:47-75, Humana Press, United States (2015).
McBride, J.T., et al., Mutagenic Spectrum Resulting From DNA Damage by Oxygen Radicals, Biochemistry 8;30(1):207-213, American Chemical Society, United States (Jan. 1991).
McCloskey, L.M., et al., "Encoding Pcr Products With Batchstamps and Barcodes," Biochemical Genetics 45(11-12):761-767, Kluwer Academic/Plenum Publishers, United States (Dec. 2007).
McKernan, J.K., et al., "Sequence and Structural Variation in a Human Genome Uncovered by Short-read, Massively Parallel Ligation Sequencing Using Two-base Encoding," Genome Research 19(9):1527-1541, Cold Spring Harbor Laboratory Press, United States (Sep. 2009).
Mertes, F., et al., "Targeted Enrichment of Genomic DNA Regions for Next-generation Sequencing," Briefings in Functional Genomics 10(6):374-386, Oxford University Press, United Kingdom (November 011).
Metzker, M.L., "Sequencing Technologies—The Next Generation," Nature Reviews: Genetics 11(1):31-46, Nature Pub. Group, United Kingdom (Jan. 2010).
Meyer, M., et al., "Targeted High-throughput Sequencing of Tagged Nucleic Acid Samples,"Nucleic Acids Research 35(15):e97, Oxford University Press, United Kingdom (2007).
Meyerhans, A., et al., "DNA Recombination During Pcr," Nucleic Acids Research 18(7):1687-1691,Oxford University Press, United Kingdom (Apr. 1990).
Meyerson, M., et al., "Advances in Understanding Cancer Genomes Through Second-generation Sequencing," Nature Reviews 11(10):685-696, Nature Pub. Group, United Kingdom (Oct. 2010).
Miner, B.E., et al., Molecular Barcodes Detect Redundancy and Contamination in Hairpin-Bisulfite PCR Nucleic Acids Research, 32(17):e135, Oxford University Press, United Kingdom (Sep. 2004).
Minot, S., et al., "The Human Gut Virome: Inter-Individual Variation and Dynamic Response to Diet," Genome Research, 21(10):1616-1625, Cold Spring Harbor Laboratory Press, United States (Oct. 2011).
Mitchell, P.S., et al., "Circulating Micrornas as Stable Blood-Based Markers for Cancer Detection," Proc Natl Acad Sci USA, 105(30):10513-10518, National Academy of Sciences, United States (Jul. 2008).
Nachmanson, D., et al., "Targeted Genome Fragmentation With Crispr/Cas9 Improves Hybridization Capture, Reduces PCR Bias, and Enables Efficient High-accuracy Sequencing of Small Targets," Genome Research, 28(10):1589-1599, Cold Spring Harbor Laboratory Press, United States (Oct. 2017).
Narayan, A., et al., "Ultrasensitive Measurement of Hotspot Mutations in Tumor DNA in Blood Using Error-suppressed Multiplexed Deep Sequencing," Cancer Research, 72(14):3492-3498, American Association for Cancer Research, United States (Jul. 2012).
Nasu, A., et al., " Genetic Heterogeneity of Hepatitis C Virus in Association With Antiviral Therapy Determined by Ultra-deep Sequencing," PloS One, 6(9):e24907, Public Library of Science, United States (2011).
Nielsen, R., et al., "Genotype and Snp Calling From Next-Generation Sequencing Data," Nature Reviews. Genetics, 12(6):443-451, Nature Publishing Group, United Kingdom (Jun. 2011).
Out, A.A., et al., "Deep Sequencing to Reveal New Variants in Pooled DNA Samples," Human Mutation, 30(12):1703-1712, Wiley-Liss, United States (Dec. 2009).
Ozsolak, F., et al., "Direct RNA Sequencing," Nature, 461(7265):814-818, Macmillan Publishers Limited, United States (Sep. 2009).
Park, G., et al., "Characterization of Background Noise in Capture-based Targeted Sequencing Data," Genome Biology, 18(136):1-13, Biomed Central Ltd, United Kingdom (Jul. 2017).
Parsons , T.J., et al., "A High Observed Substitution Rate in the Human Mitochondrial DNA Control Region," Nature Genetics, 15(4):363-368, Nature Publishing Co, United States (Apr. 1997).
Pecuchet, N., et al., "Analysis of Base-Position Error Rate of Next-Generation Sequencing to Detect Tumor Mutations in Circulating DNA," Clinical Chemistry, 62(11):1492-1503, Oxford University Press, United Kingdom (Nov. 2016).
Quail, M.A., et al., "A Large Genome Center's Improvements to the Illumina Sequencing System," Nature Methods, 5(12):1005-1010, Nature Publication Group, United States (Dec. 2008).
Quinlan, A.R., et al., "Pyrobayes: an Improved Base Caller for Snp Discovery in Pyrosequences," Nature Methods, 5(2):179-181, Nature Publication Group, United States (Jan. 2008).
Ran, F.A., et al., "Genome Engineering using the CRISPR-Cas9 System," Nature Protocols 8(11):2281-2308, Nature Pub. Group, United Kingdom (Nov. 2013).
Redon, R., et al., "Global Variation in Copy Number in the Human Genome," Nature, 444(7118):444-454, Nature Publishing Group, United Kingdom (Nov. 2006).
Rizzo, J.M and Buck, M.J., "Key Principles and Clinical Applications of "Next-Generation" DNA Sequencing," Cancer Prevention Research (Philadelphia, Pa.), 5(7):887-900, American Association for Cancer Research, United States (Jul. 2012).
Roberts, C.H., et al., "Short Template Amplicon and Multiplex Megaprimer-enabled Relay (Stammer) Sequencing, a Simultaneous Approach to Higher Throughput Sequence-based Typing of Polymorphic Genes," Immunogenetics, 62(4):253-260, Springer Verlag, United States (Apr. 2010).
Robinson, J.T., et al., "Integrative Genomics Viewer," Nature Biotechnology, 29(1):24-26, Nature America Publishing, United States (Jan. 2011).
Salk, J.J., et al., "Mutational Heterogeneity in Human Cancers: Origin and Consequences," Annual Review of Pathology, 5:51-75, Annual Reviews, United States (2010).
Salk, J. J., et al., "Enhancing the accuracy of next-generation sequencing for detecting rare and subclonal mutations," Nat Rev Genet 19(5):269-285, Nature Publishing Group, United Kingdom (May 2018).
Salk, J. J., and Kennedy, S. R., "Next-Generation Genotoxicology: Using Modern Sequencing Technologies to Assess Somatic Mutagenesis and Cancer Risk," Environ Mol Mutagen 61(1):135-151, Wiley Online Library, United States (published online Nov. 2019, published in print Jan. 2020).

(56) References Cited

OTHER PUBLICATIONS

Schwarzenbach, H., et al., "Cell-free Nucleic Acids as Biomarkers in Cancer Patients," Nature Reviews. Cancer 11(6):426-437, Nature Publishing Group, United Kingdom (2011).
Schweiger, M.R., et al., "Genome-wide Massively Parallel Sequencing of Formaldehyde Fixed-paraffin Embedded (FFPE) Tumor Tissues for Copy-number-and Mutation-analysis," PloS One, 4(5):e5548, Public Library of Science, United States (2009).
Sehnert, A.J., et al., "Optimal Detection of Fetal Chromosomal Abnormalities by Massively Parallel DNA Sequencing of Cell-free Fetal DNA From Maternal Blood," Clinical Chemistry, 57(7):1042-1049, Oxford University Press, United Kingdom (Jul. 2011).
Shen, Y., et al., "A Snp Discovery Method to Assess Variant Allele Probability From Next-generation Resequencing Data," Genome Research, 20(2):273-280, Cold Spring Harbor Laboratory Press, United States (Feb. 2010).
Shendure, J and Ji, H., "Next-Generation DNA Sequencing," Nature Biotechnology, 26(10):1135-1145, Nature America Publishing, United States (Oct. 2008).
Shibutani, S., et al., "Insertion of Specific Bases During DNA Synthesis Past the Oxidation-damaged Base 8-oxodg," Nature, 349(6308):431-434, Nature Publishing Group, United Kingdom (Jan. 1991).
Shin, G., et al., "CRISPR-Cas9-Targeted Fragmentation and Selective Sequencing Enable Massively Parallel Microsatellite Analysis," Nature Communications, 8:14291, Nature Publishing Group, United Kingdom (Feb. 2017).
Shiroguchi, K., et al., "Digital RNA Sequencing Minimizes Sequence-Dependent Bias and Amplification Noise With Optimized Single-molecule Barcodes," Proc Natl Acad Sci USA, 109(4):1347-1352, National Academy of Sciences, United States (Jan. 2012).
Song, S., et al., "DNA Precursor Asymmetries in Mammalian Tissue Mitochondria and Possible Contribution to Mutagenesis Through Reduced Replication Fidelity," Proc Natl Acad Sci USA 102(14):4990-4995, National Academy of Sciences, United States (Apr. 2005).
Sparks, A.B., et al., "Selective Analysis of Cell-free DNA in Maternal Blood for Evaluation of Fetal Trisomy," Prenatal Diagnosis, 32(1):3-9, New York, United Kingdom (Jan. 2012).
Stiller, M., et al., "Patterns of Nucleotide Misincorporations During Enzymatic Amplification and Direct Large-scale Sequencing of Ancient DNA," Proc Natl Acad Sci USA, 103(37):13578-13584, National Academy of Sciences, United States (Sep. 2006).
Stoneking, M., et al., "Hypervariable Sites in the MtDNA Control Region Are Mutational Hotspots," American Journal of Human Genetics, 67(4):1029-1032, Cell Press, United States (Oct. 2000).
Summerer, D., "Enabling technologies of genomic-scale sequence enrichment for targeted high-throughput sequencing," Genomics, 94(6):363-368, Academic Press, United States (Dec. 2009).
Supporting Information for Kinde, I., et al., "Detection and Quantification of Rare Mutations With Massively Parallel Sequencing," Proc Natl Acad Sci USA 108(23):9530-9535, National Academy of Sciences, United States, 10 pages (Jun. 2011). Accessed at URL:[https://www.pnas.org/doi/suppl/10.1073/pnas.1105422108/suppl_file/pnas.201105422si.pdf] on Mar. 10, 2022, 10 pages.
Supporting Information for Schmitt, M. W., et al., "Detection of ultra-rare mutations by next-generation sequencing," Proc Natl Acad Sci USA 109(36):14508-14513, National Academy of Science, United States (2012). Corrected Mar. 27, 2013. Accessed from URL:[https://www.pnas.org/doi/suppl/10.1073/pnas.1208715109/suppl_file/pnas.201208715si.pdf] on May 10, 2022, 3 pages.
Supporting Information for Shiroguchi, K., et al., "Digital RNA Sequencing Minimizes Sequence-Dependent Bias and Amplification Noise With Optimized Single-molecule Barcodes," Proc Natl Acad Sci USA109(4):1347-1352, National Academy of Sciences, United States (Jan. 2012). Accessed at URL:[https://www.pnas.org/doi/suppl/10.1073/pnas.1118018109/suppl_file/pnas.201118018si.pdf] on Mar. 10, 2022, 8 pages.

Teer, J. K., et al., "Systematic comparison of three genomic enrichment methods for massively parallel DNA sequencing," Genome Research, 20:1420-1431, Cold Spring Harbor Laboratory Press, United States (2010).
Thomas, D.C., et al., "Fidelity of Mammalian DNA Replication and Replicative DNA Polymerases,"Biochemistry, 30(51):11751-11759, American Chemical Society, United States (Dec. 1991).
Travers, K.J., et al., "A Flexible and Efficient Template Format for Circular Consensus Sequencing and SNP Detection," Nucleic Acids Research, 38(15):e159, Oxford University Press, United Kingdom (Aug. 2010).
Vandenbroucke, I., et al., "Minor Variant Detection in Amplicons Using 454 Massive Parallel Pyrosequencing: Experiences and Considerations for Successful Applications," Biotechniques, 51(3):167-177, Future Science, United Kingdom (Sep. 2011).
Vermulst, M., et al., "Mitochondrial Point Mutations Do Not Limit the Natural Lifespan of Mice," Nature Genetics, 39(4):540-543, Nature Publication Co, United States (Apr. 2007).
Wagle, N., et al., "High-throughput Detection of Actionable Genomic Alterations in Clinical Tumor Samples by Targeted, Massively Parallel Sequencing," Cancer Discovery, 2(1):82-93, American Association for Cancer Research, United States (Jan. 2012).
Wang, C., et al., "Characterization of Mutation Spectra With Ultra-Deep Pyrosequencing: Application to HIV-1 Drug Resistance," Genome Research, 17(8):1195-201, Cold Spring Harbor Laboratory Press, United States (Aug. 2007).
Wiemann, S., et al., "Simultaneous on-line DNA Sequencing on Both Strands With Two Fluorescent Dyes," Analytical Biochemistry, 224(1):117-121, Elsevier, United States (Jan. 1995).
Winters, M., et al., "Are We Fishing or Catching? Evaluating the Efficiency of Bait Capture of Codis Fragments," Forensic Science International. Genetics, 29:61-70, Elsevier, Netherlands (Jul. 2017).
Yang, J., et al., "Unbiased Parallel Detection of Viral Pathogens in Clinical Samples by Use of a Metagenomic Approach,"Journal of Clinical Microbiology, 49(10):3463-3469, American Society for Microbiology, United States (Oct. 2011).
Yuan, B., et al., "High-throughput Analysis of the Mutagenic and Cytotoxic Properties of DNA Lesions by Next-generation Sequencing," Nucleic Acids Research, 39(14):5945-5954, Oxford University Press, United Kingdom (Aug. 2011).
Zagordi, O., et al., "Error Correction of Next-Generation Sequencing Data and Reliable Estimation of HIV Quasispecies," Nucleic Acids Research, 38(21):7400-7409, Oxford University Press, United Kingdom (Nov. 2010).
Zheng, Z., et al., "Anchored Multiplex PCR for Targeted Next-Generation Sequencing," Nature Medicine, 20(12):1479-1484, Nature Publishing Company, United States (Dec. 2014).
Supplementary European Search Report for EP Application No. EP 19 83 4790, Munich, Germany, dated Mar. 18, 2022, 10 pages.
Revollo, J. R., et al., "Genome-wide mutation detection by interclonal genetic variation," Mutat Res Genet Toxicol Environ Mutagen 829-830:61-69, Elsevier, Netherlands (2018).
Verheijen, B. M., et al., "Somatic mutations in neurons during aging and neurodegeneration," Acta Neuropathol 135(6):811-826, Springer Science+Business Media, Germany (2018).
Craig, D.W., et al., "Identification of Genetic Variants Using Barcoded Multiplexed Sequencing," Nature 5(10):887-893, Nature Publishing Group, United Kingdom (Oct. 2008).
Evans, T. C., Jr., et al., "NEB Expressions," 8 pages, New England BioLabs, vol. 2.1, United States (Spring 2007) (IPR2022-00816 Ex. 1014).
Hartung, T., "Thresholds of Toxicological Concern—Setting a Threshold for Testing Below Which There is Little Concern," ALTEX 34(3):331-351, Spektrum Akademischer Verlag, Germany (Jan. 2017).
Hodges, E., et al., "Genome-wide in Situ Exon Capture for Selective Resequencing," Nature Genetics 39(12):1522-1527, Nature Publishing Group, United Kingdom (Dec. 2007).
Illumina, Inc., "Complete Secondary Analysis Workflow for the Genome Analyzer," Technical Note: Illumina® Systems and Software, 8 pages, Illumina, Inc., United States (Oct. 2009) (IPR2022-00816 Ex. 1011).

(56) References Cited

OTHER PUBLICATIONS

Illumina, Inc., "Preparing Samples for Sequencing Genomic DNA," 18 pages, Illumina, Inc., United States (2007) (IPR2022-00816 Ex. 1008).

Illumina, Inc., "TruSeq™ RNA and DNA Sample Preparation Kits," Data Sheet: Illumina® Sequencing, 4 pages, Illumina, Inc., United States (Nov. 2010) (IPR2022-00816 Ex. 1012).

International Search Report and Written Opinion for Application No. PCT/US2013/032665, ISA/US, Commissioner for Patents, Alexandria, Virginia, dated Jul. 9, 2013, 15 pages.

Mattox, A.K., et al., "Bisulfite-converted Duplexes for the Strand-specific Detection and Quantification of Rare Mutations," Proceedings of the National Academy of Sciences of the United States of America 114(18):4733-4738, National Academy of Sciences, United States (May 2017).

McCarthy, A., "Third Generation DNA Sequencing: Pacific Biosciences' Single Molecule Real Time Technology," Chemistry & Biology 17(7):675-676, Elsevier, United States (Jul. 2010).

Minoche, A.E., et al., "Evaluation of Genomic High-throughput Sequencing Data Generated on Illumina HiSeq and Genome Analyzer Systems," Genome Biology 12(11):R112, BioMed Central Ltd., United Kingdom (Nov. 2011).

New England BioLabs, "NEB Expressions," accessed at URL:[https://web.archive.org/web/20080321144426/http://https://web.archive.org/web/20080321144426/hreference/neb_transcripts.asp] on Feb. 23, 2022, 1 page, New England BioLabs Inc., United States (Feb. 23, 2022) (IPR2022-00816 Ex. 1015).

Nisha, K. and Deshwal, R.K., "Antioxidants and Their Protective Action Against DNA Damage," International Journal of Pharmacology and Pharmaceutical Sciences 3(Suppl. 4):28-32, Prime Publications, India (May 2011).

Perakis, S., et al., "Chapter 3: Advances in Circulating Tumor DNA Analysis," Advances in Clinical Chemistry 80:73-153, Elsevier, Netherlands (Jan. 2017).

Song, C. X., et al., "Sensitive and Specific Single-molecule Sequencing of 5-hydroxymethylcytosine," Nature Methods 9(1):75-77, Nature Publishing Group, United Kingdom (Nov. 2011).

\* cited by examiner

Human HRAS Exon 3

| Sample | Tissue | Treatment | Subtype | VD | Depth | Context | VAF |
|--------|--------|-----------|---------|-----|--------|---------|-------|
| F | Lung | Urethane | T>A | 300 | 16,425 | CTG | 1.82% |
| G | Lung | Urethane | T>A | 181 | 16,319 | CTG | 1.10% |
| H | Lung | Urethane | T>A | 58 | 13,692 | CTG | 0.42% |
| J | Lung | Urethane | T>A | 17 | 14,706 | CTG | 0.11% |

Amino acid: 65 | 64 | 63 | 62 | 61 | 60

Sequence: G C T G T A C T C C C T G G C C

FIG. 8A

METHODS AND REAGENTS FOR CHARACTERIZING GENOMIC EDITING, CLONAL EXPANSION, AND ASSOCIATED APPLICATIONS

CROSS-REFERENCE TO RELATED APPLICATIONS

This application is a continuation of U.S. application Ser. No. 17/259,501, filed Jan. 11, 2021, which is a U.S. National Phase of PCT/US2019/041735, filed Jul. 12, 2019, which claims priority to and the benefit of U.S. Provisional Patent Application No. 62/697,397, filed Jul. 12, 2018, the disclosure of which is hereby incorporated by reference in its entirety.

BACKGROUND

There is a need for assessing the potential for clonal expansion and early stage neoplastic clonal selection, for example of cells carrying cancer driver mutations, in mixed cell populations for a variety of applications. However, currently used assays do not provide the sensitivity to detect such early stage selection. Additionally, there is a need in the field of targeted genome editing for tools to assess successful application of genome editing without further non-targeted nucleic acid alterations.

SUMMARY

The present technology relates generally to methods for detecting and assessing clonal selection and/or expansion, and associated reagents for use in such methods. In particular, some embodiments of the technology are directed to utilizing Duplex Sequencing for assessing clonal selection in mixed cell populations and/or cell populations following an event (e.g., genome editing, mutagenesis, etc.).

In an embodiment, the present technology comprises a method of characterizing a population of cells following an engineered genomic editing event directed to an intended genomic locus, the method comprising: (a) providing a sample comprising double-stranded DNA molecules originating from the population of cells following the engineered genomic editing event; (b) generating an error-corrected sequence read for each of a plurality of the double-stranded DNA molecules, comprising: ligating adapter molecules to the plurality of the double-stranded DNA molecules to generate a plurality of adapter-DNA molecules; generating a set of copies of an original first strand of the adapter-DNA molecule and a set of copies of an original second strand of the adapter-DNA molecule; sequencing one or more copies of the original first and second strands to provide a first strand sequence and a second strand sequence; comparing the first strand sequence and the second strand sequence to identify one or more correspondences between the first and second strand sequences; and (c) comparing one or more error-corrected sequence reads comprising a sequence at the intended genomic locus to an anticipated genome edited DNA sequence; or (d) comparing one or more error-corrected sequence reads comprising a sequence at an unintended genomic locus to a reference genome DNA sequence.

In another embodiment, the present technology comprises a method for characterizing an efficiency of an engineered genomic editing event in a population of cells, wherein the engineered genomic editing event is targeted to an intended genomic locus, the method comprising: (a) preparing a sequencing library from a sample comprising a plurality of double-stranded DNA molecules originating from the population of cells following the genomic editing event, wherein preparing the sequence library comprises ligating asymmetric adapter molecules to the plurality of double-stranded DNA molecules to generate a plurality of adapter-DNA molecules; (b) sequencing first and second strands of the adapter-DNA molecules to provide a first strand sequence read and a second strand sequence read for at least a portion of the adapter-DNA molecules; (c) for each sequenced adapter-DNA molecule, comparing the first strand sequence read and the second strand sequence read to identify one or more correspondences between the first and second strand sequences reads; and (d) determining a frequency of an anticipated genomic sequence at the intended genomic locus among the plurality of double-stranded DNA molecules comprising the intended genomic locus by: analyzing the one or more correspondences between the first and second strand sequence reads; and comparing the correspondences to the anticipated genomic sequence.

In another embodiment, the present technology comprises a method of generating high accuracy sequencing reads of a population of target double-stranded nucleic acid molecules extracted from a genome-edited cell population, the method comprising: (a) duplex sequencing one or more target double-stranded nucleic acid molecules extracted from the cell population; and (b) generating high accuracy consensus sequences for the targeted double-stranded DNA molecules, wherein the target double-stranded nucleic acid molecules comprise an intended genome edited region of DNA and one or more unintended genomic regions of DNA.

In another embodiment, the present technology comprises a method for determining if DNA was successfully genome-edited at an intended genetic locus using an engineered targeted genomic editing event, the method comprising: (a) providing duplex error-corrected sequencing reads for a plurality of double-stranded DNA molecules extracted from a sample following the engineered targeted genomic editing event; and (b) for each genetic locus in a set of one or more genetic loci in a reference genome, quantifying the double-stranded DNA molecules for which the duplex error-corrected sequencing reads have sequences substantially the same as an expected sequence.

In another embodiment, the present technology comprises a method of assessing neoplastic potential of a cell population following an engineered genomic editing event, comprising: (a) preparing a sequencing library from a sample comprising double-stranded DNA molecules originating from the cell population following the engineered genomic editing event, wherein preparing the sequence library comprises tagging a plurality of double-stranded DNA molecules to generate a plurality of tagged DNA molecules having first and second tagged strands; (b) selectively enriching the first and second tagged strands for a subset of tagged DNA molecules that map to one or more cancer drivers to provide enriched tagged DNA molecules; (c) generating an error-corrected sequence read for each of a plurality of enriched tagged DNA molecules, wherein the generating the error-corrected sequence reads comprises: sequencing one or more first and second tagged strands derived from the enriched tagged DNA molecules to provide a first strand sequence and a second strand sequence; comparing the first strand sequence and the second strand sequence to identify one or more correspondences between the first and second strand sequences; and (d) determining if there is a variant present in the one or more cancer drivers among the plurality of enriched tagged DNA molecules by comparing the one or more correspondences to a reference genome sequence.

In another embodiment, the present technology comprises a method for detecting and/or quantifying clonal expansion of a cell in a cell population following an engineered genomic editing event, comprising: (a) duplex sequencing one or more target double-stranded DNA molecules originating from a cell population following the engineered genomic editing event; (b) identifying one or more variants among the target double-stranded DNA molecules; (c) determining a variant frequency of the one or more variants among the target double-stranded DNA molecules originating from the cell population; and (d) comparing the variant frequency for each of the one or more variants to an expected variant frequency.

Other embodiments, aspects and advantages of the present technology are described further in the following detailed description.

BRIEF DESCRIPTION OF THE DRAWINGS

Many aspects of the present disclosure can be better understood with reference to the following figures, which together make up the Drawings. These figures are for illustration purposes only, and not for limitation. The components in the figures are not necessarily to scale. Instead, emphasis is placed on illustrating clearly the principles of the present disclosure.

FIG. 8A is a graph illustrating single nucleotide variants aligning to exon 3 of a human HRAS transgene in a mouse strain genetically predisposed to cancer and in accordance with certain embodiments of the present technology.

DETAILED DESCRIPTION

Figure 1A:
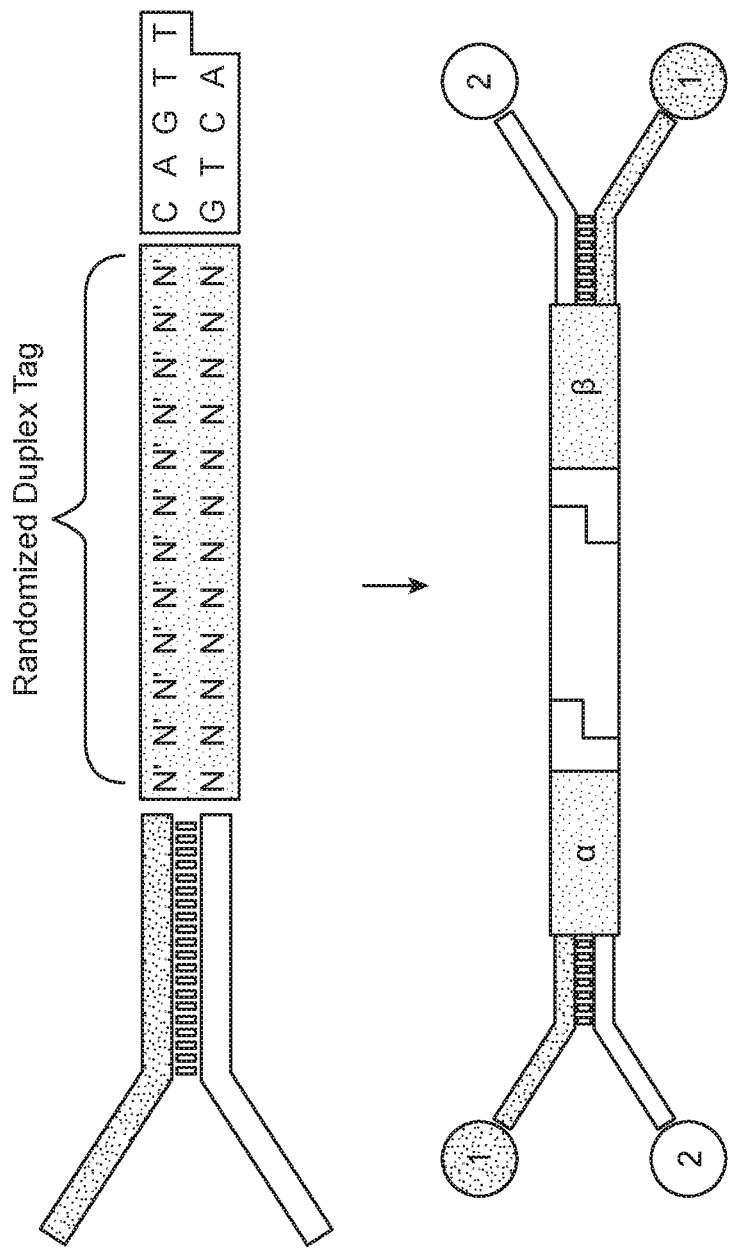
FIG. 1A provides an exemplary nucleic acid adapter molecule for use with some embodiments of the present technology and an exemplary double-stranded adapter-nucleic acid complex resulting from ligation of the adapter molecule to a double-stranded nucleic acid fragment in accordance with some embodiments of the present technology.

The present technology is directed, at least in part, to methods for detecting, assessing and/or quantifying variants (i.e., genetic variants) among populations of cells that have undergone a genomic editing event. For example, in some embodiments, the present disclosure provides methods to detect and/or quantify rare and/or unintended variations during a genomic editing event (e.g., at an intended locus for genomic editing or at an off-target, unintended locus) and associated reagents for use in such methods. In some embodiments, the present disclosure provides methods to detect and/or quantify clonal expansion and associated reagents for use in such methods.

The present disclosure encompasses a recognition that high fidelity sequencing techniques, such as Duplex Sequencing, can be used to detect and/or quantify low frequency genetic variants. In some embodiments, the present disclosure describes using Duplex Sequencing for assessing a clonal selection in mixed cell populations (either in vitro or in vivo) and/or cell populations following a genomic editing event (e.g., an engineered genome editing event or a natural genomic editing event). For example, various embodiments of the present technology include performing Duplex Sequencing methods for identifying one or more genetic variants among target double-stranded nucleic acid molecules and determining a variant frequency of the one or more variants. Further examples of the present technology are directed to methods for detecting and assessing clonal expansion of cells following an event. For example, some embodiments include performing Duplex Sequencing methods for assessing clonal expansion of cells harboring mutations in cancer driving genes and/or that are under selective pressure. Other embodiments include performing Duplex Sequencing methods for assessing clonal expansion of cells based on the use of genetic markers of cell lineage that are not under selective pressure. In still further embodiments, the present technology provides methods of generating high accuracy sequencing reads of a population of double-stranded nucleic acid molecules extracted from a genome-edited cell population. In various arrangements, methods include steps to determine the success of the genome editing event and/or undesired adverse consequences thereof. Various aspects of the present technology have many applications in both pre-clinical and clinical therapies as well as other industry-wide implications.

Specific details of several embodiments of the technology are described below with reference to the Drawing (e.g., FIGS. 1A-8B). Although many of the embodiments are described herein with respect to Duplex Sequencing, other sequencing modalities capable of generating error-corrected sequencing reads, in addition to those described herein, are within the scope of the present technology. Additionally, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1A-8B.

Certain Definitions

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Where ranges are provided herein, the endpoints are included. As used in this application, the term "comprise" and variations of the term, such as "comprising" and "comprises," are not intended to exclude other additives, components, integers or steps.

About: The term "about", when used herein in reference to a value, refers to a value that is similar, in context to the referenced value. In general, those skilled in the art and familiar with the context will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value. For variances of single digit integer values where a single numerical value step in either the positive or negative direction would exceed 25% of the value, "about" is generally accepted by those skilled in the art to include, at least 1, 2, 3, 4, or 5 integer values in either the positive or negative direction, which may or may not cross zero depending on the circumstances. A non-limiting example of this is the supposition that 3 cents can be considered about 5 cents in some situations that would be apparent to one skilled in that art.

Allele: As used herein, the term "allele" refers to one of two or more existing genetic variants of a specific genomic locus.

Analog: As used herein, the term "analog" refers to a substance that shares one or more particular structural features, elements, components, or moieties with a reference substance. Typically, an "analog" shows significant structural similarity with the reference substance (for example, sharing a core or consensus structure), but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Animal: As used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig, etc.). In some embodiments, animals include, but are not limited to, mammals, birds, reptiles, amphibians, fish, insects, and/or worms. In some embodiments, an animal may be a transgenic animal, genetically engineered animal, and/or a clone.

Biological Sample: As used herein, the term "biological sample" or "sample" typically refers to a sample obtained or derived from a biological source (e.g., a tissue or organism or cells or cell culture) of interest, as described herein. As used herein, a "biological sample" is amenable to a genomic editing event. Thus, biological samples of the present disclosure include genomic material. In some embodiments, a biological source of interest comprises an organism, such as an animal (e.g., a mammal, e.g., a human) In some embodiments, a source of interest is a plant-based organism (e.g., a plant, plant part, seed, etc.). In other embodiments, a source of interest comprises a microorganism, such as a bacterium, virus, protozoan, or fungus. In further embodiments, a source of interest may be a synthetic tissue, organism, cell culture, nucleic acid or other material. In other embodiments, a sample may be a multi-organism sample (e.g., a mixed organism sample). In some embodiments, a biological sample is or comprises biological tissue or fluid. In some embodiments, a biological sample may be or comprise bone marrow; blood; blood cells; ascites; tissue samples, biopsy samples or fine needle aspiration samples; cell-containing body fluids; free floating nucleic acids; protein-bound nucleic acids, riboprotein-bound nucleic acids; sputum; plasma, serum, saliva; urine; cerebrospinal fluid, peritoneal fluid; pleural fluid; feces; lymph; gynecological fluids; skin swabs; vaginal swabs; pap smear, oral swabs; nasal swabs; washings or lavages such as a ductal lavages or broncheoalveolar lavages; vaginal fluid, aspirates; scrapings; bone marrow specimens; tissue biopsy specimens; fetal tissue or fluids; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a biological sample can comprise cell-derivatives such as organelles or vesicles or exosomes. In a particular embodiment, a biological sample is a liquid biopsy obtained from a subject. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example, nucleic acids or DNA molecules extracted from a sample or obtained by subjecting a primary sample to techniques such as amplification or reverse transcription of mRNA, isolation and/or purification of certain components, etc.

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. Cancer is familiar to those experienced in the art as being generally characterized by dysregulated growth of abnormal cells, which may metastasize. Cancers include, by way of non-limiting examples, prostate cancer (e.g. adenocarcinoma, small cell), ovarian cancer (e.g., ovarian adenocarcinoma, serous carcinoma or embryonal carcinoma, yolk sac tumor, teratoma), liver cancer (e.g., HCC or hepatoma, angiosarcoma), plasma cell tumors (e.g., multiple myeloma, plasmacytic leukemia, plasmacytoma, amyloidosis, Waldenstrom's macroglobulinemia), colorectal cancer (e.g., colonic adenocarcinoma, colonic mucinous adenocarcinoma, carcinoid, lymphoma and rectal adenocarcinoma, rectal squamous carcinoma), leukemia (e.g., acute myeloid leukemia, acute lymphocytic leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia, T-cell leukemia, Sezary syndrome, systemic mastocytosis, hairy cell leukemia, chronic myeloid leukemia blast crisis), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, follicular lymphoma, mantle cell lymphoma, MALT lymphoma, marginal cell lymphoma, Richter's transformation, double hit lymphoma, transplant associated lymphoma, CNS lymphoma, extranodal lymphoma, HIV-associated lymphoma, endemic lymphoma, Burkitt's lymphoma, transplant-associated lymphoproliferative neoplasms, and lymphocytic lymphoma etc.), cervical cancer (e.g., squamous cervical carcinoma, clear cell carcinoma, HPV-associated carcinoma, cervical sarcoma etc.) esophageal cancer (e.g., esophageal squamous cell carcinoma, adenocarcinoma, certain grades of Barretts esophagus, esophageal adenocarcinoma), melanoma (e.g., dermal melanoma, uveal melanoma, acral melanoma, amelanotic melanoma etc.), CNS tumors (e.g., oligodendroglioma, astrocytoma, glioblastoma multiforme, meningioma, schwannoma, craniopharyngioma etc.), pancreatic cancer (e.g., adenocarcinoma, adenosquamous carcinoma, signet ring cell carcinoma, hepatoid carcinoma, colloid carcinoma, islet cell carcinoma, pancreatic neuroendocrine carcinoma etc.), gastrointestinal stromal tumor, sarcoma (e.g., fibrosarcoma, myxosarcoma, liposarcoma, chondrosarcoma, osteogenic sarcoma, angiosarcoma, endothelioma sarcoma, lymphangiosarcoma, lymphangioendothelioma sarcoma, leiomyosarcoma, Ewing's sarcoma, and rhabdomyosarcoma, spindle cell tumor etc.), breast cancer (e.g., inflammatory carcinoma, lobar carcinoma, ductal carcinoma etc.), ER-positive cancer, HER-2 positive cancer, bladder cancer (squamous bladder cancer, small cell bladder cancer, urothelial cancer etc.), head and neck cancer (e.g., squamous cell carcinoma of the head and neck, HPV-associated squamous cell carcinoma, nasopharyngeal carcinoma etc.), lung cancer (e.g., non-small cell lung carcinoma, large cell carcinoma, bronchogenic carcinoma, squamous cell cancer, small cell lung cancer etc.), metastatic cancer, oral cavity cancer, uterine cancer (leiomyosarcoma, leiomyoma etc.), testicular cancer (e.g., seminoma, non-seminoma, and embryonal carcinoma yolk sack tumor etc.), skin cancer (e.g., squamous cell carcinoma, and basal cell carcinoma, merkel cell carcinoma, melanoma, cutaneous t-cell lymphoma etc.), thyroid cancer (e.g., papillary carcinoma, medullary carcinoma, anaplastic thyroid cancer etc.), stomach cancer, intra-epithelial cancer, bone cancer, biliary tract cancer, eye cancer, larynx cancer, kidney cancer (e.g., renal cell carcinoma, Wilms tumor etc.), gastric cancer, blastoma (e.g., nephroblastoma, medulloblastoma, hemangioblastoma, neuroblastoma, retinoblastoma etc.), myeloproliferative neoplasms (polycythemia vera, essential thrombocytosis, myelofibrosis, etc.), chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, pheochromocytoma, small cell lung cancer, peritoneal mesothelioma, hyperparathyroid adenoma, adrenal cancer, cancer of unknown primary, cancer of the endocrine system, cancer of the penis, cancer of the urethra, cutaneous or intraocular melanoma, a gynecologic tumor, solid tumors of childhood, or neoplasms of the central nervous system, primary mediastinal germ cell tumor, clonal hematopoiesis of indeterminate potential, smoldering myeloma, monoclonal gammaglobulinopathy of unknown significant, monoclonal B-cell lymphocytosis, low grade cancers, clonal field defects, preneoplastic neoplasms, ureteral cancer, autoimmune-associated cancers (i.e. ulcerative colitis, primary sclerosing cholangitis, celiac disease), cancers associated with an inherited predisposition (i.e. those carrying genetic defects in such as BRCA1, BRCA2, TP53, PTEN, ATM, etc.) and various genetic syndromes such as MEN1, MEN2 trisomy 21 etc.) and those occurring when exposed to chemicals in utero (i.e. clear cell cancer in female offspring of women exposed to Diethylstilbestrol [DES]), among many others. In some embodiments, variants detected, analyzed and/or quantified in the context of the present disclosure are associated with cancer (e.g., neoplastic variants).

Cancer driver or Cancer driver gene: As used herein, "cancer driver" or "cancer driver gene" refers to a genetic lesion that has the potential to allow a cell, in the right context, to undergo, or begin to undergo, a malignant transformation. Such genes include tumor suppressors (e.g., TP53, BRCA1) that normally suppress malignancy transformation and when mutated in certain ways, no longer do. Other driver genes can be oncogenes (e.g., KRAS, EGFR) that when mutated in certain ways become constitutively active or gain new properties that facilitate a cell to become malignant. Other mutations found in non-coding regions of the genome can be cancer drivers. For example, a mutation of the promoter region of the telomerase gene (TERT) can result in overexpression of the gene and thus become a cancer driver. Other mutations in non-coding regions can facilitate aberrant splicing or modulate transcription factor binding or other regulatory changes that can, in certain cases, lead to neoplastic growth. Certain rearrangements (e.g., BCR-ABL fusion) can juxtapose one genetic region with that of another to drive tumorigenesis through mechanisms related to overexpression, loss of repression or chimeric fusion genes. Broadly speaking, genetic mutations (or epimutations) that confer a phenotype to a cell that facilitates its proliferation, survival, or competitive advantage over other cells or that renders its ability to evolve more robust, can be considered a driver mutation. This is to be contrasted with mutations that lack such features, even if they may happen to be in the same gene (i.e. a synonymous mutation). When such mutations are identified in tumors, they are commonly referred to as passenger mutations because they "hitchhiked" along with the clonal expansion without meaningfully contributing to the expansion. As recognized by one of ordinary skill in the art, the distinction of driver and passenger is not absolute and should not be construed as such. Some drivers only function in certain situations (e.g., certain tissues) and others may not operate in the absence of other mutations or epimutations or other factors.

Clonal expansion. As used herein, "clonal expansion" refers to the clonal outgrowth of a population of cells derived from a common founder cell. The derivative population of cells (i.e. daughter cells), may be referred to as simply a clone. Clonal expansions can occur through artificial means (i.e. a single isolated cell in culture is allowed to grow and iteratively divide into a population of cells). as a result of normal healthy biological processes (i.e. a fertilized egg is founding cell of a human, all the cells of which comprise a clone). Clonal expansions may also occur as a result of pathogenic processes, such as when a cell in the body gains the ability to progressively grow and divide when it should not and forms a tumor comprising its daughter cells. Clones, by their very nature contain subclones—that is, smaller populations of cells that are clonally derived from a daughter cell of the original clonal founder. These subclones are, themselves, simply clones when viewed in reference to their specific founder cell, but are referred to as subclones when viewed relative to an even earlier founding cell.

The term "clone" or "clonal expansion" does not, itself, necessarily indicate which of the above, or other processes may have led to the clonal outgrowth. A clonal expansion may occur within a population of related cells (i.e. one cell in a human that forms a tumor within healthy tissue) or unrelated cells (i.e. a population of cells in culture that was established from the cells of many different people). In general, to recognize a cell that is undergoing clonal expansion within a larger cell population, there usually needs to be at least one unique lineage marker of some form to differentiate that cell and its daughter cells from other cells in the population. That lineage marker may be a genetic variant that is substantially unique to the founder cell and is propagated to the daughter cells. Such a genetic variant may be a mutation in the nuclear genome, the mitochondrial genome, epi-mutations other heritable changes or changes to other molecules in the cell (i.e. proteins) that result from the above and can be detected. The specific lineage marker of a clonal expansion/clone may itself be responsible or contributory to the expansion (i.e. a "driver") or may simply mark the clone and serve no specific function (i.e. a "passenger" or "hitchhiker".

Clonal expansion of a cell in a heterogeneous cell population may arise for a variety of reasons, including stochastic clonal expansion, increased rate of growth, reduced senescence, reduced contact inhibition. In these latter cases the clonal expansions occur as a result of a positive growth bias (e.g., a relative growth advantage) compared to other cells in a population of cells. This increased or preferential reproduction of a single cell produces a greater number of daughter/derivative cells than other cells in a heterogeneous cell population, such that daughter or derivative cells from that cell disproportionately expand in the cell population to form a clone. For example, in some embodiments, a cell that undergoes clonal expansion is neoplastic. In some embodiments, a cell that undergoes clonal expansion is healthier than other cells in a heterogeneous cell population (e.g., other cells in the population have a negative growth bias).

Clonal selection; As used herein, "clonal selection" refers to a selection or positive bias for a particular cell in a population. Generally, clonal selection is an event and/or signal that results in an increased or preferential reproduction of a single cell to produce a greater number of daughter/derivative cells than other cells in a heterogeneous cell population, such that daughter or derivative cells from that cell are disproportionately expanding or surviving in the cell population.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information (for example, utilizing a computer or other processing unit adapted to perform a relevant analysis). In some embodiments, determining involves receiving relevant information and/or materials from a source. In some embodiments, determining involves comparing one or more features of a sample or entity to a comparable reference.

Duplex Sequencing (DS): As used herein, "Duplex Sequencing (DS)" is, in its broadest sense, refers to an error-correction method that achieves exceptional accuracy by comparing the sequence from both strands of individual DNA molecules.

Engineered: Those of ordinary skill in the art, reading the present disclosure, will appreciate that the term "engineered", as used herein, refers to an aspect of having been manipulated and altered by the hand of man. In particular, the term "engineered cell" refers to a cell that has been subjected to a manipulation, so that its genetic, epigenetic, and/or phenotypic identity is altered relative to an appropriate reference cell such as otherwise identical cell that has not been so manipulated. In some embodiments, the manipulation is or comprises a genetic manipulation, such as gene editing, base editing and gene therapy. In some embodiments, an engineered cell is one that has been manipulated so that it contains and/or expresses a particular agent of interest (e.g., a protein, a nucleic acid, and/or a particular form thereof) in an altered amount and/or according to altered timing relative to such an appropriate reference cell.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Gene. As used herein, the term "gene" refers to a DNA sequence in a chromosome that codes for a product (e.g., an RNA product and/or a polypeptide product). In some embodiments, a gene includes coding sequence (i.e., sequence that encodes a particular product); in some embodiments, a gene includes non-coding sequence. In some particular embodiments, a gene may include both coding (e.g., exonic) and non-coding (e.g., intronic) sequences. In some embodiments, a gene may include one or more regulatory elements that, for example, may control or impact one or more aspects of gene expression (e.g., cell-type-specific expression, inducible expression, etc.).

Genome editing: As used herein, "genome editing", "genomic editing" or "genome engineering" refers to processes for altering or engineering changes to nucleic acid (e.g., genomic DNA, mitochondrial DNA or other DNA) in a living organism (e.g., a cell or multiple cells). Genome editing can include providing systems for inserting, deleting, modifying, replacing, correcting, interrupting, damaging, rendering non-functional, or mutating nucleic acid sequence(s) in the genome of the living organism. Targeted genome editing comprises methods in which specific sequences can be changed (e.g., "edited"), for example, at an intended genomic locus. Genetic tools, such as, for example, programmable site-specific nucleases, can be used to direct desired alterations to a genome in vivo. Genome editing can be achieved by genetic manipulation of a DNA sequence in vitro or in another living organism followed by insertion of this sequence into a genome of interest.

gRNA: As used herein, "gRNA" or "guide RNA", refers to short RNA molecules which include a scaffold sequence suitable for a targeted endonuclease (e.g., a Cas enzyme such as Cas9 or Cpf1 or another ribonucleoprotein with similar properties, etc.) binding to a substantially target-specific sequence which facilitates cutting of a specific region of DNA or RNA.

Homology: As used herein, the term "homology" refers to the overall relatedness between polymeric molecules, e.g., between nucleic acid molecules (e.g., DNA molecules and/or RNA molecules). In some embodiments, polymeric molecules are considered to be "homologous" to one another if their sequences are at least 80%, 85%, 90%, 95%, or 99% identical. In other embodiments the degree of similarity may be less than 30%, at least 30% 40%, 50%, 60%, 70% or more than 70%. As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Algorithms and computer programs useful in determining the percent homology between two nucleotide sequences are well known in the art.

Mutation: As used herein, the term "mutation" refers to alterations to nucleic acid sequence or structure relative to a reference sequence. Mutations to a polynucleotide sequence can include point mutations (e.g., single base mutations), multinucleotide mutations, nucleotide deletions, sequence rearrangements, nucleotide insertions, and duplications of the DNA sequence in the sample, among complex multinucelotide changes. Mutations can occur on both strands of a duplex DNA molecule as complementary base changes (i.e. true mutations), or as a mutation on one strand but not the other strand (i.e. heteroduplex), that has the potential to be either repaired, destroyed or be mis-repaired/converted into a true double stranded mutation. Reference sequences may be present in databases (i.e. HG38 human reference genome) or the sequence of another sample to which a sequence is being compared. Mutations are also known as genetic variant.

Mutant frequency: As used herein, the term "mutant frequency", also sometimes referred to as "mutational frequency", refers to the number of unique mutations detected per the total number of base-pairs sequenced. In some embodiments the unique mutations are defined as Duplex Sequencing verified mutations and the total number of base-pairs sequenced is defined as those verified by Duplex Sequencing. In some embodiments, the mutant frequency is the frequency of mutations within only a specific gene, a set of genes, or a set of genomic targets. In some embodiments mutant frequency may refer to only certain types of mutations (for example the frequency of A>T mutations, which is calculated as the number of A>T mutations per the total number of A bases). The frequency at which mutations arise into a population of cells or molecules can vary by age of a subject, over time, by tissue or organization type, by region of a genome, by type of mutation, by trinucleotide context, inherited genetic background, by exposure to mutagenic chemicals, by exposure to radiation, and by exposure to an environment comprising any of the above, among other things.

Mutation signature: As used herein, the term "mutation signature", "mutation spectrum" or mutation spectra" refers to characteristic combinations of mutation types arising from mutagenesis processes such as genomic editing (e.g., natural genomic editing or engineered genomic editing), DNA replication infidelity, exogenous and endogenous genotoxin exposures, defective DNA repair pathways and DNA enzymatic editing. Mutational spectra may comprise trinucleotide mutation spectra which entails the pattern of relative abundance of possible types of mutations among three base-pair nucleotide sequence contexts. Such spectra may be normalized by the relative abundance of a sequence context in a reference genome. Mutational spectra may entail mutations of any type in any sequence context. In an embodiment, the mutation spectrum is may be compared to the mutation spectrum of other samples or data sets by computational pattern matching (e.g., unsupervised hierarchical mutation spectrum clustering, non-negative matrix factorization etc.).

Nucleic acid. As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "Peptide nucleic acids", which are known in the art and have peptide bonds instead of phosphodiester bonds in the backbone, and which are considered within the scope of the present technology. Alternatively, or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template {in vivo or in vitro), reproduction in a recombinant cell or system, and chemical synthesis. In some embodiments, a nucleic acid is at least 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double-stranded. In some embodiments a nucleic acid may be branched of have secondary structures. In some embodiments a nucleic acid has a nucleotide sequence comprising at least one element that encodes, or is the complement of a sequence that encodes, a polypeptide. In some embodiments, a nucleic acid has enzymatic activity. In some embodiments the nucleic acid serves a mechanical function, for example in a ribonucleoprotein complex or a transfer RNA.

Passenger Mutation: As used herein, the term "passenger mutation" refers to mutations are identified in a clone but are not believed to have contributed to the clonal expansion itself. This is in contrast to a "driver mutation:" which is reasonably believed to have functionally contributed to clonal expansion itself.

Polynucleotide damage: As used herein, the term "polynucleotide damage" or "nucleic acid damage" refers to damage to a subject's deoxyribonucleic acid (DNA) sequence ("DNA damage") or ribonucleic acid (RNA) sequence ("RNA damage") that is directly or indirectly (e.g. a metabolite, or induction of a process that is damaging or mutagenic) caused by or precipitated by ex vivo or in vivo factors (e.g., exposure to a genotoxin, aging, metabolic processes, etc.). Damaged nucleic acid may lead to the onset of a disease or disorder, for example, a disease or disorder associated with genotoxin exposure in a subject, aging, or other mutagenic processes. In some embodiments, detection of damaged nucleic acid in a subject may be an indication of a genotoxin exposure. Polynucleotide damage may further comprise chemical and/or physical modification of the DNA in a cell. In some embodiments, the damage is or comprises, by way of non-limiting examples, at least one of oxidation, alkylation, deamination, methylation, hydrolysis, hydroxylation, nicking, intra-strand crosslinks, inter-strand cross links, blunt end strand breakage, staggered end double strand breakage, phosphorylation, dephosphorylation, sumoylation, glycosylation, deglycosylation, putrescinylation, carboxylation, halogenation, formylation, single-stranded gaps, damage from heat, damage from desiccation, damage from UV exposure, damage from gamma radiation damage from X-radiation, damage from ionizing radiation, damage from non-ionizing radiation, damage from heavy particle radiation, damage from nuclear decay, damage from beta-radiation, damage from alpha radiation, damage from neutron radiation, damage from proton radiation, damage from cosmic radiation, damage from high pH, damage from low pH, damage from reactive oxidative species, damage from free radicals, damage from peroxide, damage from hypochlorite, damage from tissue fixation such formalin or formaldehyde, damage from reactive iron, damage from low ionic conditions, damage from high ionic conditions, damage from unbuffered conditions, damage from nucleases, damage from environmental exposure, damage from fire, damage from mechanical stress, damage from enzymatic degradation, damage from microorganisms, damage from preparative mechanical shearing, damage from preparative enzymatic fragmentation, damage having naturally occurred in vivo, damage having occurred during nucleic acid extraction, damage having occurred during sequencing library preparation, damage having been introduced by a polymerase, damage having been introduced during nucleic acid repair, damage having occurred during nucleic acid end-tailing, damage having occurred during nucleic acid ligation, damage having occurred during sequencing, damage having occurred from mechanical handling of DNA, damage having occurred during passage through a nanopore, damage having occurred as part of aging in an organism, damage having occurred as a result if chemical exposure of an individual, damage having occurred by a mutagen, damage having occurred by a carcinogen, damage having occurred by a clastogen, damage having occurred from in vivo inflammation damage due to oxygen exposure, damage due to one or more strand breaks, and any combination thereof.

Reference: As used herein, "reference" describes a standard or control relative to which a comparison is performed. For example, in some embodiments, an agent, animal, individual, population, sample, sequence or value of interest is compared with a reference or control agent, animal, individual, population, sample, sequence or value or representation thereof in a physical or computer database that may be present at a location or accessed remotely via electronic means. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Reference sample: As used herein, a "reference sample" refers to a sample that is otherwise the same as a sample to which it is compared, except that the reference sample has not undergone a genomic editing event. For example, a reference sample may be isolated in the same way as a sample to which it is compared (e.g., a test sample), except that the reference sample has not been induced to undergo a genomic editing event (e.g., an engineered genomic editing event).

Safe threshold variant frequency: As used herein, the term "safe threshold variant frequency", also sometimes referred to as "safe threshold mutant frequency" refers to an acceptable rate of mutation or variant generation and/or total abundance caused by a genomic editing event or process or another mutagenic process, below which a there is an acceptable risk of neoplastic potential or other genetic perturbation in a cell. Toleration of acceptable risk of resultant mutation rate of variant generation may differ depending on cell type, application of the genomic editing event, subject, age, gender, tissue type, health condition of a patient, etc.

Single Nucleotide Polymorphism (SNP): As used herein, the term "single nucleotide polymorphism" or "SNP" refers to a particular base position in the genome where alternative bases are known to distinguish one allele from another. SNPs refer to variations that are single nucleotide in nature as opposed to MNVs which refer to multinucleotide variants. A "copy number polymorphism" or "copy number variant" (referred to as CNPs or CNVs) refers to a variation in the number of copies of a sequence within the DNA. In some embodiments, one or a few SNPs and/or CNPs is/are sufficient to distinguish complex genetic variants from one another so that, for analytical purposes, one or a set of SNPs and/or CNPs may be considered to be characteristic of a particular variant, trait, cell type, individual, species, etc., or set thereof. In some embodiments, one or a set of SNPs and/or CNPs may be considered to define a particular variant, trait, cell type, individual, species, etc., or set thereof. In the most common usage, SNP generally implies the variant in question is inherited from the germline. The broader term Single Nucleotide Variant (SNV) may entail an inherited SNP or a somatically acquired mutation.

Single Molecule Identifier (SMI): As used herein, the term "single molecule identifier" or "SMI", (which may be referred to as a "tag" a "barcode", a "molecular bar code", a "Unique Molecular Identifier", or "UMI", among other names) refers to any material (e.g., a nucleotide sequence, a nucleic acid molecule feature) that is capable of substantially distinguishing an individual molecule among a larger heterogeneous population of molecules, either alone or in combination with another molecular feature. In some embodiments, a SMI can be or comprise an exogenously applied SMI. In some embodiments, an exogenously applied SMI may be or comprise a degenerate or semi-degenerate sequence. In some embodiments, substantially degenerate SMIs may be known as Random Unique Molecular Identifiers (R-UMIs). In some embodiments, an SMI may comprise a code (for example a nucleic acid sequence) from within a pool of known codes. In some embodiments, pre-defined SMI codes are known as Defined Unique Molecular Identifiers (D-UMIs). In some embodiments, a SMI can be or comprise an endogenous SMI. In some embodiments, an endogenous SMI may be or comprise information related to specific shear-points of a target sequence, features relating to the terminal ends of individual molecules comprising a target sequence, or a specific sequence at or adjacent to or within a known distance from an end of individual molecules. In some embodiments, an SMI may relate to a sequence variation in a nucleic acid molecule cause by random or semi-random damage, chemical modification, enzymatic modification or other modification to the nucleic acid molecule. In some embodiments the modification may be deamination of methylcytosine. In some embodiments, the modification may entail sites of nucleic acid nicks. In some embodiments, an SMI may comprise both exogenous and endogenous elements. In some embodiments, an SMI may comprise physically adjacent SMI elements. In some embodiments, SMI elements may be spatially distinct in a molecule. In some embodiments, an SMI may be a non-nucleic acid. In some embodiments, an SMI may comprise two or more different types of SMI information. Various embodiments of SMIs are further disclosed in International Patent Publication No. WO2017/100441, which is incorporated by reference herein in its entirety.

Strand Defining Element (SDE): As used herein, the term "Strand Defining Element" or "SDE", refers to any material which allows for the identification of a specific strand of a double-stranded nucleic acid material and thus differentiation from the other/complementary strand (e.g., any material that renders the amplification products of each of the two single stranded nucleic acids resulting from a target double-stranded nucleic acid substantially distinguishable from each other after sequencing or other nucleic acid interrogation). In some embodiments, a SDE may be or comprise one or more segments of substantially non-complementary sequence within an adapter sequence. In particular embodiments, a segment of substantially non-complementary sequence within an adapter sequence can be provided by an adapter molecule comprising a Y-shape or a "loop" shape. In other embodiments, a segment of substantially non-complementary sequence within an adapter sequence may form an unpaired "bubble" in the middle of adjacent complementary sequences within an adapter sequence. In other embodiments, an SDE may encompass a nucleic acid modification. In some embodiments, an SDE may comprise physical separation of paired strands into physically separated reaction compartments. In some embodiments, an SDE may comprise a chemical modification. In some embodiments an SDE may comprise a modified nucleic acid. In some embodiments, an SDE may relate to a sequence variation in a nucleic acid molecule caused by random or semi-random damage, chemical modification, enzymatic modification or other modification to the nucleic acid molecule. In some embodiments the modification may be deamination of methylcytosine. In some embodiments the modification may entail sites of nucleic acid nicks. Various embodiments of SDEs are further disclosed in International Patent Publication No. WO2017/100441, which is incorporated by reference herein in its entirety.

Subject: As used herein, the term "subject" refers an organism, typically a mammal, such as a human (in some embodiments including prenatal human forms), a non-human animal (e.g., mammals and non-mammals including, but not limited to, non-human primates, horses, sheep, dogs, cows, pigs, chickens, amphibians, reptiles, sea-life (generally excluding sea monkeys), other model organisms such as worms, flies, zebrafish, etc.), and transgenic animals (e.g., transgenic rodents), etc. In some embodiments, a subject is to be treated or exposed to cells that have undergone a genome editing event. In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject has one or more features characteristic of susceptibility to or risk of a disease, disorder, or condition. In some embodiments, a subject is an individual to whom diagnosis and/or therapy is and/or has been administered. In other embodiments, a biological sample is isolated, extracted or otherwise obtained from a subject. In some embodiments, a subject refers to any living biological sources or other nucleic acid material, that can be genome edited, and can include, for example, organisms, cells, and/or tissues, such as for in vivo studies, e.g.: fungi, plants, protozoans, bacteria, archaebacteria, viruses, isolated cells in culture, cells that have been intentionally (e.g., stem cell transplant, organ transplant) or unintentionally (i.e. fetal or maternal microchimerism) edited or isolated nucleic acids or organelles (i.e. mitochondria, chloroplasts, free viral genomes, free plasmids, aptamers, ribozymes or derivatives or precursors of nucleic acids (i.e. oligonucleotides, dinucleotide triphosphates, etc.).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment.

Trinucleotide or trinucleotide context: As used herein, the terms "trinucleotide" or "trinucleotide context" refers to a nucleotide within the context of nucleotide bases immediately preceding and immediately following in sequence (e.g., a mononucleotide within a three-mononucleotide combination).

Trinucleotide spectrum or signature: Herein, the term "trinucleotide signature", used interchangeably with "trinucleotide spectrum", "triplet signature" and "triplet spectrum", refers to a mutation signature, in a trinucleotide context. In certain embodiments, a genome editing event can have a unique, semi-unique and/or otherwise identifiable triplet spectrum/signature. In some cases, a mutant signature, also known as a mutational signature, comprises a trinucleotide signature.

Treatment: As used herein, the term "treatment" refers to the application or administration of a therapeutic agent to a subject, or application or administration of a therapeutic agent to an isolated tissue or cell line from a subject, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. Treatment may also refer to the application of an exposure or process to a subject or cells for the purpose of inducing a change that is not intended to cure, heal, alleviate, relieve, alter, remedy, ameliorate, improve, or affect the disease, the symptoms of disease. For example, a laboratory animal may be treated with a harmful chemical, for the purpose of assessing its adverse effect on the rodent subject, such as to predict its effect on humans.

Variant: As used herein, the term "variant" refers to an entity that shows significant structural identity with a reference entity, but differs structurally from the reference entity in the presence or level of one or more chemical moieties as compared with the reference entity. In the context of nucleic acids, a variant nucleic acid may have a characteristic sequence element comprised of a plurality of nucleotide residues having designated positions relative to another nucleic acid in linear or three-dimensional space. Sequences with homology differ by one or more variant. For example, a variant polynucleotide (e.g., DNA) may differ from a reference polynucleotide as a result of one or more differences in nucleic acid sequence. In some embodiments, a variant polynucleotide sequence includes an insertion, deletion, substitution or mutation relative to another sequence (e.g., a reference sequence or other polynucleotide (e.g., DNA) sequences in a sample). Examples of variants include SNPs, SNVs, CNVs, CNPs, MNVs, MNPs, mutations, cancer mutations, driver mutations, passenger mutations, inherited polymorphisms.

Variant frequency. As used herein, the term "variant frequency" refers to the relative frequency of a genetic variant at a particular locus in a population, expressed as a fraction or percentage of the population. The population may be a population of cells, a population of organisms, a population of subjects, or a population of molecules or a population of DNA molecules, among others.

Variant allele frequency. As used herein, the term "variant allele frequency" refers to the relative frequency of an allele (variant of a gene) at a particular locus in a population (e.g., a fraction of all chromosomes in the population that carry a particular allele among a population of cells, a population of organisms, a population of subjects, or a population of molecules or a population of DNA molecules, among others.

Figures 1B, 1C:
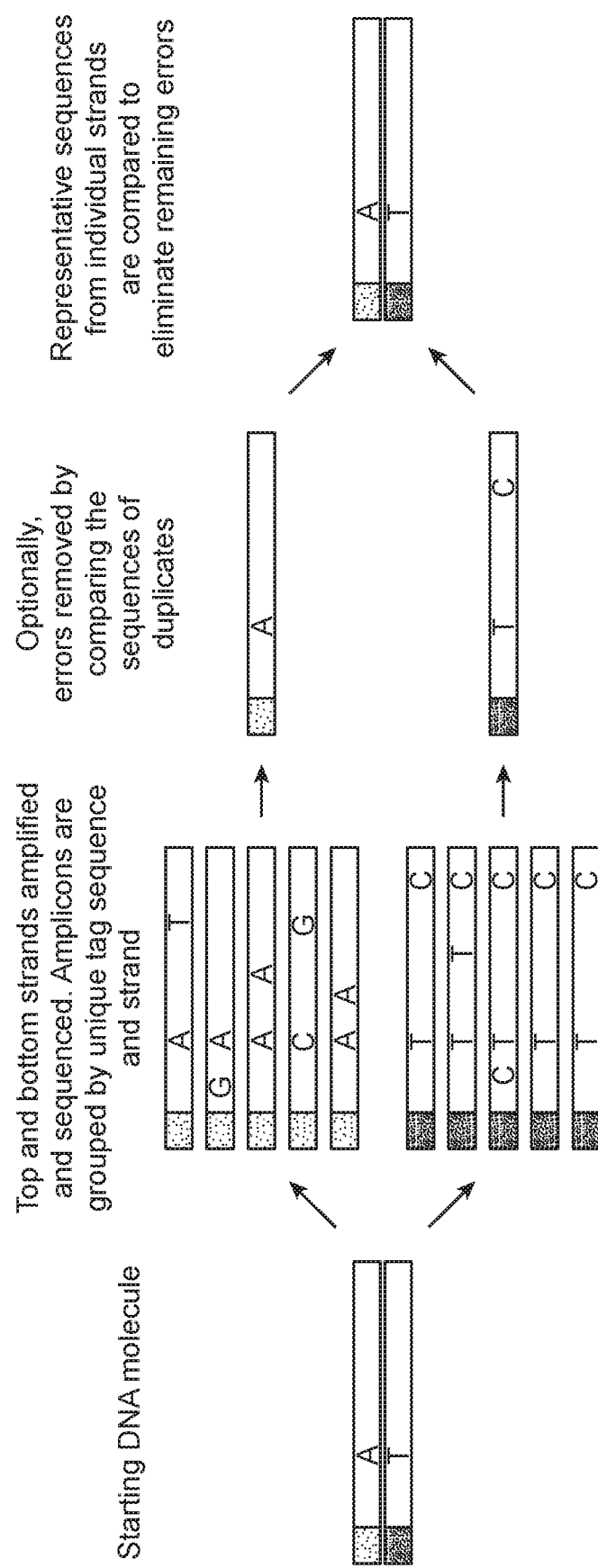
FIG. 1B is a conceptual illustration of various Duplex Sequencing method steps in accordance with some embodiments of the present technology.
FIG. 1C is a conceptual illustration of various Duplex Sequencing method steps in accordance with some embodiments of the present technology.

Selected Embodiments of Duplex Sequencing Methods and Associated Adapters and Reagents Duplex Sequencing is a method for producing error-corrected DNA sequences from double stranded nucleic acid molecules, and which was originally described in International Patent Publication No. WO 2013/142389 and in U.S. Pat. No. 9,752,188, and WO 2017/100441, in Schmitt et. al, PNAS, 2012 [1]; in Kennedy et. al, PLOS Genetics, 2013 [2]; in Kennedy et. al., Nature Protocols, 2014 [3]; and in Schmitt et. al., Nature Methods, 2015 [4]. Each of the above-mentioned patents, patent applications and publications are incorporated herein by reference in their entireties. As illustrated in FIGS. 1A-1C, and in certain aspects of the technology, Duplex Sequencing can be used to independently sequence both strands of individual DNA molecules in such a way that the derivative sequence reads can be recognized as having originated from the same double-stranded nucleic acid parent molecule during massively parallel sequencing (MPS), also commonly known as next generation sequencing (NGS), but also differentiated from each other as distinguishable entities following sequencing. The resulting sequence reads from each strand are then compared for the purpose of obtaining an error-corrected sequence of the original double-stranded nucleic acid molecule known as a Duplex Consensus Sequence (DCS). The process of Duplex Sequencing makes it possible to explicitly confirm that both strands of an original double stranded nucleic acid molecule are represented in the generated sequencing data used to form a DCS.

In certain embodiments, methods incorporating DS may include ligation of one or more sequencing adapters to a target double-stranded nucleic acid molecule, comprising a first strand target nucleic acid sequence and a second strand target nucleic sequence, to produce a double-stranded target nucleic acid complex (e.g. FIG. 1A).

In various embodiments, a resulting target nucleic acid complex can include at least one SMI sequence, which may entail an exogenously applied degenerate or semi-degenerate sequence (e.g., randomized duplex tag shown in FIG. 1A, sequences identified as a and β in FIG. 1A), endogenous information related to the specific shear-points of the target double-stranded nucleic acid molecule, or a combination thereof. The SMI can render the target-nucleic acid molecule substantially distinguishable from the plurality of other molecules in a population being sequenced either alone or in combination with distinguishing elements of the nucleic acid fragments to which they were ligated. The SMI element's substantially distinguishable feature can be independently carried by each of the single strands that form the double-stranded nucleic acid molecule such that the derivative amplification products of each strand can be recognized as having come from the same original substantially unique double-stranded nucleic acid molecule after sequencing. In other embodiments, the SMI may include additional information and/or may be used in other methods for which such molecule distinguishing functionality is useful, such as those described in the above-referenced publications. In another embodiment, the SMI element may be incorporated after adapter ligation. In some embodiments, the SMI is double-stranded in nature. In other embodiments it is single-stranded in nature (e.g., the SMI can be on the single-stranded portion(s) of the adapters). In other embodiments, it is a combination of single-stranded and double-stranded in nature.

In some embodiments, each double-stranded target nucleic acid sequence complex can further include an element (e.g., an SDE) that renders the amplification products of the two single-stranded nucleic acids that form the target double-stranded nucleic acid molecule substantially distinguishable from each other after sequencing. In one embodiment, an SDE may comprise asymmetric primer sites comprised within the sequencing adapters, or, in other arrangements, sequence asymmetries may be introduced into the adapter molecules not within the primer sequences, such that at least one position in the nucleotide sequences of the first strand target nucleic acid sequence complex and the second stand of the target nucleic acid sequence complex are different from each other following amplification and sequencing. In other embodiments, the SMI may comprise another biochemical asymmetry between the two strands that differs from the canonical nucleotide sequences A, T, C, G or U, but is converted into at least one canonical nucleotide sequence difference in the two amplified and sequenced molecules. In yet another embodiment, the SDE may be a means of physically separating the two strands before amplification, such that the derivative amplification products from the first strand target nucleic acid sequence and the second strand target nucleic acid sequence are maintained in substantial physical isolation from one another for the purposes of maintaining a distinction between the two. Other such arrangements or methodologies for providing an SDE function that allows for distinguishing the first and second strands may be utilized, such as those described in the above-referenced publications, or other methods that serves the functional purpose described.

After generating the double-stranded target nucleic acid complex comprising at least one SMI and at least one SDE, or where one or both of these elements will be subsequently introduced, the complex can be subjected to DNA amplification, such as with PCR, or any other biochemical method of DNA amplification (e.g., rolling circle amplification, multiple displacement amplification, isothermal amplification, bridge amplification or surface-bound amplification, such that one or more copies of the first strand target nucleic acid sequence and one or more copies of the second strand target nucleic acid sequence are produced (e.g., FIG. 1B)). The one or more amplification copies of the first strand target nucleic acid molecule and the one or more amplification copies of the second target nucleic acid molecule can then be subjected to DNA sequencing, preferably using a "Next-Generation" massively parallel DNA sequencing platform (e.g., FIG. 1B).

The sequence reads produced from either the first strand target nucleic acid molecule and the second strand target nucleic acid molecule, derived from the original double-stranded target nucleic acid molecule, can be identified based on sharing a related substantially unique SMI and distinguished from the opposite strand target nucleic acid molecule by virtue of an SDE. In some embodiments, the SMI may be a sequence based on a mathematically-based error correction code (for example, a Hamming code), whereby certain amplification errors, sequencing errors or SMI synthesis errors can be tolerated for the purpose of relating the sequences of the SMI sequences on complementary strands of an original Duplex (e.g., a double-stranded nucleic acid molecule). For example, with a double stranded exogenous SMI where the SMI comprises 15 base pairs of fully degenerate sequence of canonical DNA bases, an estimated $4^{15}=1,073,741,824$ SMI variants will exist in a population of the fully degenerate SMIs. If two SMIs are recovered from reads of sequencing data that differ by only one nucleotide within the SMI sequence out of a population of 10,000 sampled SMIs, one can mathematically calculate the probability of this occurring by random chance, a decision can be made whether it is more probable that the single base pair difference reflects one of the aforementioned types of errors, and the SMI sequences could be determined to have in fact derived from the same original duplex molecule. In some embodiments where the SMI is, at least in part, an exogenously applied sequence where the sequence variants are not fully degenerate to each other and are, at least in part, known sequences, the identity of the known sequences can in some embodiments be designed in such a way that one or more errors of the aforementioned types will not convert the identity of one known SMI sequence to that of another SMI sequence, such that the probability of one SMI being misinterpreted as that of another SMI is reduced. In some embodiments this SMI design strategy comprises a Hamming Code approach or derivative thereof. Once identified, one or more sequence reads produced from the first strand target nucleic acid molecule are compared with one or more sequence reads produced from the second strand target nucleic acid molecule to produce an error-corrected target nucleic acid molecule sequence (e.g., FIG. 1C). For example, nucleotide positions where the bases from both the first and second strand target nucleic acid sequences agree are deemed to be true sequences, whereas nucleotide positions that disagree between the two strands are recognized as potential sites of technical errors that may be discounted, eliminated, corrected or otherwise identified. An error-corrected sequence of the original double-stranded target nucleic acid molecule can thus be produced (shown in FIG. 1C). In some embodiments, and following separately grouping of each of the sequencing reads produced from the first strand target nucleic acid molecule and the second strand target nucleic acid molecule, a single-strand consensus sequence can be generated for each of the first and second strands. The single-stranded consensus sequences from the first strand target nucleic acid molecule and the second strand target nucleic acid molecule can then be compared to produce an error-corrected target nucleic acid molecule sequence (e.g., FIG. 1C).

Alternatively, in some embodiments, sites of sequence disagreement between the two strands can be recognized as potential sites of biologically-derived mismatches in the original double stranded target nucleic acid molecule. Alternatively, in some embodiments, sites of sequence disagreement between the two strands can be recognized as potential sites of DNA synthesis-derived mismatches in the original double stranded target nucleic acid molecule. Alternatively, in some embodiments, sites of sequence disagreement between the two strands can be recognized as potential sites where a damaged or modified nucleotide base was present on one or both strands and was converted to a mismatch by an enzymatic process (for example a DNA polymerase, a DNA glycosylase or another nucleic acid modifying enzyme or chemical process). In some embodiments, this latter finding can be used to infer the presence of nucleic acid damage or nucleotide modification prior to the enzymatic process or chemical treatment.

In some embodiments, and in accordance with aspects of the present technology, sequencing reads generated from the Duplex Sequencing steps discussed herein can be further filtered to eliminate sequencing reads from DNA-damaged molecules (e.g., damaged during storage, shipping, during or following tissue or blood extraction, during or following library preparation, etc.). For example, DNA repair enzymes, such as Uracil-DNA Glycosylase (UDG), Formamidopyrimidine DNA glycosylase (FPG), and 8-oxoguanine DNA glycosylase (OGG1), can be utilized to eliminate or correct DNA damage (e.g., in vitro DNA damage or in vivo damage). These DNA repair enzymes, for example, are glycoslyases that remove damaged bases from DNA. For example, UDG removes uracil that results from cytosine deamination (caused by spontaneous hydrolysis of cytosine) and FPG removes 8-oxo-guanine (e.g., a common DNA lesion that results from reactive oxygen species). FPG also has lyase activity that can generate a 1 base gap at abasic sites. Such abasic sites will generally subsequently fail to amplify by PCR, for example, because the polymerase fails to copy the template. Accordingly, the use of such DNA damage repair/elimination enzymes can effectively remove damaged DNA that doesn't have a true mutation but might otherwise be undetected as an error following sequencing and duplex sequence analysis. Although an error due to a damaged base can often be corrected by Duplex Sequencing, in rare cases a complementary error could theoretically occur at the same position on both strands; thus, reducing error-increasing damage can reduce the probability of artifacts. Furthermore, during library preparation, certain fragments of DNA to be sequenced may be single-stranded from their source or from processing steps (for example, mechanical DNA shearing). These regions are typically converted to double stranded DNA during an "end repair" step known in the art, whereby a DNA polymerase and nucleoside substrates are added to a DNA sample to extend 5' recessed ends. A mutagenic site of DNA damage in the single-stranded portion of the DNA being copied (i.e. single-stranded 5' overhang at one or both ends of the DNA duplex or internal single-stranded nicks or gaps) can cause an error during the fill-in reaction that could render a single-stranded mutation, synthesis error, or site of nucleic acid damage into a double-stranded form that could be misinterpreted in the final duplex consensus sequence as a true mutation whereby the true mutation was present in the original double stranded nucleic acid molecule, when, in fact, it was not. This scenario, termed "pseudo-duplex", can be reduced or prevented by use of such damage destroying/repair enzymes. In other embodiments, this occurrence can be reduced or eliminated through use of strategies to destroy or prevent single-stranded portions of the original duplex molecule to form (e.g. use of certain enzymes being used to fragment the original double stranded nucleic acid material rather than mechanical shearing or certain other enzymes that may leave nicks or gaps). In other embodiments, use of processes to eliminate single-stranded portions of original double-stranded nucleic acids (e.g. single-stand specific nucleases such as S1 nuclease or mung bean nuclease) can be utilized for a similar purpose.

In further embodiments, sequencing reads generated from the Duplex Sequencing steps discussed herein can be further filtered to eliminate false mutations by trimming ends of the reads most prone to pseudoduplex artifacts. For example, DNA fragmentation can generate single strand portions at the terminal ends of double-stranded molecule. These single-stranded portions can be filled in (e.g., by Klenow or T4 polymerase) during end repair. In some instances, polymerases make copy mistakes in these end repaired regions leading to the generation of "pseudoduplex molecules." These artifacts of library preparation can incorrectly appear to be true mutations once sequenced. These errors, as a result of end repair mechanisms, can be eliminated or reduced from analysis post-sequencing by trimming the ends of the sequencing reads to exclude any mutations that may have occurred in higher risk regions, thereby reducing the number of false mutations. In one embodiment, such trimming of sequencing reads can be accomplished automatically (e.g., a normal process step). In another embodiment, a mutant frequency can be assessed for fragment end regions, and if a threshold level of mutations is observed in the fragment end regions, sequencing read trimming can be performed before generating a double-strand consensus sequence read of the DNA fragments.

By way of specific example, in some embodiments, provided herein are methods of generating an error-corrected sequence read of a double-stranded target nucleic acid material, including the step of ligating a double-stranded target nucleic acid material to at least one adapter sequence, to form an adapter-target nucleic acid material complex, wherein the at least one adapter sequence comprises (a) a degenerate or semi-degenerate single molecule identifier (SMI) sequence that uniquely labels each molecule of the double-stranded target nucleic acid material, and (b) a first nucleotide adapter sequence that tags a first strand of the adapter-target nucleic acid material complex, and a second nucleotide adapter sequence that is at least partially non-complimentary to the first nucleotide sequence that tags a second strand of the adapter-target nucleic acid material complex such that each strand of the adapter-target nucleic acid material complex has a distinctly identifiable nucleotide sequence relative to its complementary strand. The method can next include the steps of amplifying each strand of the adapter-target nucleic acid material complex to produce a plurality of first strand adapter-target nucleic acid complex amplicons and a plurality of second strand adapter-target nucleic acid complex amplicons. The method can further include the steps of amplifying both the first and second strands to provide a first nucleic acid product and a second nucleic acid product. The method may also include the steps of sequencing each of the first nucleic acid product and second nucleic acid product to produce a plurality of first strand sequence reads and plurality of second strand sequence reads, and confirming the presence of at least one first strand sequence read and at least one second strand sequence read. The method may further include comparing the at least one first strand sequence read with the at least one second strand sequence read, and generating an error-corrected sequence read of the double-stranded target nucleic acid material by discounting nucleotide positions that do not agree, or alternatively removing compared first and second strand sequence reads having one or more nucleotide positions where the compared first and second strand sequence reads are non-complementary.

By way of an additional specific example, in some embodiments, provided herein are methods of identifying a DNA variant from a sample including the steps of ligating both strands of a nucleic acid material (e.g., a double-stranded target DNA molecule) to at least one asymmetric adapter molecule to form an adapter-target nucleic acid material complex having a first nucleotide sequence associated with a first strand of a double-stranded target DNA molecule (e.g., a top strand) and a second nucleotide sequence that is at least partially non-complementary to the first nucleotide sequence associated with a second strand of the double-stranded target DNA molecule (e.g., a bottom strand), and amplifying each strand of the adapter-target nucleic acid material, resulting in each strand generating a distinct, yet related, set of amplified adapter-target nucleic acid products. The method can further include the steps of sequencing each of a plurality of first strand adapter-target nucleic acid products and a plurality of second strand adapter-target nucleic acid products, confirming the presence of at least one amplified sequence read from each strand of the adapter-target nucleic acid material complex, and comparing the at least one amplified sequence read obtained from the first strand with the at least one amplified sequence read obtained from the second strand to form a consensus sequence read of the nucleic acid material (e.g., a double-stranded target DNA molecule) having only nucleotide bases at which the sequence of both strands of the nucleic acid material (e.g., a double-stranded target DNA molecule) are in agreement, such that a variant occurring at a particular position in the consensus sequence read (e.g., as compared to a reference sequence) is identified as a true DNA variant.

In some embodiments, provided herein are methods of generating a high accuracy consensus sequence from a double-stranded nucleic acid material, including the steps of tagging individual duplex DNA molecules with an adapter molecule to form tagged DNA material, wherein each adapter molecule comprises (a) a degenerate or semi-degenerate single molecule identifier (SMI) that uniquely labels the duplex DNA molecule, and (b) first and second non-complementary nucleotide adapter sequences that distinguishes an original top strand from an original bottom strand of each individual DNA molecule within the tagged DNA material, for each tagged DNA molecule, and generating a set of duplicates of the original top strand of the tagged DNA molecule and a set of duplicates of the original bottom strand of the tagged DNA molecule to form amplified DNA material. The method can further include the steps of creating a first single strand consensus sequence (SSCS) from the duplicates of the original top strand and a second single strand consensus sequence (SSCS) from the duplicates of the original bottom strand, comparing the first SSCS of the original top strand to the second SSCS of the original bottom strand, and generating a high-accuracy consensus sequence having only nucleotide bases at which the sequence of both the first SSCS of the original top strand and the second SSCS of the original bottom strand are complimentary.

In further embodiments, provided herein are methods of detecting and/or quantifying DNA mutations and/or variants from a sample comprising double-stranded target DNA molecules including the steps of ligating both strands of each double-stranded target DNA molecule to at least one asymmetric adapter molecule to form a plurality of adapter-target DNA complexes, wherein each adapter-target DNA complex has a first nucleotide sequence associated with a first strand of a double-stranded target DNA molecule and a second nucleotide sequence that is at least partially non-complementary to the first nucleotide sequence associated with a second strand of the double-stranded target DNA molecule, and for each adapter target DNA complex: amplifying each strand of the adapter-target DNA complex, resulting in each strand generating a distinct, yet related, set of amplified adapter-target DNA amplicons. The method can further include the steps of sequencing each of a plurality of first strand adapter-target DNA amplicons and a plurality of second strand adapter-target DNA amplicons, confirming the presence of at least one sequence read from each strand of the adapter-target DNA complex, and comparing the at least one sequence read obtained from the first strand with the at least one sequence read obtained from the second strand to detect and/or quantify nucleotide bases at which the sequence read of one strand of the double-stranded DNA molecule is in disagreement (e.g., non-complimentary) with the sequence read of the other strand of the double-stranded DNA molecule, such that site(s) of DNA damage can be detected and/or quantified. In some embodiments, the method can further include the steps of creating a first single strand consensus sequence (SSCS) from the first strand adapter-target DNA amplicons and a second single strand consensus sequence (SSCS) from the second strand adapter-target DNA amplicons, comparing the first SSCS of the original first strand to the second SSCS of the original second strand, and identifying nucleotide bases at which the sequence of the first SSCS and the second SSCS are non-complementary to detect and/or quantify DNA damage associated with the double-stranded target DNA molecules in the sample.

Single Molecule Identifier Sequences (SMIs)

In accordance with various embodiments, provided methods and compositions include one or more SMI sequences on each strand of a nucleic acid material. The SMI can be independently carried by each of the single strands that result from a double-stranded nucleic acid molecule such that the derivative amplification products of each strand can be recognized as having come from the same original substantially unique double-stranded nucleic acid molecule after sequencing. In some embodiments, the SMI may include additional information and/or may be used in other methods for which such molecule distinguishing functionality is useful, as will be recognized by one of skill in the art.

In some embodiments, an SMI element may be incorporated before, substantially simultaneously, or after adapter sequence ligation to a nucleic acid material.

In some embodiments, an SMI sequence may include at least one degenerate or semi-degenerate nucleic acid. In other embodiments, an SMI sequence may be non-degenerate. In some embodiments, the SMI can be the sequence associated with or near a fragment end of the nucleic acid molecule (e.g., randomly or semi-randomly sheared ends of ligated nucleic acid material). In some embodiments, an exogenous sequence may be considered in conjunction with the sequence corresponding to randomly or semi-randomly sheared ends of ligated nucleic acid material (e.g., DNA) to obtain an SMI sequence capable of distinguishing, for example, single DNA molecules from one another. In some embodiments, a SMI sequence is a portion of an adapter sequence that is ligated to a double-strand nucleic acid molecule. In certain embodiments, the adapter sequence comprising a SMI sequence is double-stranded such that each strand of the double-stranded nucleic acid molecule includes an SMI following ligation to the adapter sequence. In another embodiment, the SMI sequence is single-stranded before or after ligation to a double-stranded nucleic acid molecule and a complimentary SMI sequence can be generated by extending the opposite strand with a DNA polymerase to yield a complementary double-stranded SMI sequence. In other embodiments, an SMI sequence is in a single-stranded portion of the adapter (e.g., an arm of an adapter having a Y-shape). In such embodiments, the SMI can facilitate grouping of families of sequence reads derived from an original strand of a double-stranded nucleic acid molecule, and in some instances can confer relationship between original first and second strands of a double-stranded nucleic acid molecule (e.g., all or part of the SMIs maybe relatable via look up table). In embodiments, where the first and second strands are labeled with different SMIs, the sequence reads from the two original strands may be related using one or more of an endogenous SMI (e.g., a fragment-specific feature such as sequence associated with or near a fragment end of the nucleic acid molecule), or with use of an additional molecular tag shared by the two original strands (e.g., a barcode in a double-stranded portion of the adapter), or a combination thereof. In some embodiments, each SMI sequence may include between about 1 to about 30 nucleic acids (e.g., 1, 2, 3, 4, 5, 8, 10, 12, 14, 16, 18, 20, or more degenerate or semi-degenerate nucleic acids).

In some embodiments, a SMI is capable of being ligated to one or both of a nucleic acid material and an adapter sequence. In some embodiments, a SMI may be ligated to at least one of a T-overhang, an A-overhang, a CG-overhang, a dehydroxylated base, and a blunt end of a nucleic acid material.

In some embodiments, a sequence of a SMI may be considered in conjunction with (or designed in accordance with) the sequence corresponding to, for example, randomly or semi-randomly sheared ends of a nucleic acid material (e.g., a ligated nucleic acid material), to obtain a SMI sequence capable of distinguishing single nucleic acid molecules from one another.

In some embodiments, at least one SMI may be an endogenous SMI (e.g., an SMI related to a shear point (e.g., a fragment end), for example, using the shear point itself or using a defined number of nucleotides in the nucleic acid material immediately adjacent to the shear point [e.g., 2, 3, 4, 5, 6, 7, 8, 9, 10 nucleotides from the shear point]). In some embodiments, at least one SMI may be an exogenous SMI (e.g., an SMI comprising a sequence that is not found on a target nucleic acid material).

In some embodiments, a SMI may be or comprise an imaging moiety (e.g., a fluorescent or otherwise optically detectable moiety). In some embodiments, such SMIs allow for detection and/or quantitation without the need for an amplification step.

In some embodiments a SMI element may comprise two or more distinct SMI elements that are located at different locations on the adapter-target nucleic acid complex.

Various embodiments of SMIs are further disclosed in International Patent Publication No. WO2017/100441, which is incorporated by reference herein in its entirety.

Strand-Defining Element (SDE)

In some embodiments, each strand of a double-stranded nucleic acid material may further include an element that renders the amplification products of the two single-stranded nucleic acids that form the target double-stranded nucleic acid material substantially distinguishable from each other after sequencing. In some embodiments, a SDE may be or comprise asymmetric primer sites comprised within a sequencing adapter, or, in other arrangements, sequence asymmetries may be introduced into the adapter sequences and not within the primer sequences, such that at least one position in the nucleotide sequences of a first strand target nucleic acid sequence complex and a second stand of the target nucleic acid sequence complex are different from each other following amplification and sequencing. In other embodiments, the SDE may comprise another biochemical asymmetry between the two strands that differs from the canonical nucleotide sequences A, T, C, G or U, but is converted into at least one canonical nucleotide sequence difference in the two amplified and sequenced molecules. In yet another embodiment, the SDE may be or comprise a means of physically separating the two strands before amplification, such that derivative amplification products from the first strand target nucleic acid sequence and the second strand target nucleic acid sequence are maintained in substantial physical isolation from one another for the purposes of maintaining a distinction between the two derivative amplification products. Other such arrangements or methodologies for providing an SDE function that allows for distinguishing the first and second strands may be utilized.

In some embodiments, a SDE may be capable of forming a loop (e.g., a hairpin loop). In some embodiments, a loop may comprise at least one endonuclease recognition site. In some embodiments the target nucleic acid complex may contain an endonuclease recognition site that facilitates a cleavage event within the loop. In some embodiments, a loop may comprise a non-canonical nucleotide sequence. In some embodiments, the contained non-canonical nucleotide may be recognizable by one or more enzyme that facilitates strand cleavage. In some embodiments, the contained non-canonical nucleotide may be targeted by one or more chemical process facilitates strand cleavage in the loop. In some embodiments the loop may contain a modified nucleic acid linker that may be targeted by one or more enzymatic, chemical or physical process that facilitates strand cleavage in the loop. In some embodiments this modified linker is a photocleavable linker.

A variety of other molecular tools could serve as SMIs and SDEs. Other than shear points and DNA-based tags, single-molecule compartmentalization methods that keep paired strands in physical proximity or other non-nucleic acid tagging methods could serve the strand-relating function. Similarly, asymmetric chemical labelling of the adapter strands in a way that they can be physically separated can serve an SDE role. A recently described variation of Duplex Sequencing uses bisulfite conversion to transform naturally occurring strand asymmetries in the form of cytosine methylation into sequence differences that distinguish the two strands. Although this implementation limits the types of mutations that can be detected, the concept of capitalizing on native asymmetry is noteworthy in the context of emerging sequencing technologies that can directly detect modified nucleotides. Various embodiments of SDEs are further disclosed in International Patent Publication No. WO2017/100441, which is incorporated by reference in its entirety.

Adapters and Adapter Sequences

In various arrangements, adapter molecules that comprise SMIs (e.g., molecular barcodes), SDEs, primer sites, flow cell sequences and/or other features are contemplated for use with many of the embodiments disclosed herein. In some embodiments, provided adapters may be or comprise one or more sequences complimentary or at least partially complimentary to PCR primers (e.g., primer sites) that have at least one of the following properties: 1) high target specificity; 2) capable of being multiplexed; and 3) exhibit robust and minimally biased amplification.

In some embodiments, adapter molecules can be "Y"-shaped, "U"-shaped, "hairpin" shaped, have a bubble (e.g., a portion of sequence that is non-complimentary), or other features. In other embodiments, adapter molecules can comprise a "Y"-shape, a "U"-shaped, a "hairpin" shaped, or a bubble. Certain adapters may comprise modified or non-standard nucleotides, restriction sites, or other features for manipulation of structure or function in vitro. Adapter molecules may ligate to a variety of nucleic acid material having a terminal end. For example, adapter molecules can be suited to ligate to a T-overhang, an A-overhang, a CG-overhang, a multiple nucleotide overhang, a dehydroxylated base, a blunt end of a nucleic acid material and the end of a molecule where the 5' of the target is dephosphorylated or otherwise blocked from traditional ligation. In other embodiments the adapter molecule can contain a dephosphorylated or otherwise ligation-preventing modification on the 5' strand at the ligation site. In the latter two embodiments, such strategies may be useful for preventing dimerization of library fragments or adapter molecules.

An adapter sequence can mean a single-strand sequence, a double-strand sequence, a complimentary sequence, a non-complimentary sequence, a partial complimentary sequence, an asymmetric sequence, a primer binding sequence, a flow-cell sequence, a ligation sequence, or other sequence provided by an adapter molecule. In particular embodiments, an adapter sequence can mean a sequence used for amplification by way of compliment to an oligonucleotide.

In some embodiments, provided methods and compositions include at least one adapter sequence (e.g., two adapter sequences, one on each of the 5' and 3' ends of a nucleic acid material). In some embodiments, provided methods and compositions may comprise 2 or more adapter sequences (e.g., 3, 4, 5, 6, 7, 8, 9, 10 or more). In some embodiments, at least two of the adapter sequences differ from one another (e.g., by sequence). In some embodiments, each adapter sequence differs from each other adapter sequence (e.g., by sequence). In some embodiments, at least one adapter sequence is at least partially non-complementary to at least a portion of at least one other adapter sequence (e.g., is non-complementary by at least one nucleotide).

In some embodiments, an adapter sequence comprises at least one non-standard nucleotide. In some embodiments, a non-standard nucleotide is selected from an abasic site, a uracil, tetrahydrofuran, 8-oxo-7,8-dihydro-2'deoxyadenosine (8-oxo-A), 8-oxo-7,8-dihydro-2'-deoxyguanosine (8-oxo-G), deoxyinosine, 5'nitroindole, 5-Hydroxymethyl-2'-deoxycytidine, iso-cytosine, 5'-methyl-isocytosine, or isoguanosine, a methylated nucleotide, an RNA nucleotide, a ribose nucleotide, an 8-oxo-guanine, a photocleavable linker, a biotinylated nucleotide, a desthiobiotin nucleotide, a thiol modified nucleotide, an acrydite modified nucleotide an iso-dC, an iso dG, a 2'-O-methyl nucleotide, an inosine nucleotide Locked Nucleic Acid, a peptide nucleic acid, a 5 methyl dC, a 5-bromo deoxyuridine, a 2,6-Diaminopurine, 2-Aminopurine nucleotide, an abasic nucleotide, a 5-Nitroindole nucleotide, an adenylated nucleotide, an azide nucleotide, a digoxigenin nucleotide, an I-linker, an 5' Hexynyl modified nucleotide, an 5-Octadiynyl dU, photocleavable spacer, a non-photocleavable spacer, a click chemistry compatible modified nucleotide, and any combination thereof.

In some embodiments, an adapter sequence comprises a moiety having a magnetic property (i.e., a magnetic moiety). In some embodiments this magnetic property is paramagnetic. In some embodiments where an adapter sequence comprises a magnetic moiety (e.g., a nucleic acid material ligated to an adapter sequence comprising a magnetic moiety), when a magnetic field is applied, an adapter sequence comprising a magnetic moiety is substantially separated from adapter sequences that do not comprise a magnetic moiety (e.g., a nucleic acid material ligated to an adapter sequence that does not comprise a magnetic moiety).

In some embodiments, at least one adapter sequence is located 5' to a SMI. In some embodiments, at least one adapter sequence is located 3' to a SMI.

In some embodiments, an adapter sequence may be linked to at least one of a SMI and a nucleic acid material via one or more linker domains. In some embodiments, a linker domain may be comprised of nucleotides. In some embodiments, a linker domain may include at least one modified nucleotide or non-nucleotide molecules (for example, as described elsewhere in this disclosure). In some embodiments, a linker domain may be or comprise a loop.

In some embodiments, an adapter sequence on either or both ends of each strand of a double-stranded nucleic acid material may further include one or more elements that provide a SDE. In some embodiments, a SDE may be or comprise asymmetric primer sites comprised within the adapter sequences.

In some embodiments, an adapter sequence may be or comprise at least one SDE and at least one ligation domain (i.e., a domain amendable to the activity of at least one ligase, for example, a domain suitable to ligating to a nucleic acid material through the activity of a ligase). In some embodiments, from 5' to 3', an adapter sequence may be or comprise a primer binding site, a SDE, and a ligation domain.

Various methods for synthesizing Duplex Sequencing adapters have been previously described in, e.g., ET.S. Patent No. 9,752,188, International Patent Publication No. WO2017/100441, and International Patent Application No. PCT/US 18/59908 (filed Nov. 8, 2018), all of which are incorporated by reference herein in their entireties.

Primers

In some embodiments, one or more PCR primers that have at least one of the following properties: 1) high target specificity; 2) capable of being multiplexed; and 3) exhibit robust and minimally biased amplification are contemplated for use in various embodiments in accordance with aspects of the present technology. A number of prior studies and commercial products have designed primer mixtures satisfying a certain number of these criteria for conventional PCR-CE. However, it has been noted that these primer mixtures are not always optimal for use with MPS. Indeed, developing highly multiplexed primer mixtures can be a challenging and time-consuming process. Conveniently, both Illumina and Promega have recently developed multiplex compatible primer mixtures for the Illumina platform that show robust and efficient amplification of a variety of standard and non-standard STR and SNP loci. Because these kits use PCR to amplify their target regions prior to sequencing, the 5'-end of each read in paired-end sequencing data corresponds to the 5'-end of the PCR primers used to amplify the DNA. In some embodiments, provided methods and compositions include primers designed to ensure uniform amplification, which may entail varying reaction concentrations, melting temperatures, and minimizing secondary structure and intra/inter-primer interactions. Many techniques have been described for highly multiplexed primer optimization for MPS applications. In particular, these techniques are often known as ampliseq methods, as well described in the art.

Amplification

Provided methods and compositions, in various embodiments, make use of, or are of use in, at least one amplification step wherein a nucleic acid material (or portion thereof, for example, a specific target region or locus) is amplified to form an amplified nucleic acid material (e.g., some number of amplicon products).

In some embodiments, amplifying a nucleic acid material includes a step of amplifying nucleic acid material derived from each of a first and second nucleic acid strand from an original double-stranded nucleic acid material using at least one single-stranded oligonucleotide at least partially complementary to a sequence present in a first adapter sequence such that a SMI sequence is at least partially maintained. An amplification step further includes employing a second single-stranded oligonucleotide to amplify each strand of interest, and such second single-stranded oligonucleotide can be (a) at least partially complementary to a target sequence of interest, or (b) at least partially complementary to a sequence present in a second adapter sequence such that the at least one single-stranded oligonucleotide and a second single-stranded oligonucleotide are oriented in a manner to effectively amplify the nucleic acid material.

In some embodiments, amplifying nucleic acid material in a sample can include amplifying nucleic acid material in "tubes" (e.g., PCR tubes), in emulsion droplets, microchambers, and other examples described above or other known vessels.

In some embodiments, at least one amplifying step includes at least one primer that is or comprises at least one non-standard nucleotide. In some embodiments, a non-standard nucleotide is selected from a uracil, a methylated nucleotide, an RNA nucleotide, a ribose nucleotide, an 8-oxo-guanine, a biotinylated nucleotide, a locked nucleic acid, a peptide nucleic acid, a high-Tm nucleic acid variant, an allele discriminating nucleic acid variant, any other nucleotide or linker variant described elsewhere herein and any combination thereof.

While any application-appropriate amplification reaction is contemplated as compatible with some embodiments, by way of specific example, in some embodiments, an amplification step may be or comprise a polymerase chain reaction (PCR), rolling circle amplification (RCA), multiple displacement amplification (MDA), isothermal amplification, polony amplification within an emulsion, bridge amplification on a surface, the surface of a bead or within a hydrogel, and any combination thereof.

In some embodiments, amplifying a nucleic acid material includes use of single-stranded oligonucleotides at least partially complementary to regions of the adapter sequences on the 5' and 3' ends of each strand of the nucleic acid material. In some embodiments, amplifying a nucleic acid material includes use of at least one single-stranded oligonucleotide at least partially complementary to a target region or a target sequence of interest (e.g., a genomic sequence, a mitochondrial sequence, a plasmid sequence, a synthetically produced target nucleic acid, etc.) and a single-stranded oligonucleotide at least partially complementary to a region of the adapter sequence (e.g., a primer site).

In general, robust amplification (for example PCR amplification), can be highly dependent on the reaction conditions. Multiplex PCR, for example, can be sensitive to buffer composition, monovalent or divalent cation concentration, detergent concentration, crowding agent (i.e. PEG, glycerol, etc.) concentration, primer concentrations, primer Tms, primer designs, primer GC content, primer modified nucleotide properties, and cycling conditions {i.e. temperature and extension times and rate of temperature changes). Optimization of buffer conditions can be a difficult and time-consuming process. In some embodiments, an amplification reaction may use at least one of a buffer, primer pool concentration, and PCR conditions in accordance with a previously known amplification protocol. In some embodiments, a new amplification protocol may be created, and/or an amplification reaction optimization may be used. By way of specific example, in some embodiments, a PCR optimization kit may be used, such as a PCR Optimization Kit from Promega®, which contains a number of pre-formulated buffers that are partially optimized for a variety of PCR applications, such as multiplex, real-time, GC-rich, and inhibitor-resistant amplifications. These pre-formulated buffers can be rapidly supplemented with different $Mg^{2+}$ and primer concentrations, as well as primer pool ratios. In addition, in some embodiments, a variety of cycling conditions (e.g., thermal cycling) may be assessed and/or used. In assessing whether or not a particular embodiment is appropriate for a particular desired application, one or more of specificity, allele coverage ratio for heterozygous loci, inter-locus balance, and depth, among other aspects, may be assessed. Measurements of amplification success may include DNA sequencing of the products, evaluation of products by gel or capillary electrophoresis or HPLC or other size separation methods followed by fragment visualization, melt curve analysis using double-stranded nucleic acid binding dyes or fluorescent probes, mass spectrometry or other methods known in the art.

In accordance with various embodiments, any of a variety of factors may influence the length of a particular amplification step (e.g., the number of cycles in a PCR reaction, etc.). For example, in some embodiments, a provided nucleic acid material may be compromised or otherwise suboptimal (e.g. degraded and/or contaminated). In such case, a longer amplification step may be helpful in ensuring a desired product is amplified to an acceptable degree. In some embodiments, an amplification step may provide an average of 3 to 10 sequenced PCR copies from each starting DNA molecule, though in other embodiments, only a single copy of each of a first strand and second strand are required. Without wishing to be held to a particular theory, it is possible that too many or too few PCR copies could result in reduced assay efficiency and, ultimately, reduced depth.

Generally, the number of nucleic acid (e.g., DNA) fragments used in an amplification (e.g., PCR) reaction is a primary adjustable variable that can dictate the number of reads that share the same SMI/barcode sequence.

Nucleic Acid Material

Types

In accordance with various embodiments, any of a variety of nucleic acid material may be used. In some embodiments, nucleic acid material may comprise at least one modification to a polynucleotide within the canonical sugar-phosphate backbone. In some embodiments, nucleic acid material may comprise at least one modification within any base in the nucleic acid material. For example, by way of non-limiting example, in some embodiments, the nucleic acid material is or comprises at least one of double-stranded DNA, single-stranded DNA, double-stranded RNA, single-stranded RNA, peptide nucleic acids (PNAs), locked nucleic acids (LNAs).

Modifications

In accordance with various embodiments, nucleic acid material may receive one or more modifications prior to, substantially simultaneously, or subsequent to, any particular step, depending upon the application for which a particular provided method or composition is used.

In some embodiments, a modification may be or comprise repair of at least a portion of the nucleic acid material. While any application-appropriate manner of nucleic acid repair is contemplated as compatible with some embodiments, certain exemplary methods and compositions therefore are described below and in the Examples.

By way of non-limiting example, in some embodiments, DNA repair enzymes, such as Uracil-DNA Glycosylase (UDG), Formamidopyrimidine DNA glycosylase (FPG), and 8-oxoguanine DNA glycosylase (OGG1), can be utilized to correct DNA damage (e.g., in vitro DNA damage). As discussed above, these DNA repair enzymes, for example, are glycoslyases that remove damaged bases from DNA. For example, UDG removes uracil that results from cytosine deamination (caused by spontaneous hydrolysis of cytosine) and FPG removes 8-oxo-guanine (e.g., most common DNA lesion that results from reactive oxygen species). FPG also has lyase activity that can generate 1 base gap at abasic sites. Such abasic sites will subsequently fail to amplify by PCR, for example, because the polymerase fails copy the template. Accordingly, the use of such DNA damage repair enzymes can effectively remove damaged DNA that doesn't have a true mutation but might otherwise be undetected as an error following sequencing and duplex sequence analysis.

As discussed above, in further embodiments, sequencing reads generated from the processing steps discussed herein can be further filtered to eliminate false mutations by trimming ends of the reads most prone to artifacts. For example, DNA fragmentation can generate single-strand portions at the terminal ends of double-stranded molecules. These single-stranded portions can be filled in (e.g., by Klenow) during end repair. In some instances, polymerases make copy mistakes in these end-repaired regions leading to the generation of "pseudoduplex molecules." These artifacts can appear to be true mutations once sequenced. These errors, as a result of end repair mechanisms, can be eliminated from analysis post-sequencing by trimming the ends of the sequencing reads to exclude any mutations that may have occurred, thereby reducing the number of false mutations. In some embodiments, such trimming of sequencing reads can be accomplished automatically (e.g., a normal process step). In some embodiments, a mutant frequency can be assessed for fragment end regions and if a threshold level of mutations is observed in the fragment end regions, sequencing read trimming can be performed before generating a double-strand consensus sequence read of the DNA fragments.

The high degree of error correction provided by the strand-comparison technology of Duplex Sequencing reduces sequencing errors of double-stranded nucleic acid molecules by multiple orders of magnitude as compared with standard next-generation sequencing methods. This reduction in errors improves the accuracy of sequencing in nearly all types of sequences but can be particularly well suited to biochemically challenging sequences that are well known in the art to be particularly error prone. One non-limiting example of such type of sequence is homopolymers or other microsatellites/short-tandem repeats. Another non-limiting example of error prone sequences that benefit from Duplex Sequencing error correction are molecules that have been damaged, for example, by heating, radiation, mechanical stress, or a variety of chemical exposures which creates chemical adducts that are error prone during copying by one or more nucleotide polymerases and also those that create single-stranded DNA at ends of molecules or as nicks and gaps. In further embodiments, Duplex Sequencing can also be used for the accurate detection of minority sequence variants among a population of double-stranded nucleic acid molecules. One non-limiting example of this application is detection of a small number of variant DNA molecules (e.g., with variants that were induced, acquired, and/or selected for during a genome editing event), among a larger number of DNA molecules. Another non-limiting application for rare variant detection by Duplex Sequencing is early detection of DNA damage resulting from a genomic editing event. A further non-limiting application of Duplex Sequencing is for detection and quantification of clonal expansion of cells (e.g., cells with a positive growth bias, e.g., cells containing mutations under selective pressure, e.g., neoplastic mutations). Another non-limiting application of Duplex Sequencing is for assessing success of target genome editing activities or detection of aberrant genome editing events.

Selected Embodiments for Assessment of Genomic Editing

Genome editing, also known as gene editing and engineered genome editing, among other names, is widely used in applications such as gene silencing or transcriptional repression, transient activation of endogenous genes, genetic modification of embryonic stem cells, production of cell therapies to treat disease, generation of transgenic organisms, genetic engineering of plants for crop improvement among other agriculture applications, and in vivo gene knockout screening, destruction of dominant-negative genetic loci, among other uses. Depending on the intended applications, genome editing techniques can be effective for inserting, deleting, modifying, replacing, correcting, or mutating nucleic acid sequence(s) in the genome of the living organism. In particular applications, precise modifications to a genomic sequence (either intended or not intended, desired or not desired) can be ascertained using genome editing.

Characterization of the genome following a genome editing process can be important to determine if a desired change at a targeted (e.g., an intended genomic site) region or locus of the DNA was achieved, to determine the efficiency of the process (e.g., to determine the proportion of cells that were accurately altered at the intended genomic site), and to assess if any changes were made to the genome of cells at one or more unintended or "off-target" loci of the genome. Genome sequencing methods (e.g., NGS) provide a tool for determining the nucleotide sequence at one or more sites of the genome; however, the level of sensitivity of accuracy of DNA sequencing needed to identify and quantify gene editing events in a cell population on a molecule-by-molecule basis is not achievable with conventional NGS methods. Duplex Sequencing, as described, herein provides the level of sensitivity and sequencing error-correction needed to effectively characterize and determine the success (and suitability and safety) of a genome editing event, method, or reagent for an intended application.

In addition to determining the genomic alterations occurring in cells in a cell population following a genomic editing event, such genomic alterations can create selective pressure on one or more cells in the cell population that can cause cells to either have a positive growth bias or negative growth bias with respect to other cells in the cell population. Such growth bias can result in clonal expansion of cells comprising such growth advantages (in comparison to other cells in the cell population). Aspects of the present disclosure are directed to assessment of clonal expansion, and in particular, assessment of neoplastic potential of such cells.

Selected Examples of Duplex Sequencing Methods for Genome Editing Characterization The present disclosure provides methods useful for characterizing genomic editing events and/or cell populations following a genome editing event. The present disclosure encompasses a recognition that highly accurate sequencing methods, such as Duplex Sequencing methods described above, may enable high resolution characterization of cells that have undergone genome editing. The present disclosure provides methods for characterization of the accuracy of the genomic editing event, as well as methods assessing characteristics of a cell population over time (e.g., over a period of culturing the cells and/or over a period of treatment with the cells), such as determining if there is clonal expansion of particular cells in a cell population.

The present disclosure provides methods of characterizing cells following a genome editing event, e.g., an engineered genome editing event. It is important to be able to accurately detect incorrect genome editing events and/or off-target variations resulting from genome editing. For example, imperfect specificity of engineered site-specific binding can lead to unintended insertion, modification or deletion of genomic loci during a genomic editing event. The consequences of such off target or aberrant genomic alterations can have clinical consequences. It is similarly important to be able to characterize the distribution of types of genomic editing events that occur at one or more intended loci in a population of molecules—for example, after cleavage by a targeted ribonucleoprotein such as Cas9, error-prone non-homologous end joining can lead to a variety of different length deletion, insertion or other mutational events.

In some embodiments, provided methods are useful for assessing if a genomic editing event (e.g., an engineered genomic editing event directed to an intended genomic locus) proceeded correctly. In some embodiments, provided methods are useful for assessing if one or more unintended mutations are introduced during a genomic editing event. In some embodiments, provided methods can be used to determine if mutations (e.g., happening in a small number of cells among a population of cells) are introduced or if an incorrect genome editing event took place in one or more cells of a population. In some embodiments provided methods can be used to characterize the distribution of types of genomic editing events that occur at one or more intended loci in a population of molecules.

In some embodiments are provided methods of characterizing a population of cells following a genomic editing event (e.g., an engineered genomic editing event directed to an intended genomic locus), such methods generally include a step of providing a sample that includes a population of double-stranded DNA molecules. Such double-stranded DNA molecules can be extracted or originate from a population of cells to be analyzed (e.g., a population of cells that have undergone a genome editing event, e.g., an engineered genomic editing event.) In some embodiments double-stranded DNA molecules can be isolated from non-cellular DNA, such as cell-free DNA of DNA from exosomes or other extracellular vesicles from a population of cells to be analyzed. In some embodiments, provided methods include using Duplex Sequence to generate error-corrected sequence reads of the original double-stranded DNA molecules by comparing at least one first strand sequence read and at least one second strand sequence read to identify one or more correspondences between the first and second strand sequence reads. In a particular example, nucleotide positions that are in agreement between the first and second strand sequence reads can be identified as accurate nucleotide base calls.

In some embodiments are provided methods of generating high accuracy sequencing reads of a population of target double-stranded nucleic acid molecules extracted from a genome-edited cell population. Such methods include Duplex Sequencing of one or more target double-stranded nucleic acid molecules extracted from a cell population, and generating high accuracy consensus sequences for the targeted double-stranded DNA molecules. In some embodiments, target double-stranded nucleic acid molecules comprise an intended genome edited region of DNA and one or more unintended genomic regions of DNA.

In some embodiments, provided methods further include comparing one or more error-corrected sequence reads comprising a sequence at an intended genomic locus to an anticipated genome edited DNA sequence; and/or comparing one or more error-corrected sequence reads comprising a sequence at an unintended genomic locus to a reference genome DNA sequence.

In some embodiments, the generation of an error-corrected sequence read for each of a plurality of the double-stranded DNA molecules further comprises selectively enriching one or more targeted genomic regions prior to sequencing to provide a plurality of enriched adapter-DNA molecules. In some embodiments, provided methods are useful for identifying one or more variants among double-stranded DNA molecules of a cell population (e.g., double-stranded DNA molecules that originated and/or were extracted from a cell population that has undergone a genome editing event). In some embodiments, provided methods include a step of identifying one or more variants among double-stranded DNA molecules of a cell population.

In some embodiments, one or more targeted genomic regions to be analyzed by Duplex Sequencing methods are or include an intended genomic locus (i.e., an intended locus for genomic editing) in the genome. In some embodiments, provided methods include a step of determining if one or more error-corrected sequence reads comprises the anticipated edited DNA sequence at the intended genomic locus. Thus, provided methods may be useful for assessing the success of the genomic editing event.

In some embodiments, provided herein are methods for assessing success and/or an efficiency of obtaining a desired outcome of an engineered genome editing event. In some embodiments, provided methods comprise a step of determining a frequency of the anticipated genome edited DNA sequence among the error-corrected sequence reads comprising the sequence at the intended genomic locus.

In some embodiments, provided herein are methods for assessing accuracy of an engineered genome editing event that includes introducing a DNA sequence (e.g., a portion of a coding sequence gene, a portion of a non-coding sequence of a gene, a gene, etc.) into the genomes of cells of the population. In some embodiments, provided herein are methods for assessing accuracy of an engineered genome editing event that includes deleting a DNA sequence (e.g., a portion of a coding sequence gene, a portion of a non-coding sequence of a gene, a gene, etc.) from the genomes of cells of the population. In some embodiments, an introduced and/or deleted gene encodes a functional RNA or polypeptide.

In some embodiments, provided herein are methods for characterizing an efficiency of an engineered genomic editing event in a cell population, wherein the engineered genomic editing event is targeted to an intended genomic locus. In some embodiments, such methods include Duplex Sequencing. For example, in some embodiments, provided methods include preparing a sequencing library from a sample comprising a plurality of double-stranded DNA molecules originating from the cell population following a genomic editing event, where preparing the sequence library comprises ligating asymmetric adapter molecules to the plurality of double-stranded DNA molecules to generate a plurality of adapter-DNA molecules; sequencing first and second strands of the adapter-DNA molecules to provide a first strand sequence read and a second strand sequence read for at least a portion of the adapter-DNA molecules; and for each sequenced adapter-DNA molecule, comparing the first strand sequence read and the second strand sequence read to identify one or more correspondences between the first and second strand sequences reads. In some embodiments, provided methods include determining a frequency of an anticipated genomic sequence at the intended genomic locus among the plurality of double-stranded DNA molecules comprising the intended genomic locus. In some embodiments, a frequency of an anticipated genomic sequence at the intended genomic locus is determined by analyzing the one or more correspondences between the first and second strand sequence reads and comparing the correspondences to the anticipated genomic sequence.

In some embodiments, provided methods for characterizing an efficiency of an engineered genomic editing event include selectively enriching one or more targeted genomic regions prior to sequencing to provide a plurality of enriched adapter-DNA molecules. In some embodiments, provided methods include characterizing one or more targeted genomic regions. In some embodiments, one or more targeted genomic regions include an intended genomic locus in the genome; at least one unintended genomic locus in the genome; or both an intended and unintended genomic locus.

In some embodiments, provided herein are methods for determining if DNA was successfully genome-edited at an intended genetic locus using an engineered targeted genomic editing event. Such methods can include steps of: providing duplex error-corrected sequencing reads for a plurality of double-stranded DNA molecules extracted from a sample following the engineered targeted genomic editing event; and for each genetic locus in a set of one or more genetic loci in a reference genome, quantifying the double-stranded DNA molecules for which the duplex error-corrected sequencing reads have sequences substantially the same as an expected sequence.

In some embodiments, provided methods include analyzing the one or more correspondences between first and second strand sequence reads derived from double-stranded DNA molecules comprising sequences from one or more unintended genomic loci; and comparing the correspondences to a reference genome sequence; and determining the frequency of the one or more variants among the plurality of double-stranded DNA molecules comprising the one or more unintended genomic loci. In general, an expected sequence (e.g., reference sequences) can be used to identify an incorrect editing event or mutation, or in other embodiments an "off-target" editing event that may have occurred elsewhere in the genome (e.g., an unintended genomic locus). In some embodiments, provided methods can be used to identify an unaltered sequence (e.g., a genome that has not been successfully edited).

In some embodiments, provided herein are methods for detecting and/or quantifying incidences where a genomic editing event was unsuccessful (e.g., wherein an intended genomic locus comprises an unaltered sequence, wherein an intended genomic locus comprises an undesired or nonintentional altered sequence, wherein an unintended genomic locus comprises an altered sequence as a result of the genomic editing event). In some embodiments, provided herein are methods for assessing a proportion of unedited cells in a population. For example, a portion of cells in the population of cells having undergone a genome editing event may remain unaltered at the intended genomic locus. Determining an efficiency of the genomic editing event may include determining a proportion of original double-stranded DNA molecules comprising the sequence at the intended genomic locus that remain unaltered. Likewise, methods may include quantifying the number or proportion of original double-stranded DNA molecules comprising the desired altered sequence at the intended genomic locus.

In some embodiments, provided herein are methods for detecting and/or quantifying incidences where an engineered genome editing event was incorrect. In some embodiments, provided methods include detecting and/or quantifying the presence of one or more variants in the sequence of an intended genomic locus. In some embodiments, one or more variants include an incorrect mutation in the sequence of the intended genomic locus. For example, in some embodiments, an incorrect mutation in the sequence of the intended genomic locus for genomic editing is due to a non-homologous end joining (NHEJ) event. In some embodiments the mutation caused by NHEJ is desired and is an intended mutation. In some embodiments, provided methods include determining a frequency of an undesired DNA sequence among the error-corrected sequence reads comprising the sequence at the intended genomic locus.

In some embodiments, an engineered genomic editing event is directed to a plurality of intended genomic loci (e.g., multiplex genome engineering). In some embodiments, provided herein are methods for characterizing a plurality of genomic loci that are targeted by genome editing. In some embodiments, provided herein are methods for assessing success of engineered genome editing at two or more intended loci (e.g., 2, 3, 4, 5, 6, 7 or more). In some embodiments, provided herein are methods for detecting and/or quantifying incidences where at least one of a plurality of genome editing events were unsuccessful or incorrect.

In some embodiments, provided methods may also include a step of determining if one or more error-corrected sequence reads comprising the sequence at the unintended genomic locus comprises a variant.

In some embodiments, one or more targeted genomic regions to be analyzed by duplex sequencing methods are or include at least one unintended genomic locus in the genome. In some embodiments, one or more variants are identified in one or more error-corrected sequence reads comprising a sequence at an unintended genomic locus. Such variants may comprise a functionally disruptive mutation (e.g., such as one that disrupts protein function and has the potential to cause cancer).

In some embodiments, provided methods include a step of determining a frequency of the one or more variants at an unintended genomic locus, among the plurality of double stranded DNA molecules. In some embodiments, provided methods include a step of determining a frequency of the one or more variants at a plurality of (e.g., two or more) different unintended genomic loci. In some embodiments, such a comparison of error-corrected sequence reads can include comparing sequences at a plurality of unintended genomic loci to a reference genome DNA sequence.

In some embodiments, unintended genomic loci comprise one or more of a mutation-prone site, a microsatellite locus, a sequence with sequence homology to the intended genomic locus, and/or a cancer driver.

In some embodiments, an unintended locus is or comprises a sequence that is a mutation-prone site within the genome.

In some embodiments, an unintended locus is or comprises a sequence that is a microsatellite locus. Generally, microsatellites are short repetitive DNA sequences, which are prone to errors or mutations. In neoplastic cells, a microsatellite mutation may lead to shortening or lengthening of microsatellite sequences, thereby causing microsatellite instability (microsatellite instability, MSI).

In some embodiments, an unintended locus is or comprises a sequence that is at least partially similar to the sequence at the intended genomic locus. In some embodiments, an unintended locus is or comprises a sequence with homology to an intended genomic for editing. In some embodiments an unintended locus comprises a sequence with at least 80%, at least 85%, at least 90%, at least 91%, at least 92%, at least 93%, at least 94%, at least 95%, at least 96%, at least 97%, at least 98%, or at least 99% similarity with at least a portion of an intended genomic locus for editing. In some embodiments an unintended locus comprises a sequence with at least 80%, at least 85%, at least 90%, at least 91%, at least 92%, at least 93%, at least 94%, at least 95%, at least 96%, at least 97%, at least 98%, at least 99%, or 100% identity with at least a portion of an intended genomic locus for editing. In some embodiments, at least a portion of an intended genomic locus is at least 10 bases, at least 15 bases, at least 20 bases, at least 25 bases, at least 30 bases, at least 40 bases, at least 50 bases, or more. In some embodiments, an unintended locus comprises a sequence with at least 80%, at least 85%, at least 90%, at least 91%, at least 92%, at least 93%, at least 94%, at least 95%, at least 96%, at least 97%. at least 98%, or at least 99% similarity to a sequence of a guide polynucleotide (e.g., a synthetic guide RNA (gRNA) molecule) used in a genome editing process. In some embodiments, an unintended locus comprises a sequence with at least 80%, at least 85%, at least 90%, at least 91%, at least 92%, at least 93%, at least 94%, at least 95%, at least 96%, at least 97%. at least 98%, or at least 99% identity to a sequence of a guide polynucleotide (e.g., a synthetic guide RNA (gRNA) molecule) used in a genome editing process.

In some embodiments, an unintended locus is or comprises a tumor suppressor gene, an oncogene, a proto-oncogene, and/or a cancer driver. In some embodiments, a cancer driver is a known cancer driver from Cancer Gene Census (CGC) or the COSMIC database (genes causally implicated in cancer). In some embodiments, a cancer driver gene is or includes: ABL, ACC, BCR BLCA, BRCA, CESC, CHOL, COAD, DLBC, DNMT3A, EGFR, ESCA, GBM, HNSC, RICH, KIRC, K1RP, LAML, LGG, LIHC, LUAD, LUSC, MESO, OV, PAAD, PCPG, PI3K, PIK3CA, PRAD, PTEN READ, SARC, SKCM, STAD, TGCT, THCA, THYM, UCEC, UCS, and/or UVM. In some embodiments, a cancer driver gene is or includes TP53. In some embodiments, a cancer driver gene is or includes HRAS, NRAS, or KRAS.

In some embodiments, if a variant is detected in one or more cancer drivers among the plurality of enriched tagged DNA molecules in the population of molecules, then the method may further include a step of determining a variant frequency of the variant among the plurality of enriched tagged DNA molecules.

Selected Examples of Duplex Sequencing Methods for Assessing Clonal Selection and Clonal Expansion The ability to detect and quantify clonal expansion of cells containing mutations under selective pressure can be important for assessing cancer risk, identifying carcinogens and predicting the impact of exposure in humans, determining the success of clinical therapies, determining the success of targeted genome editing, etc. However, current tools are slow, cumbersome and/or limited in the information that they provide. Many tools lack the sensitivity to detect early stage neoplastic expansion of a clone selected under pressure.

Many events can result in alterations in the cellular genome such as insertions, deletions, breaks and/or rearrangements, that can lead to cancer if the damage does not immediately lead to cell death. In certain cell populations, cells harboring mutations in cancer driver genes (e.g., tumor suppressor genes or proto-oncogenes) may be masked by the context of the cell population and clonal growth of neighboring cells. However, an event that may disrupt clonal growth of some cells (e.g., deleterious DNA damage that causes cell cycle arrest, cell death, etc.), provides opportunity for selective growth of cells with growth advantages and such clones may disproportionately populate through cell expansion following the event. Events causing selective pressure can be any event, change, treatment, process or other exposure (chemical, biological, physical) that provides evolutionary pressure on cells that can adapt and/or outcompete neighbors. Such selective pressure can be present in vivo or in vitro settings. For example, a xenograft in a human or animal subject may demonstrate selective expansion of some cells over others. In another example, following targeted genomic editing, some cells harboring evolutionary advantages may outcompete other neighboring cells in cell culture. In such cases, the variant allele frequency of the cell clones as they expand can represent the respective rates of growth and provide insight into the selective advantage or disadvantage of the different variants represented. Accordingly, variant allele frequency of representative molecules as detected by Duplex Sequencing can be used to uncover cell clones carrying mutations that outperform other cells under selective pressures. Certain of these mutations would be problematic in clinical settings and therapies where cells would be introduced into a patient.

In some embodiments, provided methods are performed at multiple time points to assess changes in the frequency and/or abundance of one or more variants. In some embodiments, provided methods are performed at a first time point and at a second, later time point. In some embodiments, a second time point is at least 2, 3, 4, 5, 6, 7, 10, 15, 20, 30, 60, 90, or 180 days after a first time point. In some embodiments, both the first and second time points are within about 30 days, within about 45 days, within about 60 days, within about 75 days, or within about 90 days following the engineered genomic editing event. Analysis at multiple time points may be useful for assessing neoplastic potential or an increase in neoplastic potential. For example, a cell population is determined to have neoplastic potential if the variant frequency from the second time point is greater than the variant frequency from the first time point.

In some embodiments, provided methods are performed at multiple time points to assess changes in the frequency and/or abundance of one or more variants. In some embodiments, provided methods include detection and/or quantification of variants in one or more cancer drivers among the plurality of enriched tagged DNA molecules. In some embodiments, provided methods include a step of determining a variant frequency of the variant among the plurality of enriched tagged DNA molecules at a first time point and also at a later, second time point.

In some embodiments a first time point is before a genomic editing step and a second time point is after a genomic editing step. In some embodiments, provided methods include detection and/or quantification of variants in one or more cancer drivers among the plurality of enriched tagged DNA molecules, and determining a variant frequency of the variant among the plurality of enriched tagged DNA molecules.

Genome Editing

While the methods provided refer to "genome editing", it is to be understood that "genome editing" as disclosed herein, includes in vivo editing (e.g., mis-repair, insertion, or other target site alteration) of any DNA molecule targeted within the host cell or a membrane-bound piece of double-stranded DNA, for example, a native chromosome, a synthetic chromosome, a naturally-occurring or synthetic episomal molecule, a viral construct etc. In some embodiments, a genome editing activity is engineered or natural. For example, the CRISPR (Clustered Regularly Interspaced Short Palindromic Repeats)/Cas (CRISPR-associated) system evolved in bacteria and archaea as an adaptive immune system to defend against viral attack. Natural genomic editing can be mediated by viruses or viral elements, transposable or mobile genetic elements, etc. Mobile genetic elements are interacting genetic agents that replicate by either cut and paste (DNA transposons; class II elements) or copy and paste (retroposons; class I elements) processes. Mobile genetic elements are generally flanked by repeat sequences.

In some embodiments, a genome editing activity is engineered. In some embodiments, an engineered genome editing event uses a targeted endonuclease. Exemplary targeted endonucleases and methods of using the same are provided below. In some embodiments, an engineered genomic editing event is a polynucleotide substrate-mediated homologous recombination event. In some embodiments, an engineered genomic editing event introduces DNA breaks, DNA adducts, DNA oxidative damage, other forms of DNA damage, DNA nicks, DNA deamination. In dome embodiments genetic changes are introduced by a combination of cleavage with a targeted endonuclease and homologous recombination with a provided recombination template with a variant to be introduced via homologous recombination. In some embodiments, an engineered genomic editing event is carried out by a retrovirus or another virus.

Without limitation, genome editing can disrupt one or more genes or non-genic loci by insertion of a donor fragment that "knocks out" the gene or that disrupts a noncoding sequence that results in reduced expression of the gene or reduced translation into a functional protein. Alternatively, or in addition, genome editing can introduce gene expression elements such as promoters, enhancers etc. that can increase expression of a gene or repressors or other elements that reduce expression of a gene or other transcript (such as a microRNA or a regulatory pseudogene. Genome editing as disclosed herein can further be used to introduce genes, such as exogenous genes, into a locus. Using the genome editing methods herein, multiple genes can be introduced into a genome target site on a donor fragment. A donor fragment can optionally include a detectable marker gene, e.g., a fluorescent protein gene, that can be used to evaluate penetrance of the introduced gene or genes that are physically linked to the detectable marker gene, using the methods provided herein.

Targeted Endonucleases

A range of molecular tools have been recently developed to allow for specific genetic engineering, particularly of eukaryotic genomes. Initially Zinc-Finger Nucleases (ZFNs) were developed, followed by Transcription Activator-Like Effector Nucleases (TALENs). With the development of the CRISPR/Cas9 system, targeted genome editing has been achieved across eukaryotic species. A CRISPR/Cas9 system generally comprises a Cas9 endonuclease (e.g., of *Streptococcus pyogenes*) and a synthetic guide RNA (gRNA) molecule that combines the functions of CRISPR RNA (cRNA) and transactivating cRNA (tracrRNA). A gRNA directs a Cas9 endonuclease to a target sequence complementary to 20 nucleotides preceding a protospacer-associated motif (PAM) NGG sequence required for Cas9 activity. In some embodiments, cRNA and tracrRNA may be combined into a single RNA which may contain nucleotide modifications.

In the context of the present disclosure, any number of targeted endonucleases (e.g., a CRISPR-associated ribonucleoprotein complex, such as Cas9 or Cpf1, a homing nuclease, a zinc-fingered nuclease, a TALEN, a megaTAL nuclease, an argonaute nuclease, and/or derivatives thereof) can be used to induce intended mutagenesis (e.g., genome editing) in various organisms. In some embodiments, targeted endonuclease is a site-specific nuclease capable of generating double strand breaks (DSBs) at selected positions along a strand of DNA. In some embodiments, targeted endonuclease is a site-specific nuclease capable of generating single stranded nicks at selected positions along a strand of DNA.

In some embodiments, a targeted endonuclease can be modified, such as having an amino acid substitution for provided, for example, enhanced thermostability, salt tolerance and/or pH tolerance. In other embodiments, a targeted endonuclease may be biotinylated, fused with streptavidin and/or incorporate other affinity-based (e.g., bait/prey) technology. In certain embodiments, a targeted endonuclease may have an altered recognition site specificity (e.g., SpCas9 variant having altered PAM site specificity).

In some embodiments, an engineered genomic editing event is a modified CAS or CPF-1 mediated event. In some embodiments, an engineered genomic editing event is a Cas9-mediated editing event. In some embodiments, an engineered genomic editing event is a CPF 1-mediated editing event. In some embodiments, an engineered genomic editing event is carried out by a TALEN, megaTAL, Zinc-fingered nuclease, a homing endonuclease, a restriction endonuclease.

CRISPR-based targeted endonucleases are further discussed herein to provide a further detailed non-limiting example of use of a targeted endonuclease. We note that the nomenclature around such targeted nucleases remains in flux. For purposes herein, we use the term "CRISPR-based" to generally mean endonucleases comprising a nucleic acid sequence, the sequence of which can be modified to redefine a nucleic acid sequence to be cleaved. Cas9 and CPF1 are examples of such targeted endonucleases currently in use, but many more appear to exist different places in the natural world and the availability of different varieties of such targeted and easily tunable nucleases is expected to grow rapidly in the coming years. Similarly, multiple engineered variants of these enzymes to enhance or modify their properties are becoming available. Herein, we explicitly contemplate use of substantially functionally similar targeted endonucleases not explicitly described herein or not yet discovered, to achieve a similar purpose to disclosures described within.

Cells and Vectors for Genome Editing

Genomic editing systems and/or methods may include a viral vector, e.g. Adenovirus, or Adeno-associated Virus (AAV). Typically, an expression vector DNA can be delivered to a cell by transformation, electroporation or virus (AAV). Also, RNA can be delivered into a cell by injection or electroporation. Proteins can be delivered to cells via electroporation, peptide (HIV) tags.

The present disclosure provides cells whose genomes are to be editing and/or have been edited. Provided methods can be performed with any cells that can be cultured, including prokaryotic cells (bacteria and archaea) and eukaryotic cells, including, without limitation, plant cells, animal cells, and protozoans, fungi, and algae. In some embodiments, populations of cells to be edited and/or analyzed in the context of the present disclosure are pluripotent stem cells, embryonic stem cells, immune cells, or plant cells.

In some embodiments, populations of cells to be edited and/or analyzed in the context of the present disclosure are or include animal cells (e.g., mammalian cells, e.g., human cells). In some embodiments, populations of cell are or include mammalian stem cells. In some embodiments, populations of cells to be edited in the context of the present disclosure are or include plant cells.

Kits with Reagents

Aspects of the present technology further encompass kits for conducting various aspects of Duplex Sequencing methods (also referred to herein as a "DS kit"). In some embodiments, a kit may comprise various reagents along with instructions for conducting one or more of the methods or method steps disclosed herein for nucleic acid extraction, nucleic acid library preparation, amplification (e.g. via PCR) and sequencing. In one embodiment, a kit may further include a computer program product (e.g., coded algorithm to run on a computer, an access code to a cloud-based server for running one or more algorithms, etc.) for analyzing sequencing data (e.g., raw sequencing data, sequencing reads, etc.) to determine, for example, a successful genome editing event, an incorrect genome editing event, an unintended (e.g., off target) genome editing event, a clonal selection, a clonal expansion, etc., associated with a sample and in accordance with aspects of the present technology. Kits may include DNA standards and other forms of positive and negative controls.

In some embodiments, a D S kit may comprise reagents or combinations of reagents suitable for performing various aspects of sample preparation (e.g., tissue manipulation, DNA extraction, DNA fragmentation), nucleic acid library preparation, amplification and sequencing. For example, a D S kit may optionally comprise one or more DNA extraction reagents (e.g., buffers, columns, etc.) and/or tissue extraction reagents. Optionally, a D S kit may further comprise one or more reagents or tools for fragmenting double-stranded DNA, such as by physical means (e.g., tubes for facilitating acoustic shearing or sonication, nebulizer unit, etc.) or enzymatic means (e.g., enzymes for random or semi-random genomic shearing and appropriate reaction enzymes). For example, a kit may include DNA fragmentation reagents for enzymatically fragmenting double-stranded DNA that includes one or more of enzymes for targeted digestion (e.g., restriction endonucleases, CRISPR/Cas endonuclease(s) and RNA guides, and/or other endonucleases), double-stranded Fragmentase cocktails, single-stranded DNase enzymes (e.g., mung bean nuclease, S1 nuclease) for rendering fragments of DNA predominantly double-stranded and/or destroying single-stranded DNA, and appropriate buffers and solutions to facilitate such enzymatic reactions.

In an embodiment, a D S kit comprises primers and adapters for preparing a nucleic acid sequence library from a sample that is suitable for performing Duplex Sequencing process steps to generate error-corrected (e.g., high accuracy) sequences of double-stranded nucleic acid molecules in the sample. For example, the kit may comprise at least one pool of adapter molecules comprising single molecule identifier (SMI) sequences or the tools (e.g., single-stranded oligonucleotides) for the user to create it. In some embodiments, the pool of adapter molecules will comprise a suitable number of substantially unique SMI sequences such that a plurality of nucleic acid molecules in a sample can be substantially uniquely labeled following attachment of the adapter molecules, either alone or in combination with unique features of the fragments to which they are ligated. One experienced in the art of molecular tagging will recognize that what entails a "suitable" number of SMI sequences will vary by multiple orders of magnitude depending on various specific factors (input DNA, type of DNA fragmentation, average size of fragments, complexity vs repetitiveness of sequences being sequenced within a genome etc.) Optionally, the adaptor molecules further include one or more PCR primer binding sites, one or more sequencing primer binding sites, or both. In another embodiment, a D S kit does not include adapter molecules comprising SMI sequences or barcodes, but instead includes conventional adapter molecules (e.g., Y-shape sequencing adapters, etc.) and various method steps can utilize endogenous SMIs to relate molecule sequence reads. In some embodiments, the adapter molecules are indexing adapters and/or comprise an indexing sequence. In other embodiments, indexes are added to specific samples through "tailing in" by PCR using primers supplied in a kit In an embodiment, a D S kit comprises a set of adapter molecules each having a non-complementary region and/or some other strand defining element (SDE), or the tools for the user to create it (e.g., single-stranded oligonucleotides). In another embodiment, the kit comprises at least one set of adapter molecules wherein at least a subset of the adapter molecules each comprise at least one SMI and at least one SDE, or the tools to create them. Additional features for primers and adapters for preparing a nucleic acid sequencing library from a sample that is suitable for performing Duplex Sequencing process steps are described above as well as disclosed in ET.S. Patent No. 9,752,188, International Patent Publication No. WO2017/100441, and International Patent Application No. PCT/US 18/59908 (filed Nov. 8, 2018), all of which are incorporated by reference herein in their entireties.

Additionally, a kit may further include DNA quantification materials such as, for example, DNA binding dye such as SYBR™ green or SYBR™ gold (available from Thermo Fisher Scientific, Waltham, MA) or the alike for use with a Qubit fluorometer (e.g., available from Thermo Fisher Scientific, Waltham, MA), or PicoGreen™ dye (e.g., available from Thermo Fisher Scientific, Waltham, MA) for use on a suitable fluorescence spectrometer or a real-time PCR machine or digital-droplet PCR machine. Other reagents suitable for DNA quantification on other platforms are also contemplated. Further embodiments include kits comprising one or more of nucleic acid size selection reagents (e.g., Solid Phase Reversible Immobilization (SPRI) magnetic beads, gels, columns), columns for target DNA capture using bait/pray hybridization, qPCR reagents (e.g., for copy number determination) and/or digital droplet PCR reagents. In some embodiments, a kit may optionally include one or more of library preparation enzymes (ligase, polymerase(s), endonuclease(s), reverse transcriptase for e.g., RNA interrogations), dNTPs, buffers, capture reagents (e.g., beads, surfaces, coated tubes, columns, etc.), indexing primers, amplification primers (PCR primers) and sequencing primers. In some embodiments, a kit may include reagents for assessing types of DNA damage such as an error-prone DNA polymerase and/or a high-fidelity DNA polymerase. Additional additives and reagents are contemplated for PCR or ligation reactions in specific conditions (e.g., high GC rich genome/target).

In an embodiment, the kits further comprise reagents, such as DNA error correcting enzymes that repair DNA sequence errors that interfere with polymerase chain reaction (PCR) processes (versus repairing mutations leading to disease). By way of non-limiting example, the enzymes comprise one or more of the following: monofunctional uracil-DNA glycosylase (hSMUG1), Uracil-DNA Glycosylase (UDG), N-glycosylase/AP-lyase NEIL 1 protein (hNEIL1), Formamidopyrimidine DNA glycosylase (FPG), 8-oxoguanine DNA glycosylase (OGG 1), human apurinic/apyrimidinic endonuclease (APE 1), endonuclease III (Endo III), endonuclease IV (Endo IV), endonuclease V (Endo V), endonuclease VIII (Endo VIII), T7 endonuclease I (T7 Endo I), T4 pyrimidine dimer glycosylase (T4 PDG), human single-strand-selective human alkyladenine DNA glycosylase (hAAG), etc., among other glycosylases, lyases, endonucleases and exonucleases etc.; and can be utilized to correct DNA damage (e.g., in vitro or in vivo DNA damage). Some of such DNA repair enzymes, for example, are glycoslyases that remove damaged bases from DNA. For example, UDG removes uracil that results from cytosine deamination (caused by spontaneous hydrolysis of cytosine) and FPG removes 8-oxo-guanine (e.g., most common DNA lesion that results from reactive oxygen species). FPG also has lyase activity that can generate 1 base gap at abasic sites. Such abasic sites will subsequently fail to amplify by PCR, for example, because the polymerase fails copy the template. Accordingly, the use of such DNA damage repair enzymes, and/or others listed here and as known in the art, can effectively remove damaged DNA that does not have a true mutation but might otherwise be undetected as an error.

The kits may further comprise appropriate controls, such as DNA amplification controls, nucleic acid (template) quantification controls, sequencing controls, nucleic acid molecules derived from a biological source that has undergone a genome editing event or clonal expansion following a genome editing event. In some embodiments, a kit may include a control population of cells. In some embodiments, a kit may include one or more components for engineered genome editing, e.g., vectors, gRNA, editing enzymes and/or reagents. Accordingly, a kit could include suitable reagents (test compounds, nucleic acid, control sequencing library, etc.) for providing controls that would yield expected Duplex Sequencing results that would determine protocol authenticity for an editing event. In some embodiments, a kit may include a reference sequence information for characterizing a genome editing event or clonal expansion following a genome editing event. In some embodiments, a kit may include sequence information useful for identifying one or more DNA variants in a population of edited cells. Such sequence information may be useful in determining neoplastic potential of the edited cells and/or evaluating efficacy of the genome editing process itself. In an embodiment, the kit comprises containers for shipping samples, storage material for stabilizing samples, material for freezing samples, such as cell samples, for analysis to detect DNA variants in a subject sample or in an engineered cell population. In another embodiment, a kit may include nucleic acid contamination control standards (e.g., hybridization capture probes with affinity to genomic regions in an organism that is different than the test or subject organism).

The kit may further comprise one or more other containers comprising materials desirable from a commercial and user standpoint, including PCR and sequencing buffers, diluents, subject sample extraction tools (e.g. syringes, swabs, etc.), and package inserts with instructions for use. In addition, a label can be provided on the container with directions for use, such as those described above; and/or the directions and/or other information can also be included on an insert which is included with the kit; and/or via a website address provided therein. The kit may also comprise laboratory tools such as, for example, sample tubes, plate sealers, microcentrifuge tube openers, labels, magnetic particle separator, foam inserts, ice packs, dry ice packs, insulation, etc.

The kits may further comprise a computer program product installable on an electronic computing device (e.g. laptop/desktop computer, tablet, etc.) or accessible via a network (e.g. remote server), wherein the computing device or remote server comprises one or more processors configured to execute instructions to perform operations comprising Duplex Sequencing analysis steps. For example, the processors may be configured to execute instructions for processing raw or unanalyzed sequencing reads to generate Duplex Sequencing data. In additional embodiments, the computer program product may include a database comprising subject or sample records (e.g., information regarding a particular subject or sample or groups of samples) and empirically-derived information regarding intended genome edit targeted region of DNA or non-targeted genomic regions. The computer program product is embodied in a non-transitory computer readable medium that, when executed on a computer, performs steps of the methods disclosed herein (e.g. see FIGS. 3-6).

The kits may further comprise include instructions and/or access codes/passwords and the like for accessing remote server(s) (including cloud-based servers) for uploading and downloading data (e.g., sequencing data, reports, other data)

or software to be installed on a local device. All computational work may reside on the remote server and be accessed by a user/kit user via internet connection, etc.

Selected Examples of Applications

As is described herein, provided methods may be used for any of a variety of purposes and/or in any of a variety of scenarios. Below are described examples of non-limiting applications and/or scenarios for the purposes of specific illustration only.

Quality Assessment of Genome Edited Cells

The present disclosure encompasses a recognition that genome editing can induce and/or select for neoplastic mutations. Accordingly, the present disclosure provides methods assessing neoplastic potential of a cell population following an engineered genomic editing event. Such methods are useful in quality control analyses for genomic editing and/or ensuring safety of cell-based therapies that have undergone genomic editing.

The present disclosure includes a recognition that genomic editing events may impose a selectively bias for cells that have increased or dysregulated cell cycle mutations (e.g., neoplastic mutations). Accordingly, it is important that genome edited cells be assessed and/or monitored for their neoplastic potential.

In some embodiments, the present disclosure provides methods of assessing neoplastic potential of a cell population following an engineered genomic editing event, which include Duplex Sequencing and determining if there is a variant present in the one or more cancer drivers among the plurality of enriched tagged DNA molecules by comparing the one or more correspondences to a reference genome sequence. In some embodiments, such methods include preparing a sequencing library from a sample comprising double-stranded DNA molecules originating from the cell population following the engineered genomic editing event, wherein preparing the sequence library comprises tagging a plurality of double-stranded DNA molecules to generate a plurality of tagged DNA molecules having first and second tagged strands; selectively enriching the first and second tagged strands for a subset of tagged DNA molecules that map to one or more cancer drivers to provide enriched tagged DNA molecules; generating an error-corrected sequence read for each of a plurality of enriched tagged DNA molecules, where the generating the error-corrected sequence reads comprises: sequencing one or more first and second tagged strands derived from the enriched tagged DNA molecules to provide a first strand sequence and a second strand sequence; comparing the first strand sequence and the second strand sequence to identify one or more correspondences between the first and second strand sequences; and determining if there is a variant present in the one or more cancer drivers among the plurality of enriched tagged DNA molecules by comparing the one or more correspondences to a reference genome sequence.

Of particular interest is the detection of one or more variants that include a functionally disruptive mutation. In some embodiments, provided methods are useful for detection of one or more variants in one or more cancer driver genes. In some embodiments, a cancer driver is a known cancer driver from Cancer Gene Census (CGC) or the COSMIC database (genes causally implicated in cancer). In some embodiments, a cancer driver gene is or includes: ABL, ACC, BCR BLCA, BRCA, CESC, CHOL, COAD, DLBC, DNMT3A, EGFR, ESCA, GBM, HNSC, RICH, KIRC, K1RP, LAML, LGG, LIHC, LUAD, LUSC, MESO, OV, PAAD, PCPG, PI3K, PIK3CA, PRAD, PTEN READ, SARC, SKCM, STAD, TGCT, THCA, THYM, UCEC, UCS, and/or UVM. In some embodiments, a cancer driver gene is or includes TP53. In some embodiments, a cancer driver gene is or includes HRAS, NRAS, or KRAS.

In some embodiments, if a variant is detected in one or more cancer drivers among the plurality of enriched tagged DNA molecules in the population of molecules, then the method may further include a step of determining a variant frequency of the variant among the plurality of enriched tagged DNA molecules.

In some embodiments, provided methods are performed at multiple time points to assess changes in the frequency and/or abundance of one or more variants. In some embodiments, provided methods are performed at a first time point and at a second, later time point. In some embodiments, a second time point is at least 2, 3, 4, 5, 6, 7, 10, 15, 20, 30, 60, 90, or 180 days after a first time point. In some embodiments, both the first and second time points are within about 30 days, within about 45 days, within about 60 days, within about 75 days, or within about 90 days following the engineered genomic editing event. Analysis at multiple time points may be useful for assessing neoplastic potential or an increase in neoplastic potential. For example, a cell population is determined to have neoplastic potential if the variant frequency from the second time point is greater than the variant frequency from the first time point. In some embodiments, a provided method is performed on a cell population that has undergone a genomic editing event and a portion of otherwise identical cells that have not undergone a genomic editing event. In some embodiments, provided methods include assessing and comparing variant frequency between an edited cell population and a comparable cell population that has not undergone the engineered genomic editing event.

Monitoring Cell Therapies

Genome edited cells may be used in a number of applications. For example, in some embodiments, a medical disorder is treated by administration of a genome-edited immune effector cell (e.g., a T cell) that elicits a specific immune response. In some embodiments, cells for use in a therapeutic application may be propagated for days, weeks, or months ex vivo as a bulk population within about 1, 2, 3, 4, 5 days or more following a genome editing event. In some embodiments, genome edited cells may be obtained from a subject after administration and analyzed. For example, in the case of an engineered immune cell, such edited cells may be obtained from the blood of a treated subject and characterized using methods of the present disclosure. In some embodiments, abundance of one or more variants in a cell population is monitored over time. In some embodiments, clonal expansion of one or more variants in a cell population is monitored over time.

Embodiments of Systems and Computing Environments for Characterization of Nucleic Acids Following Genomic Editing Suitable Comyutins Environments The following discussion provide a general description of a suitable computing environment in which aspects of the disclosure can be implemented. Although not required, aspects and embodiments of the disclosure will be described in the general context of computer-executable instructions, such as routines executed by a general-purpose computer, e.g., a server or personal computer. Those skilled in the relevant art will appreciate that the disclosure can be practiced with other computer system configurations, including Internet appliances, hand-held devices, wearable computers, cellular or mobile phones, multi-processor systems, microprocessor-based or programmable consumer electronics, settop boxes, network PCs, mini-computers, mainframe computers and the like. The disclosure can be embodied in a special purpose computer or data processor that is specifically programmed, configured or constructed to perform one or more of the computer-executable instructions explained in detail below. Indeed, the term "computer", as used generally herein, refers to any of the above devices, as well as any data processor.

The disclosure can also be practiced in distributed computing environments, where tasks or modules are performed by remote processing devices, which are linked through a communications network, such as a Local Area Network ("LAN"), Wide Area Network ("WAN") or the Internet. In a distributed computing environment, program modules or sub-routines may be located in both local and remote memory storage devices. Aspects of the disclosure described below may be stored or distributed on computer-readable media, including magnetic and optically readable and removable computer discs, stored as firmware in chips (e.g., EEPROM chips), as well as distributed electronically over the Internet or over other networks (including wireless networks). Those skilled in the relevant art will recognize that portions of the disclosure may reside on a server computer, while corresponding portions reside on a client computer. Data structures and transmission of data particular to aspects of the disclosure are also encompassed within the scope of the disclosure.

Embodiments of computers, such as a personal computer or workstation, can comprise one or more processors coupled to one or more user input devices and data storage devices. A computer can also be coupled to at least one output device such as a display device and one or more optional additional output devices (e.g., printer, plotter, speakers, tactile or olfactory output devices, etc.). The computer may be coupled to external computers, such as via an optional network connection, a wireless transceiver, or both.

Various input devices may include a keyboard and/or a pointing device such as a mouse. Other input devices are possible such as a microphone, joystick, pen, touch screen, scanner, digital camera, video camera, and the like. Further input devices can include sequencing machine(s) (e.g., massively parallel sequencer), fluoroscopes, and other laboratory equipment, etc. Suitable data storage devices may include any type of computer-readable media that can store data accessible by the computer, such as magnetic hard and floppy disk drives, optical disk drives, magnetic cassettes, tape drives, flash memory cards, digital video disks (DVDs), Bernoulli cartridges, RAMs, ROMs, smart cards, etc. Indeed, any medium for storing or transmitting computer-readable instructions and data may be employed, including a connection port to or node on a network such as a local area network (LAN), wide area network (WAN) or the Internet.

Aspects of the disclosure may be practiced in a variety of other computing environments. For example, a distributed computing environment with a network interface can include one or more user computers in a system where they may include a browser program module that permits the computer to access and exchange data with the Internet, including web sites within the World Wide Web portion of the Internet. User computers may include other program modules such as an operating system, one or more application programs (e.g., word processing or spread sheet applications), and the like. The computers may be general-purpose devices that can be programmed to run various types of applications, or they may be single-purpose devices optimized or limited to a particular function or class of functions. More importantly, while shown with network browsers, any application program for providing a graphical user interface to users may be employed, as described in detail below; the use of a web browser and web interface are only used as a familiar example here.

At least one server computer, coupled to the Internet or World Wide Web ("Web"), can perform much or all of the functions for receiving, routing and storing of electronic messages, such as web pages, data streams, audio signals, and electronic images that are described herein. While the Internet is shown, a private network, such as an intranet may indeed be preferred in some applications. The network may have a client-server architecture, in which a computer is dedicated to serving other client computers, or it may have other architectures such as a peer-to-peer, in which one or more computers serve simultaneously as servers and clients. A database or databases, coupled to the server computer(s), can store much of the web pages and content exchanged between the user computers. The server computer(s), including the database(s), may employ security measures to inhibit malicious attacks on the system, and to preserve integrity of the messages and data stored therein (e.g., firewall systems, secure socket layers (SSL), password protection schemes, encryption, and the like).

A suitable server computer may include a server engine, a web page management component, a content management component and a database management component, among other features. The server engine performs basic processing and operating system level tasks. The web page management component handles creation and display or routing of web pages. Users may access the server computer by means of a URL associated therewith. The content management component handles most of the functions in the embodiments described herein. The database management component includes storage and retrieval tasks with respect to the database, queries to the database, read and write functions to the database and storage of data such as video, graphics and audio signals.

Many of the functional units described herein have been labeled as modules, in order to more particularly emphasize their implementation independence. For example, modules may be implemented in software for execution by various types of processors. An identified module of executable code may, for instance, comprise one or more physical or logical blocks of computer instructions which may, for instance, be organized as an object, procedure, or function. The identified blocks of computer instructions need not be physically located together but may comprise disparate instructions stored in different locations which, when joined logically together, comprise the module and achieve the stated purpose for the module.

A module may also be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

A module of executable code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network.

System for Characterizing Genome Editing and Clonal Expansion

The present technology further comprises a system (e.g. a networked computer system, a high throughput automated system, etc.) for processing a biological sample comprising a nucleic acid mixture, and transmitting the sequencing data via a wired or wireless network to a server to determine the sample's error-corrected sequence reads (e.g., duplex sequence reads, duplex consensus sequence, etc.), sequence reads at intended genomic loci, sequence reads at unintended genetic loci, sequence reads at cancer driver loci, expected sequences, anticipated genomic edited sequences, reference sequences, variant identification, variant frequency, quantification of individual/attributable genotypes, and the like.

As described in additional detail below, and with respect to the embodiment illustrated in FIG. 2, a computerized system for characterization of nucleic acids following genomic editing of a cell population comprises: (1) a server (e.g., a remote server, or locally stored server); (2) a plurality of user electronic computing devices able to generate and/or transmit sequencing data; (3) optionally, a database with reference sequences (e.g., expected genomic sequences, anticipated genomic edited sequences, etc.) and associated information (optional); and (4) a wired or wireless network for transmitting electronic communications between the electronic computing devices, database, and the server. The server further comprises: (a) a database storing genome editing record results, and records of variant profiles (e.g. mutation profiles, variant frequency results, etc.); (b) one or more processors communicatively coupled to a memory; and one or more non-transitory computer-readable storage devices or medium comprising instructions for processor(s), wherein said processors are configured to execute said instructions to perform operations comprising one or more of the steps described in FIGS. 3-6.

In one embodiment, the present technology further comprises a non-transitory computer-readable storage media comprising instructions that, when executed by one or more processors, performs methods for determining the presence of an anticipated genomic edited sequence at one or more intended genomic loci, the presence of an undesired genomic edited sequence at one or more intended genomic loci, the presence of an undesired genomic edited sequence at one or more unintended genomic loci, the presence of one or more variants in a cancer driver or non-cancer driver loci, a frequency of on-target genomic alteration at an intended genomic locus among a population, a frequency of off-target genomic alterations at one or more unintended genomic loci, a variant frequency of one or more variants present in the nucleic acid mixture, the quantification of each variant in the mixture over time following a genomic editing event, and the like. In particular embodiments, the methods can include one or more of the steps described in FIGS. 3-6.

Additional aspects of the present technology are directed to computerized methods for determining the presence of an anticipated genomic edited sequence at one or more intended genomic loci, the presence of an undesired genomic edited sequence at one or more intended genomic loci, the presence of an undesired genomic edited sequence at one or more unintended genomic loci, the presence of one or more variants in a cancer driver or non-cancer driver loci, a frequency of on-target genomic alteration at an intended genomic locus among a population, a frequency of off-target genomic alterations at one or more untended genomic loci, a variant frequency of one or more variants present in the nucleic acid mixture, the quantification of each variant in the mixture over time following a genomic editing event, and the like. In particular embodiments, the methods can include one or more of the steps described in FIGS. 3-6.

Figure 2:
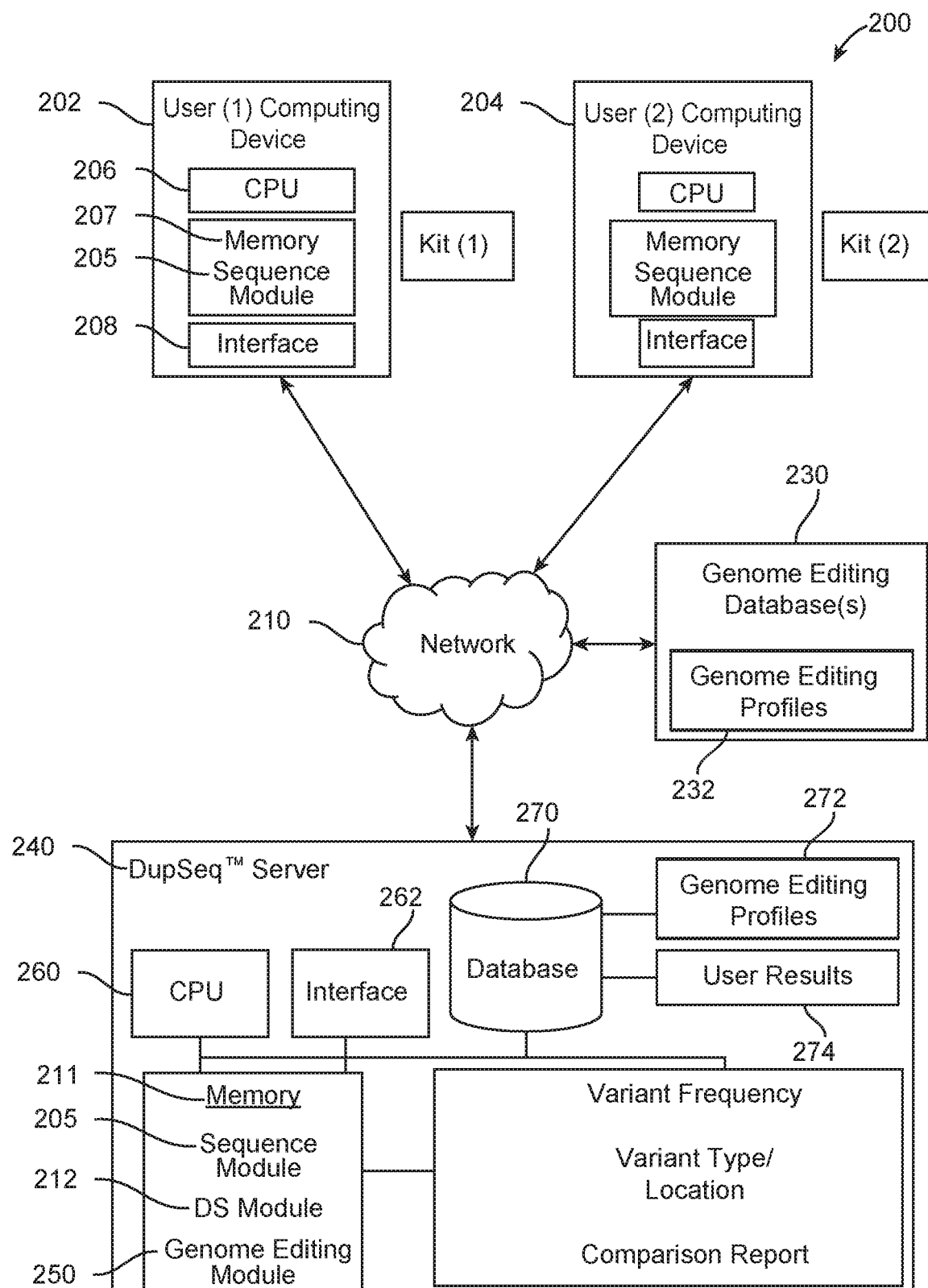
FIG. 2 is a schematic diagram of a network computer system for use with methods and/or kits disclosed herein that are useful to identify and/or quantify genomic alterations (e.g., directed genomic alterations, variants, mutations, etc.) and identify clonal selection and/or clonal expansion following a genome editing event (e.g., an engineered genome editing event) in accordance with some embodiments of the present technology.
Figure 3:
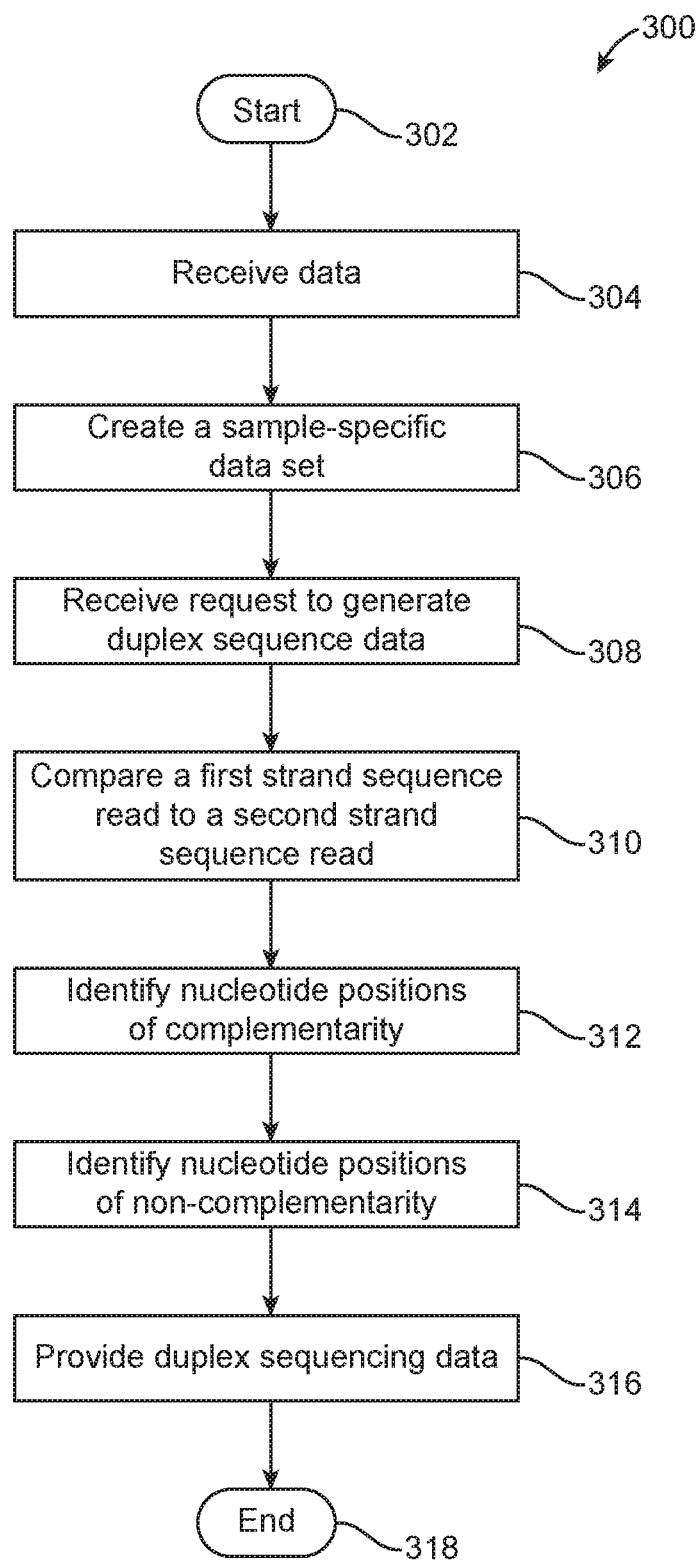
FIG. 3 is a flow diagram illustrating an exemplary routine for producing Duplex Sequencing consensus sequence data in accordance with some embodiments of the present technology.
Figure 4:
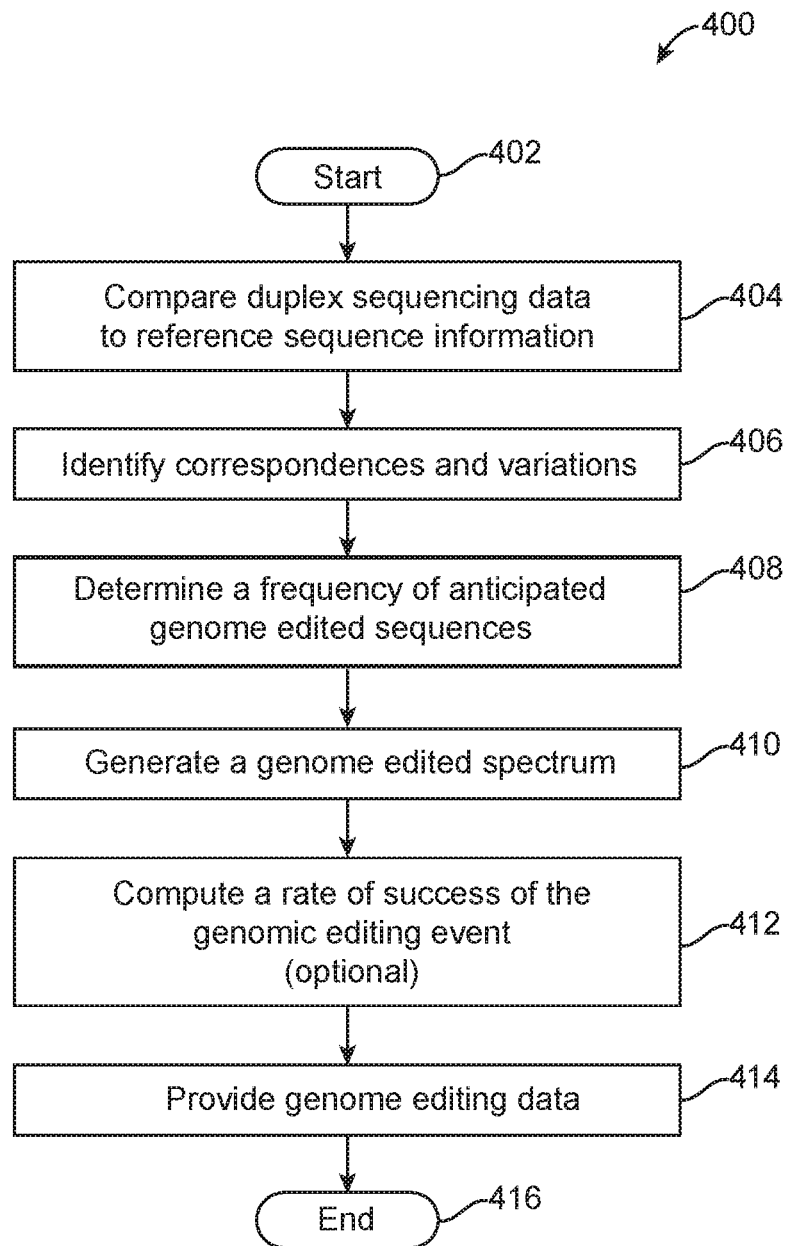
FIG. 4 is a flow diagram illustrating a routine for detecting and identifying edited sequences at intended genomic loci resulting from a genomic editing event in a cell population in accordance with some embodiments of the present technology.
Figure 5:
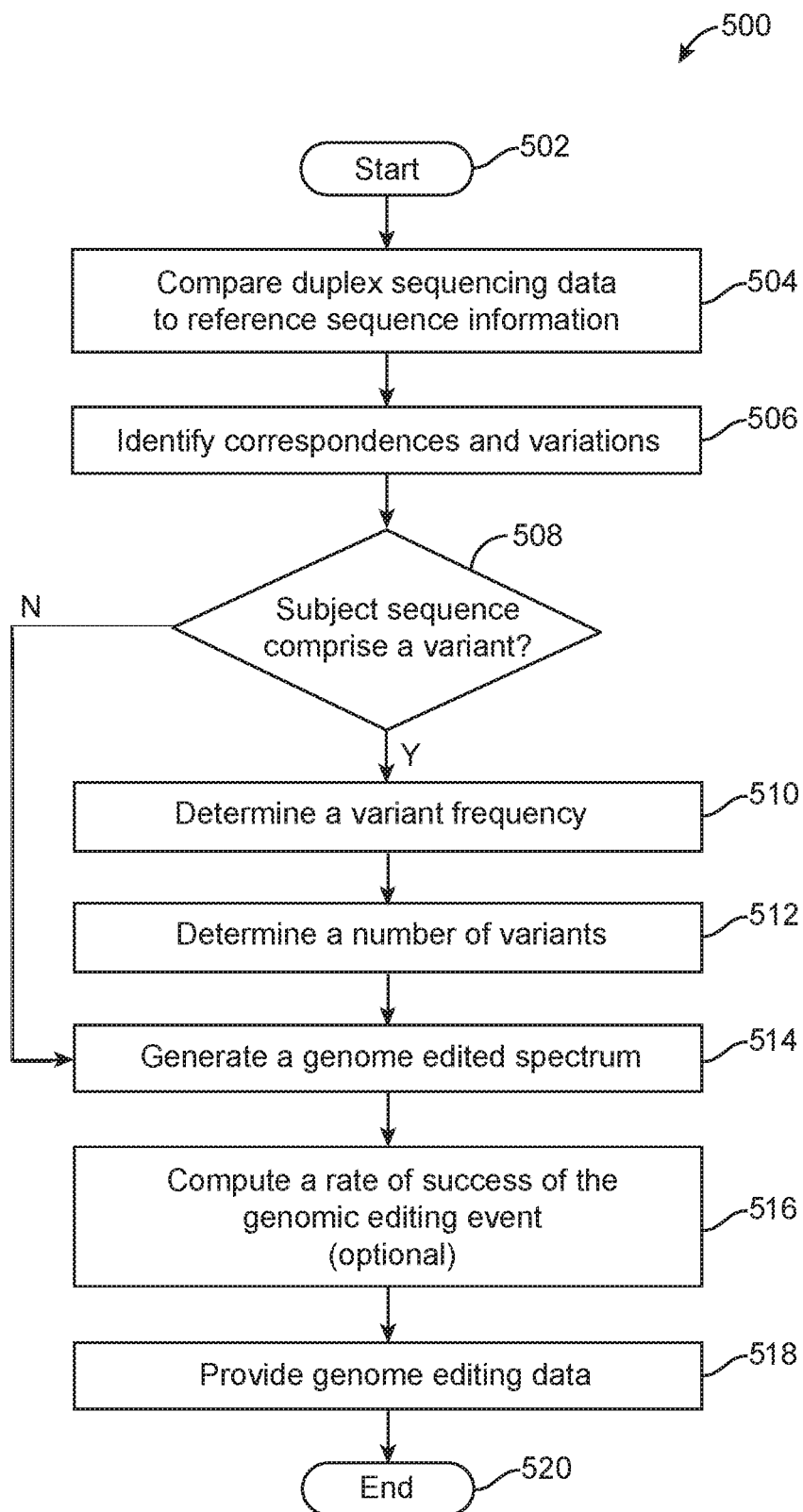
FIG. 5 is a flow diagram illustrating a routine for detecting and identifying edited sequences at unintended genomic loci resulting from a genomic editing event in a cell population in accordance with some embodiments of the present technology.
Figure 6:
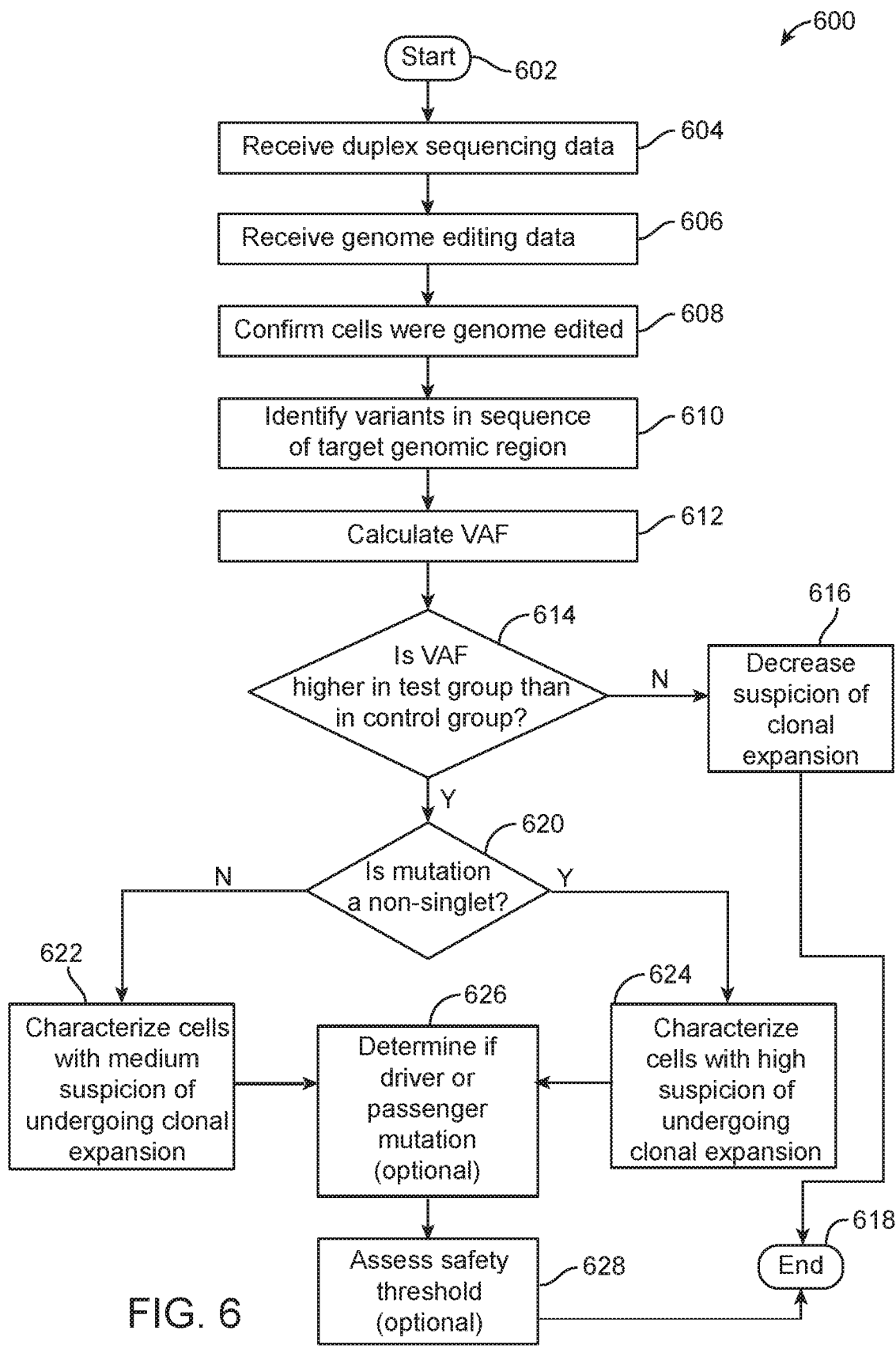
FIG. 6 is a flow diagram illustrating a routine for detecting and identifying clonal expansion of a cell within a cell population following a genomic editing event in accordance with some embodiments of the present technology.

FIG. 2 is a block diagram of a computer system 400 with a computer program product 250 installed thereon and for use with the methods disclosed herein to characterize nucleic acids following genomic editing of a cell population. Although FIG. 2 illustrates various computing system components, it is contemplated that other or different components known to those of ordinary skill in the art, such as those discussed above, can provide a suitable computing environment in which aspects of the disclosure can be implemented. FIG. 3 is a flow diagram illustrating a routine for providing Duplex Sequencing consensus sequence data in accordance with an embodiment of the present technology. FIGS. 4-6 are flow diagrams illustrating various routines for identifying and/or quantifying genomic alterations (e.g., directed genomic alterations, variants, mutations, etc.) and clonal expansion of cells in a cell population following a genomic editing event from nucleic acids originating from the genome edited cell population. In accordance with aspects of the present technology, methods described with respect to FIGS. 4-6 can provide sample data including, for example, genetic profiles of cell populations following genomic editing, including accurate/desired genome edited sequences present in a sample, inaccurate/undesired genome edited sequences present in a sample, undesired genome edited sequences in unintended regions of the genome present in a sample, variants in cancer drivers that would impart a growth advantage or bias present in a sample, an unexpected and/or undesired variant frequency present in the sample, quantification of variants and/or genomic edits represented within the sample, and information derived from comparison of sample data to data sets of reference sequences (including databases comprising anticipated genomic edited sequences, expected sequences, background levels of variant frequency, etc.).

As illustrated in FIG. 2, the computer system 200 can comprise a plurality of user computing devices 202, 204; a wired or wireless network 210 and a server ("DupSeg™" server) 240 comprising processors to analyze genome edited sequences and characterize nucleic acids originating from cell populations following a genomic editing event. In embodiments, user computing devices 202, 204 can be used to generate and/or transmit sequencing data. In one embodiment, users of computing devices 202, 204 may be those performing other aspects of the present technology such as Duplex Sequencing method steps of biological samples for characterizing nucleic acids following genomic editing of a cell population. In one example, users of computing devices 202, 204 perform certain Duplex Sequencing method steps with a kit (1, 2) comprising reagents and/or adapters, in accordance with an embodiment of the present technology, to interrogate biological samples.

As illustrated, each user computing device 202, 204 includes at least one central processing unit 206, a memory 207 and a user and network interface 208. In an embodiment, the user devices 202, 204 comprise a desktop, laptop, or a tablet computer.

Although two user computing devices 202, 204 are depicted, it is contemplated that any number of user computing devices may be included or connected to other components of the system 200. Additionally, computing devices 202, 204 may also be representative of a plurality of devices and software used by User (1) and User (2) to amplify and sequence the samples. For example, a computing device may be a sequencing machine (e.g., Illumina HiSeq™, Ion Torrent PGM, ABI SOLiD™ sequencer, PacBio RS, Helicos Heliscope™ etc.), a real-time PCR machine (e.g., ABI 7900, Fluidigm BioMark™, etc.), a microarray instrument, etc.

In addition to the above described components, the system 200 may further comprise a database 230 for storing genome editing profiles 232, including reference sequences and associated information. For example, the database 230, which can be accessible by the server 240, can comprise records or collections of expected genomic sequences, anticipated genomic edited sequences, known cancer driver mutations, genomic mutagenic hotspots or mutation-prone sites, known microsatellite loci, known regions of homologous sequences, background variant frequency levels, known genotype profiles of starting material (e.g., mixtures of cells), and the like. In a particular example, the database 230 can be a third-party database comprising genome editing profiles 232, including reference sequences and associated information. For example, various databases comprising genome reference sequences, genome sequences from healthy (e.g., non-diseased or mutated) biological sources, sequences of cancer drivers, catalogues of cancer driver mutations, and regions of sequence homology can be queried for particular applications. In another embodiment, the database can be a standalone database 230 (private or not private) hosted separately from server 240, or a database can be hosted on the server 240, such as database 270, that comprises empirically-derived genome editing profiles 272, including expected genome sequences and variant profiles. In some embodiments, as the system 200 is used to generate new genome editing profiles from one or more cell populations, the data generated from use of the system 200 and associated methods (e.g., methods described herein and, for example, in FIGS. 3-6), can be uploaded to the database 230 and/or 270 so additional genome editing profiles 232, 272 can be created for future comparison activities.

The server 240 can be configured to receive, compute and analyze sequencing data (e.g., raw sequencing files) and related information from user computing devices 202, 204 via the network 210. Sample-specific raw sequencing data can be computed locally using a computer program product/module (Sequence Module 205) installed on devices 202, 204, or accessible from the server 240 via the network 210, or using other sequencing software well known in the art. The raw sequence data can then be transmitted via the network 210 to the server 240 and user results 274 can be stored in database 270. The server 240 also comprises program product/module "DS Module" 212 configured to receive the raw sequencing data from the database 270 and configured to computationally generate error corrected double-stranded sequence reads using, for example, Duplex Sequencing techniques disclosed herein. While DS Module 212 is shown on server 240, one of ordinary skill in the art would recognize that DS Module 212 can alternatively, be hosted at operated at devices 202, 204 or on another server (not shown).

The server 240 can comprise at least one central processing unit (CPU) 260, a user and a network interface 262 (or server-dedicated computing device with interface connected to the server), a database 270, such as described above, with a plurality of computer files/records to store genome editing profiles 272, and files/records to store results (e.g., raw sequencing data, Duplex Sequencing data, intended genomic loci analysis, unintended genomic loci analysis, variant analysis, variant frequency analysis, etc.) for tested samples 274. Server 240 further comprises a computer memory 211 having stored thereon the Genome Editing Computer Program Product (Genome Editing Module) 250, in accordance with aspects of the present technology.

Computer program product/module 250 is embodied in a non-transitory computer readable medium that, when executed on a computer (e.g. server 240), performs steps of the methods disclosed herein for characterization of nucleic acids following genomic editing of a cell population (e.g., detecting and identifying genomic alterations, detecting and identifying background variants, detecting and identifying clonal expansion following a genomic editing event, and/or quantifying the same. Another aspect of the present disclosure comprises the computer program product/module 250 comprising a non-transitory computer-usable medium having computer-readable program codes or instructions embodied thereon for enabling a processor to carry out genome editing analysis (e.g. characterize genomic alterations at intended and unintended genomic loci, quantify desired and undesired alterations to the genome following a genomic editing event, identify variants, quantify identified variants, determining variant frequency within a cell population, genome editing comparison reports, etc.). These computer program instructions may be loaded onto a computer or other programmable apparatus to produce a machine such that the instructions which execute on the computer or other programmable apparatus create means for implementing the functions or steps described herein. These computer program instructions may also be stored in a computer-readable memory or medium that can direct a computer or other programmable apparatus to function in a particular manner, such that the instructions stored in the computer-readable memory or medium produce an article of manufacture including instruction means which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

Furthermore, computer program product/module 250 may be implemented in any suitable language and/or browsers. For example, it may be implemented with Python, C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the Macintosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The system invokes a number of routines. While some of the routines are described herein, one skilled in the art is capable of identifying other routines the system could perform. Moreover, the routines described herein can be altered in various ways. As examples, the order of illustrated logic may be rearranged, substeps may be performed in parallel, illustrated logic may be omitted, other logic may be included, etc.

FIG. 3 is a flow diagram illustrating routine 300 for providing Duplex Sequencing Data for double-stranded nucleic acid molecules in a sample (e.g., a sample from a biological mixture). The routine 300 can be invoked by a computing device, such as a client computer or a server computer coupled to a computer network. In one embodiment the computing device includes sequence data generator and/or a sequence module. As an example, the computing device may invoke the routine 300 after an operator engages a user interface in communication with the computing device.

The routine 300 begins at block 302 and the sequence module receives raw sequence data from a user computing device (block 304) and creates a sample-specific data set comprising a plurality of raw sequence reads derived from a plurality of nucleic acid molecules in the sample (block 306). In some embodiments, the server can store the sample-specific data set in a database for later processing. Next, the D S module receives a request for generating Duplex Consensus Sequencing data from the raw sequence data in the sample-specific data set (block 308). The DS module groups sequence reads from families representing an original double-stranded nucleic acid molecule (e.g., based on SMI sequences) and compares representative sequences from individual strands to each other (block 310). In one embodiment, the representative sequences can be one or more than one sequence read from each original nucleic acid molecule. In another embodiment, the representative sequences can be single-strand consensus sequences (SS-CSs) generated from alignment and error-correction within representative strands. In such embodiments, a SSCS from a first strand can be compared to a SSCS from a second strand.

At block 312, the DS module identifies nucleotide positions of complementarity between the compared representative strands. For example, the D S module identifies nucleotide positions along the compared (e.g., aligned) sequence reads where the nucleotide base calls are in agreement. Additionally, the D S module identifies positions of non-complementarity between the compared representative strands (block 314). Accordingly, the D S module can identify nucleotide positions along the compared (e.g., aligned) sequence reads where the nucleotide base calls are in disagreement.

Next, the DS module can provide Duplex Sequencing Data for double-stranded nucleic acid molecules in a sample (block 316). Such data can be in the form of duplex consensus sequences for each of the processed sequence reads. Duplex consensus sequences can include, in one embodiment, only nucleotide positions where the representative sequences from each strand of an original nucleic acid molecule are in agreement. Accordingly, in one embodiment, positions of disagreement can be eliminated or otherwise discounted such that the duplex consensus sequence is a high accuracy sequence read that has been error-corrected. In another embodiment, Duplex Sequencing Data can include reporting information on nucleotide positions of disagreement in order that such positions can be further analyzed (e.g., in instances where DNA damage can be assessed). The routine 300 may then continue at block 318, where it ends.

FIG. 4 is a flow diagram illustrating a routine 400 for detecting and identifying edited sequences at intended genomic loci resulting from a genomic editing event in a cell population. The routine 400 can be invoked by the computing device of FIG. 2. The routine 400 begins at block 402 and the genome editing module compares the Duplex Sequencing Data from FIG. 3 (e.g., following block 316) to reference sequence information (block 404) and identifies sequence correspondence and/or variation (e.g., where the subject sequence corresponds with a reference sequence, where the subject sequence corresponds with an anticipated genomic edited sequence, where the subject sequence varies from the reference sequence, etc.) at the intended genomic loci (block 406). For example, the reference sequence can be an anticipated genomic sequence (e.g., comprising the desired engineered genome edited sequence) and the comparison step can identify if the subject sequence comprises the anticipated genomic sequence. In another example, the reference sequence can comprise an unedited genomic sequence and the comparison step can identify if the subject sequence comprises a variation from the unedited genomic sequence.

Next, the genome editing module determines a frequency of anticipated genome edited sequences among the population of subject sequences (block 408) and generates a genome edited spectrum (block 410) for the sample. As such, a genome edited cell population analysis can be provided with information regarding the type of genomic edit(s) (e.g., desired, undesired, or no genome edit), location (within the respective intended genomic loci) and frequency of each edit event in the nucleic acid molecules analyzed from the sample. Optionally, the genome editing module can compute a rate of success of the genomic editing event (block 412), and further, optionally, providing information for increasing a rate of success of a future genomic editing event (not shown).

Next, the genome editing module can provide genome editing data (block 414) that can be stored in the sample-specific data set in the database. In some embodiments, not shown, the genome editing data can be used to generate a genome editing profile to be stored in the database for future comparison activities. The routine 400 may then continue at block 416, where it ends.

FIG. 5 is a flow diagram illustrating a routine 500 for detecting and identifying edited sequences at unintended genomic loci resulting from a genomic editing event in a cell population. The routine 500 can be invoked by the computing device of FIG. 2. The routine 500 begins at block 502 and the genome editing module compares the Duplex Sequencing Data from FIG. 3 (e.g., following block 316) to reference sequence information (block 504) and identifies sequence correspondence and/or variation (e.g., where the subject sequence corresponds with a reference sequence, where the subject sequence varies from the reference sequence, etc.) at the unintended genomic loci (block 506). For example, an unintended loci can comprise one or more of a mutation-prone site, a microsatellite locus, a sequence with sequence homology to an intended genomic locus, and/or a cancer driver, and the comparison step can identify if the subject sequence comprises an alteration or variant of the reference sequence (e.g., an unedited genomic sequence).

At decision block 508, the routine 500 determines whether the subject sequence comprises a variant at an unintended locus following the genomic editing event. If the unintended genomic locus comprises a variant, the genome editing module determines a variant frequency (block 510). If the unintended genomic locus does not comprise a variant, the genome editing module can evaluate additional unintended genomic loci (decision block 508 repeats until all unintended genomic loci are evaluated). If any variants are identified at any unintended genomic loci, the genome editing module determines the respective variant frequency (block 510) and determines a number of independent variants within the sample (block 512). Following block 512 and decision block 508 in instances where the subject sequences at unintended genomic loci do not vary from the reference sequence, the routine 500 can continue when the genome editing module generates a genome edited spectrum (block 514) for the sample. As such, a genome edited cell population analysis can be provided with information regarding the type of genomic edit(s) (e.g., undesired or no genome edit) at unintended loci, location (e.g., at suspected or susceptible unintended genomic loci) and frequency of each edit event in the nucleic acid molecules analyzed from the sample. Optionally, the genome editing module can compute a rate of success of the genomic editing event (block 516), and further, optionally, providing information for increasing a rate of success of a future genomic editing event (not shown).

Next, the genome editing module can provide genome editing data (block 518) that can be stored in the sample-specific data set in the database. In some embodiments, not shown, the genome editing data can be used to generate a genome editing profile to be stored in the database for future comparison activities. The routine 500 may then continue at block 520, where it ends.

FIG. 6 is a flow diagram illustrating a routine 600 for detecting and identifying clonal expansion of a cell in a cell population following a genomic editing event. The routine 600 can be invoked by the computing device of FIG. 2. The routine 600 begins at block 602 and the genome editing module receives Duplex Sequencing Data (block 604) from FIG. 3 (e.g., following block 316) and, optionally, genome editing data (block 606) from FIGS. 4 and 5 (e.g., following blocks 414 and 518, respectively) and confirms that the cell population was genome edited (block 608). Next, the genome editing module identifies variants in the sequence of a target genomic region (e.g., gene or another genomic region) (block 610). For example, the genome editing module can analyze Duplex Sequencing Data and, optionally, genome editing data at specific genetic loci (e.g., cancer driver genes, oncogenes, proto-oncogenes, tumor suppressor gene, other cancer driver genomic loci, etc.). Then, the genome editing module calculates a variant allele frequency (VAF) (block 612).

At decision block 614, the routine 600 determines whether the VAF is higher in a test group than in a control group. A control group can be, in some embodiments, Duplex Sequencing data derived from a cell population (e.g., a comparable cell population) that has not undergone a genomic editing event. In another embodiment, a control group can be an expected background VAF of a reference population. In another embodiment, the control group can be a calculated VAF of a particular variant present in a cell population at a first time point, and the test group can be the calculated VAF of the particular variant present in the same cell population at a later, second time point. In one example, the first time point can be before a time prior to the genomic editing event and the second time point can be a time after the genomic editing event (e.g., days, week, months following the genomic editing event, between 1 and about 30 days following the genomic editing event, greater than 30 days following the genomic editing event, etc.). In another example, the first time and the second time can be a time after the genomic editing event. If the VAF of the test group is not higher than a control group, the gene editing module labels the edited cell population as having a decreased suspicion of undergoing clonal expansion (block 616). The routine 600 may then continue at block 618, where it ends. If the VAF is higher in the test group than in the control group, the routine 600 continues at decision block 620, where the routine 600 determines if a variant is a non-singlet.

If the variant is a singlet, then the gene editing module characterizes the edited cell population with a medium level of suspicion of undergoing a clonal expansion (block 622). If the mutation is determined to be a non-singlet (i.e., a multiplet), the routine 600 characterizes the edited cell population with a high suspicion of undergoing a clonal expansion (block 624). Optionally, the genome editing module determines if the variant detected at the target genomic region is consistent with a driver mutation (e.g., a mutation known to drive cancer growth/transformation) or is consistent with a possible passenger mutation (block 626).

Optionally, for cell populations (e.g., cell populations to be used as a cell therapy, cell populations obtained from a patient, etc.) that have been characterized with either a medium level of suspicion (at block 622) or a high level of suspicion (at block 624), the genome editing module can assess a safety threshold for the cell population and/or determine a risk associated with developing a neoplastic condition or cancer disease (block 628). The routine 600 may then continue at block 618, where it ends.

Other steps and routines are also contemplated by the present technology. For example, the system (e.g., the genome editing module or other module) can be configured to analyze the genome editing data to determine if a cell population was genome edited, if a genome editing process was efficient and/or successful, to determine under what characteristics a genomic editing event is mutagenic or carcinogenic and the like. Other steps may include determining if a subject should be prophylactically or therapeutically treated using a cell therapy derived from a cell population following a genomic editing event and based on the genome editing data derived from a particular cell population's sample. Further steps may include determining if a subject should be therapeutically treated for cancer based on the genome editing data derived from a particular subject's biological sample. For example, once a clonal expansion or neoplastic potential of genome edited cell population is identified using the system, the server can then determine if the subject has been exposed to more than a safe threshold level of neoplastic potential of a genome edited cell population. If so, then a prophylactic or inhibitor disease treatments may be initiated.

EXPERIMENTAL EXAMPLES

The following section provides some limiting examples of methods for detecting and assessing clonal expansion of cells following an event using duplex sequencing and associated reagents.

Example 1

In one example, an initial cell population is subjected to targeted genome editing using the CRISPR/Cas9 endonuclease system. Cas9 causes double-stranded breaks in genomic DNA which has been shown in some applications to induce cell cycle arrest via the TP53 pathway (i.e. PMID 29892062, PMID 29892067). Genome editing has been theorized to have low efficiency in some instances, such as in embryonic stem cells due to cell cycle arrest induced by double-stranded break response, which is mediated my TP53. Those cells that do not arrest following genome editing process may harbor inactivating mutations or deletions or loss of TP53 (or other cancer driver genes) that disrupt the respective function and cause less restricted cell growth. Clonal expansion of cells harboring this mutation would outcompete neighboring cells. In this example, Duplex Sequencing will be used to generate error-corrected consensus sequence reads of targeted double-stranded DNA molecules and determine a variant frequency (e.g., a mutation allele frequency) for samples taken from a cell population following Cas9-mediated genome editing. The targeted double-stranded DNA molecules can include regions of TP53 or other cancer driver genes or portions thereof. Selective pressure for clonal expansion will be assessed by determining if mutant allele frequencies for cancer driver mutations exceed a threshold level (e.g., a predetermined level, a background level, a relative variant allele frequency greater than a non-selectable reference portion of the genome etc.). In some embodiments, targeted double-stranded DNA molecules may also include non-cancer driver loci. One or more variants present in such non-cancer driver loci are detectable and quantifiable using Duplex Sequencing. An increase in a variant frequency (e.g., a passenger mutation) following a genome editing event (e.g., an increase over a first time point and a later, second time point, an increase in frequency above a background level, etc.), may indicate that a mutation in a cancer driver may be present, thereby providing clonal selection for cells harboring such variants. Passenger mutations may be selected from among any or all of the genome, but in some cases are preferably high frequency mutations sites such as homopolymeric regions. Different forms of genetic lineage markers that may be used for clone identification may be found in: Salk et al 2010PMID 20951806

Example 2

This example describes use of Duplex Sequencing to determine if early mutations in cancer driver genes reflect tumorigenic potential of test carcinogens. Using a model mutation inducing agent, the present example shows that Duplex Sequencing is able to resolve mutations in individual DNA molecules among a population. The present example demonstrates that methods of the present disclosure provide the necessary sensitivity to detect such early stage neoplastic clonal selection of cells among a population of cells as well as subsequent clonal expansion of such cells.

In this example, the impact of urethane is examined in different mouse tissue types (lung, spleen, blood) in an FDA-accepted cancer-predisposed mouse model: Tg.rasH2 (Saitoh et al. Oncogene 1990. PMID 2202951). This mouse contains ~3 tandem copies of human HRAS with an activating enhancer mutation to boost expression on one hemizygous allele. These mice are predisposed to splenic angiosarcomas and lung adenocarcinomas, and are routinely used for 6 month carcinogenicity studies to substitute for 2 year wild-type animal studies. Tumors found in the mice have usually acquired activating mutations in one copy of the human HRAS protooncogene. Thus, the human HRAS transgene serves a model target cancer driver gene in these animals. Sequence analysis and mutation detection was performed for 4 native mouse genes (Rho, Hp, Ctnnbl, Polrlc), along with the native mouse Hras, Kras, Nras and human HRAS transgene.

In this example, Tg.rasH2 mice (n=5/group) were dosed with vehicle or a model mutation-inducing agent (e.g., a carcinogenic dose of urethane) (day 1,3,5) and sacrificed on day 29 for mutation detection by Duplex Sequencing in target tissues (lung, spleen) and whole blood. Target endogenous genes {Rho, Hp, Ctnnbl, Polrlc) and the native mouse Hras and human HRAS (trans)genes were also sequenced.

Tumors (splenic hemangiosarcomas; lung adenocarcinoma) were collected at week 11 from animals (n=5/group) dosed with urethane and subjected to whole exome sequencing (WES) to identify characteristic cancer driver mutations (CDM) in these tumors.

Figure 7:
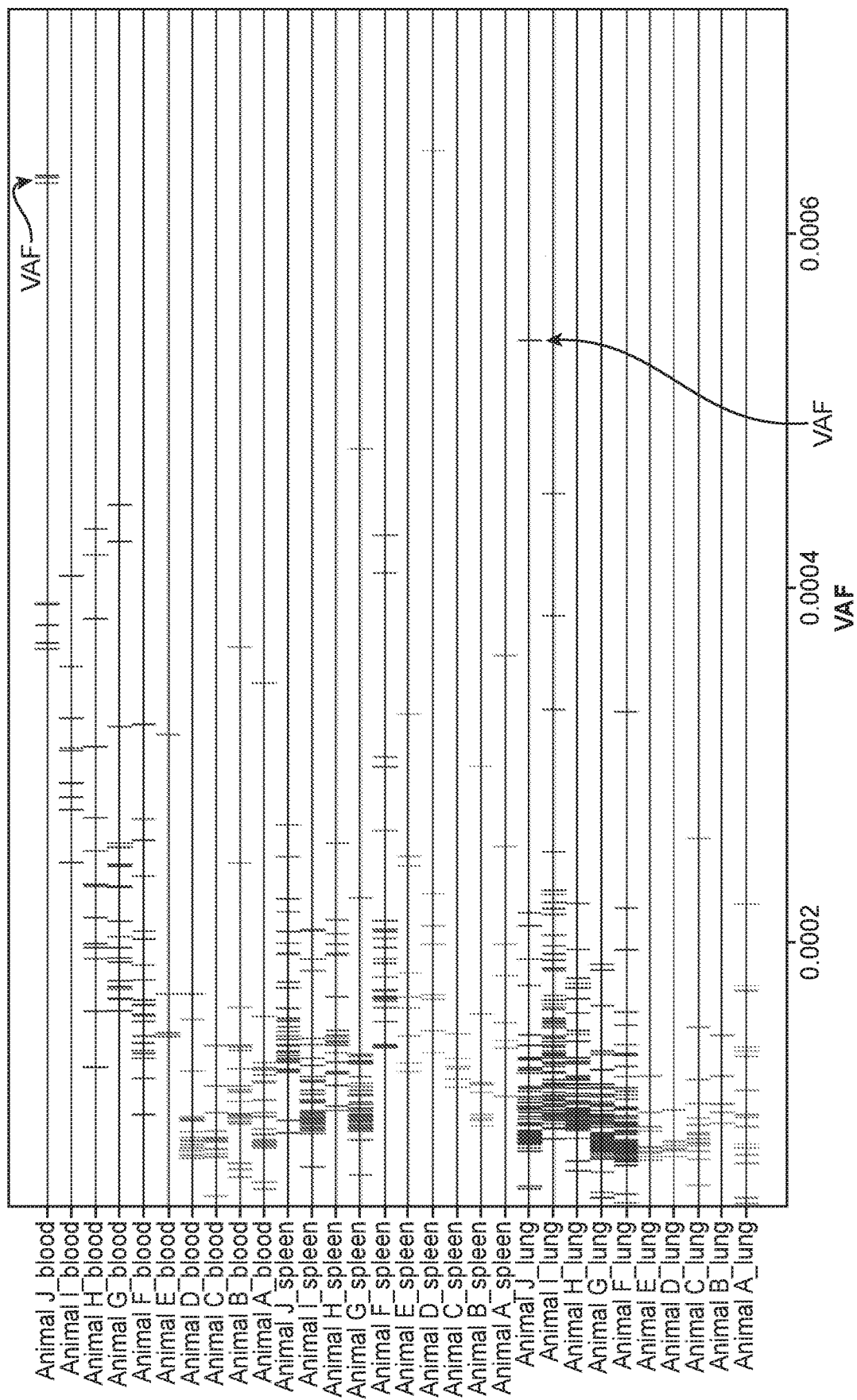
FIG. 7 is a graph illustrating early stage neoplastic clonal selection of variant allele fractions (VAF) as detected by Duplex Sequencing in accordance with some embodiments of the present technology.

FIG. 7 is a graph illustrating early stage neoplastic clonal selection of variant allele fractions (VAF) as detected by Duplex Sequencing. The vast majority of mutations identified occurred in single molecules and at very low variant allele fractions (VAFs), e.g., on the order of $1/10,000$. A few variants were found in multiple molecules in a sample and were identified as having considerably higher VAFs.

FIG. 8A is a graph illustrating single nucleotide variants (SNVs) aligning to exon 3 of the human HRAS transgene. Highlighted is a center residue in codon number 61 in exon 3 of human HRAS, which is consistent with this site being a common HRAS cancer-driving hotspot. Four out of five urethane treated lung samples harbored this mutation at variant allele frequencies of 0.1%-1.8%. All four SNVs are 'Y→A transversions in the context CTG. In addition, two treated spleen samples had mutations in this codon: one at this same position and one on an adjoining base pair. The fact that 4/5 treated lung samples had clonally expanded pathogenic mutations by only day 29, whereas very few mutations seen elsewhere on the panel were seen as >1 member clones or were seen repeated in multiple samples demonstrates strong evidence of substantial positive selection soon after exposure. Furthermore, Duplex Sequencing methods, in accordance with embodiments of the present technology, provides the necessary sensitivity to detect such early stage neoplastic clonal selection.

TABLE 1

| Mutation count | Number of families | |
|---|---|---|
| 1 | 829 | |
| 2 | 8 | |
| 4 | 1 | |
| 17 | 1 | Oncogenic AA 6 1 T > A |
| 58 | 1 | mutations in Human |
| 181 | 1 | HRAS gene in urethane |
| 300 | 1 | treated lung tissue |

Referring to Table 1, 97.5% of mutations were identified in a single molecule only, 1% were seen in two molecules and about 0.5% were seen in >2 molecules. The four highest level clones all occurred with oncogenic mutation in AA 61, the recurrent tumor hotspot in human HRAS. That the highest-level clones also appear at cancer hotspots further emphasized the magnitude of the strong selective pressure.

A far larger amount of DNA was extracted per sample than was converted into sequenced Duplex Molecules. The portion of tissue samples extracted yielded roughly 5 μg of genomic DNA. Converting this into genome equivalents, and multiplying by three yields the number of tg.HRAS copies in the extraction. Only ~⅓% of this was sequenced so roughly 300 times more mutants were present in the original portion of tissue sampled than detected.

TABLE 2

| Sample | ng DNA | Genomes | Copies tg.HRAS | Depth at AA 61 | % copies sequenced | Mutants | Mutant cells in original sample |
| --- | --- | --- | --- | --- | --- | --- | --- |
| 9957-Lung 1 | 5,640 | 1,692,000 | 5,076,000 | 16,425 | 0.324% | 300 | 92,712 |
| 9958-Lung 1 | 4,400 | 1,320,000 | 3,960,000 | 16,319 | 0.412% | 181 | 43,922 |
| 9959-Lung 1 | 4,480 | 1,344,000 | 4,032,000 | 13,692 | 0.310% | 58 | 17,080 |
| 9961-Lung 1 | 4,700 | 1,410,000 | 4,230,000 | 14,706 | 0.348% | 17 | 4,890 |

In this example, the selected clones encompassed more than 90,000 cells in the highest allele fraction clone. As a result, by calculation, within the 29 days of the study, e.g., from the time of mutation exposure, and assuming no cell death, the doubling time of these cells was roughly every 1.8 days $2^{(29/1.8)}$–90,000. Without being bound by theory, this calculated rate of cell doubling suggests the likely ability to detect these selected mutations in a short time frame (e.g., as few as two weeks).

This results of the experimental analysis of this example demonstrates that Duplex Sequencing quantifies induction of mutations extremely robustly and with tight replicate confidence intervals. Further, Duplex Sequence was able to resolve tissue-specific variations in the extent of mutation induction, with lung being observed to be more mutation prone than spleen and blood. The simple mutational spectrum of urethane exposure is clean and unbiased clustering can discriminate between groups. The triplet mutation spectrum of urethane shows a strong propensity for T→A and 'Y→C mutations within the context of "NTG" and the mutation spectrum is distinguishable from the vehicle control.

Additionally, mutation induction in peripheral blood closely mirrored that seen in the spleen and suggests that in-life sampling of peripheral blood could, for some mutagens, substitute for necropsy (or biopsy). Furthermore, this example provided clear evidence of selection for oncogenic mutations in the human HRAS transgene using Duplex Sequencing even at earlier time points (e.g., day 29) than what conventional studies would be able to detect (e.g., rodent tumor development). Thus, the present example demonstrates that analyzing the spectrum of mutation at target cancer driver genes (or other cancer driver loci) can accurately reflect the effects of a known model mutagen. Hence, Duplex Sequencing can provide early and accurate data with respect to evaluating early cancer driver mutations as biomarker of future cancer risk. Cross-species contamination persisted at extremely low levels but removal of foreign species contamination was performed automatically and confidently.

Figure 8B:
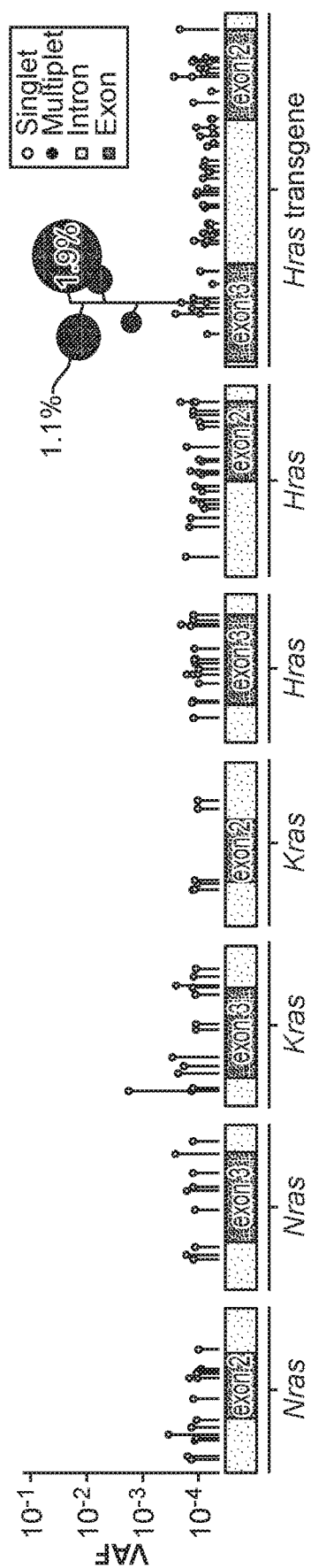
FIG. 8B is a graph illustrating single nucleotide variants (SNV) plotted over genomic intervals for exons captured from certain Ras family genes, including a human HRAS transgenic loci, in the Tg.RasH2 mouse model.

FIG. 8B shows single nucleotide variants (SNV) plotted over the genomic intervals for the exons captured from the Ras family of genes, including the human transgenic loci, in the Tg.RasH2 mouse model (shown in FIG. 8A). Singlets are mutations found in a single molecule. Multiplets are an identical mutation identified within multiple molecules within the same sampler and may represent a clonal expansion event. The height of each point corresponds to the variant allele frequency (VAF) of each SNV, with the with the size of the point corresponds to the for multiplet observations only. The location and relative frequency of Ras family human cancer mutational hotspots in COSMIC are indicated below each gene. A cluster of T>A transversions were observed in ⅘ urethane-treated lung samples and ⅕ urethane-treated splenic samples at the human oncogenic HRAS codon 61 hotspot. The observation of an identical mutation in independent samples as high VAF multiplets in a well-established cancer driver is a strong indication of positive selection. Notably these clones are of the transversion T>A in the context NTG, which is characteristic of urethane mutagenesis.

The present example describes methods for quickly detecting and assessing clonal expansion of cells harboring a potential mutation that is under selective pressure while providing detailed information about variant allele frequency, spectrum of mutation type(s) and genomic context data. For example, in some embodiments, the present technology includes method steps including extracting DNA from a cell population following a genomic editing event. DNA can be extracted at various time points following the genomic editing event. For example, the DNA can be extracted a few days or a few weeks or a few months following the event. In some embodiments, the DNA can be extracted from a cell population within 30 days or less following an event. Following DNA extraction, a DNA library may be prepared. In one embodiment, the extracted genomic DNA can be fragmented into a plurality of double-stranded DNA fragments, and each double stranded DNA fragment can be ligated to one or more desired adapter molecules (e.g., adapter molecule shown in FIG. 1A).

Following DNA library preparation, double-stranded adapter-DNA complexes can be amplified and sequenced with Duplex Sequencing method steps to result in direct high-accuracy DNA sequencing reads that provide detailed mutation location and frequency (e.g., resolving selection-mediating mutations below one-in-a-million). Thus, the Duplex Sequencing analysis can provide sensitive detection of genomic variants at any genetic locus in any tissue from any organism.

Further Examples

1. A method of characterizing a population of cells following an engineered genomic editing event directed to an intended genomic locus, the method comprising:
    (a) providing a sample comprising double-stranded DNA molecules originating from the population of cells following the engineered genomic editing event;
    (b) generating an error-corrected sequence read for each of a plurality of the double-stranded DNA molecules, comprising:
        ligating adapter molecules to the plurality of the double-stranded DNA molecules to generate a plurality of adapter-DNA molecules;
        generating a set of copies of an original first strand of the adapter-DNA molecule and a set of copies of an original second strand of the adapter-DNA molecule;

sequencing one or more copies of the original first and second strands to provide a first strand sequence and a second strand sequence;

comparing the first strand sequence and the second strand sequence to identify one or more correspondences between the first and second strand sequences; and (c) comparing one or more error-corrected sequence reads comprising a sequence at the intended genomic locus to an anticipated genome edited DNA sequence; or (d) comparing one or more error-corrected sequence reads comprising a sequence at an unintended genomic locus to a reference genome DNA sequence.

2. The method of example 1, wherein the method comprises both step (c) and step (d).

3. The method of example 1 or example 2, wherein generating an error-corrected sequence read for each of a plurality of the double-stranded DNA molecules further comprises selectively enriching one or more targeted genomic regions prior to sequencing to provide a plurality of enriched adapter-DNA molecules.

4. The method of example 4, wherein the one or more targeted genomic regions comprises the intended genomic locus in the genome.

5. The method of example 4, wherein the one or more targeted genomic regions comprises at least one unintended genomic locus in the genome.

6. The method of any one of examples 1-5, further comprising identifying one or more variants among the double-stranded DNA molecules.

7. The method of example 6, wherein the one or more variants comprise an incorrect mutation in the sequence of the intended genomic locus.

8. The method of example 7, wherein the incorrect mutation in the sequence of the intended genomic locus for genomic editing is due to a non-homologous end joining (NHEJ) event.

9. The method of example 6, wherein one or more variants are identified in one or more error-corrected sequence reads comprising a sequence at an unintended genomic locus.

10. The method of any one of examples 6-9, wherein the one or more variants comprise a functionally disruptive mutation.

11. The method of example 6 or example 9, further comprising (e) determining a frequency of the one or more variants among the plurality of double stranded DNA molecules.

12. The method of any one of examples 1-11, further comprising determining if one or more error-corrected sequence reads comprising the sequence at the intended genomic locus comprise the anticipated genome edited DNA sequence.

13. The method of example 12, further comprising determining a frequency of the anticipated genome edited DNA sequence among the error-corrected sequence reads comprising the sequence at the intended genomic locus.

14. The method of example 12, further comprising determining a frequency of an undesired DNA sequence among the error-corrected sequence reads comprising the sequence at the intended genomic locus.

15. The method of any one of examples 1-14, further comprising determining if one or more error-corrected sequence reads comprising the sequence at the unintended genomic locus comprises a variant.

16. The method of any one of examples 1-15, wherein the engineered genomic editing event is directed to a plurality of intended genomic loci.

17. The method of any one of examples 1-16, wherein step (d) comprises comparing error-corrected sequence reads comprising sequences at a plurality of unintended genomic loci to a reference genome DNA sequence.

18. The method of example 17, wherein the unintended genomic loci comprise one or more of a mutation-prone site, a microsatellite locus, a sequence with sequence homology to the intended genomic locus, and/or a cancer driver.

19. The method of any one of examples 1-18, wherein the unintended genomic locus has a nucleic acid sequence that is at least partially similar to the sequence at the intended genomic locus.

20. The method of any one of examples 1-19, wherein the unintended genomic locus comprises a sequence of a tumor suppressor gene, an oncogene, a proto-oncogene, and/or a cancer driver.

21. A method for characterizing an efficiency of an engineered genomic editing event in a population of cells, wherein the engineered genomic editing event is targeted to an intended genomic locus, the method comprising:

(a) preparing a sequencing library from a sample comprising a plurality of double-stranded DNA molecules originating from the population of cells following the genomic editing event, wherein preparing the sequence library comprises ligating asymmetric adapter molecules to the plurality of double-stranded DNA molecules to generate a plurality of adapter-DNA molecules;

(b) sequencing first and second strands of the adapter-DNA molecules to provide a first strand sequence read and a second strand sequence read for at least a portion of the adapter-DNA molecules;

(c) for each sequenced adapter-DNA molecule, comparing the first strand sequence read and the second strand sequence read to identify one or more correspondences between the first and second strand sequences reads; and (d) determining a frequency of an anticipated genomic sequence at the intended genomic locus among the plurality of double-stranded DNA molecules comprising the intended genomic locus by:
analyzing the one or more correspondences between the first and second strand sequence reads; and
comparing the correspondences to the anticipated genomic sequence.

22. The method of example 21, further comprising selectively enriching one or more targeted genomic regions prior to sequencing to provide a plurality of enriched adapter-DNA molecules.

23. The method of example 22, wherein the one or more targeted genomic regions comprises the intended genomic locus in the genome.

24. The method of example 22, wherein the one or more targeted genomic regions comprises at least one unintended genomic locus in the genome.

25. The method of any one of examples 21-24, further comprising:
identifying one or more variants at unintended genomic loci by:

analyzing the one or more correspondences between first and second strand sequence reads derived from double-stranded DNA molecules comprising sequences from one or more unintended genomic loci; and comparing the correspondences to a reference genome sequence; and determining a variant frequency of the one or more variants among the plurality of double-stranded DNA molecules comprising the one or more unintended genomic loci.

26. The method of any one of examples 21-25, wherein comparing the correspondences to the anticipated genomic sequence comprises identifying an incorrect mutation in the sequence of the intended loci for genomic editing.

27. The method of any one of examples 21-25, wherein comparing the correspondences to the anticipated genomic sequence comprises identifying an unaltered sequence.

28. A method of generating high accuracy sequencing reads of a population of target double-stranded nucleic acid molecules extracted from a genome-edited cell population, the method comprising:
 (a) duplex sequencing one or more target double-stranded nucleic acid molecules extracted from the cell population; and
 (b) generating high accuracy consensus sequences for the targeted double-stranded DNA molecules,
 wherein the target double-stranded nucleic acid molecules comprise an intended genome edited region of DNA and one or more unintended genomic regions of DNA.

29. The method of example 28, wherein the unintended genomic region of DNA has a nucleic acid sequence that is at least partially similar to the intended genome edited region of DNA.

30. The method of example 28 or example 29, further comprising comparing the high accuracy consensus sequences mapping to the intended genome edited region of DNA to an anticipated genome edited DNA sequence, and wherein a targeted genome editing process is considered successful if one or more high accuracy consensus sequences mapping to the intended genome edited region is substantially the same as the anticipated genome edited DNA sequence.

31. The method of example 30, wherein the targeted genome editing process is considered successful if a majority of the high accuracy consensus sequences mapping to the intended genome edited region is substantially the same as the anticipated genome edited DNA sequence.

32. The method of any one of examples 28-31, further comprising comparing the high accuracy consensus sequences mapping to the unintended genomic regions to a reference genomic sequence derived from cells that have not undergone the genomic editing event, wherein a targeted genome editing process is considered successful if the high accuracy consensus sequences mapping to the unintended genomic regions are substantially the same as the reference genomic sequence.

33. A method for determining if DNA was successfully genome-edited at an intended genetic locus using an engineered targeted genomic editing event, the method comprising:
 a) providing duplex error-corrected sequencing reads for a plurality of double-stranded DNA molecules extracted from a sample following the engineered targeted genomic editing event; and
 b) for each genetic locus in a set of one or more genetic loci in a reference genome, quantifying the double-stranded DNA molecules for which the duplex error-corrected sequencing reads have sequences substantially the same as an expected sequence.

34. The method of example 33, wherein the set of one or more genetic loci in the reference genome comprises the intended genetic locus, and wherein the expected sequence comprises an anticipated genomic edited DNA sequence.

35. The method of example 33 or example 34, wherein the set of one or more genetic loci in the reference genome comprises an unintended genetic locus, and wherein the expected sequence comprises a genomic sequence derived from cells that have not undergone the genomic editing event.

36. The method of example 35, wherein the unintended genetic locus comprises a mutation-prone site, a microsatellite locus, a sequence with sequence homology to the intended genetic locus, and/or a cancer driver.

37. A method of assessing neoplastic potential of a cell population following an engineered genomic editing event, comprising:
 (a) preparing a sequencing library from a sample comprising double-stranded DNA molecules originating from the cell population following the engineered genomic editing event, wherein preparing the sequence library comprises tagging a plurality of double-stranded DNA molecules to generate a plurality of tagged DNA molecules having first and second tagged strands;
 (b) selectively enriching the first and second tagged strands for a subset of tagged DNA molecules that map to one or more cancer drivers to provide enriched tagged DNA molecules;
 (c) generating an error-corrected sequence read for each of a plurality of enriched tagged DNA molecules, wherein the generating the error-corrected sequence reads comprises:
  sequencing one or more first and second tagged strands derived from the enriched tagged DNA molecules to provide a first strand sequence and a second strand sequence;
  comparing the first strand sequence and the second strand sequence to identify one or more correspondences between the first and second strand sequences; and
 (d) determining if there is a variant present in the one or more cancer drivers among the plurality of enriched tagged DNA molecules by comparing the one or more correspondences to a reference genome sequence.

38. The method of example 37, wherein the one or more variants comprise a functionally disruptive mutation.

39. The method of example 37 or example 38, wherein the one or more cancer drivers is or comprises ABL, ACC, BCR, BLCA, BRCA, CESC, CHOL, COAD, DLBC, DNMT3A, EGFR, ESCA, GBM, HNSC, RICH, KIRC, KIRP, LAML, LGG, LIHC, LUAD, LUSC, MESO, OV, PAAD, PCPG, PI3K, PIK3CA, BRAD, PTEN READ, SARC, SKCM, STAD, TGCT, THCA, UCEC, UCS, and/or UVM.

40. The method of example 37 or example 38, wherein the cancer driver is or comprises TP53.

41. The method of example 37 or example 38, wherein the cancer driver is or comprises HRAS, NRAS or KRAS.
42. The method of any one of examples 37-41, wherein if there is a variant present in one or more cancer drivers among the plurality of enriched tagged DNA molecules, then the method further comprises (e) determining a variant frequency of the variant among the plurality of enriched tagged DNA molecules.
43. The method of example 42, wherein the method steps (a) to (e) are performed at a first time point after the event and at a second time point after the event, wherein the second time point is after the first time point, and wherein the variant frequency from the first time point is compared to the variant frequency from the second time point.
44. The method of example 43, wherein the second time point is 2 to 90 days after the first time point.
45. The method of example 43, wherein both the first and second time points are within about 30 days, within about 45 days, within about 60 days, within about 75 days, or within about 90 days following the engineered genomic editing event.
46. The method of any one of examples 43-45, wherein the cell population is determined to have neoplastic potential if the variant frequency from the second time point is greater than the variant frequency from the first time point.
47. The method of example 42, wherein the method steps (a) to (e) are performed within about 30 days following the engineered genomic editing event, and wherein the variant frequency is compared to a pre-event variant frequency determined from a comparable cell population that has not undergone the engineered genomic editing event.
48. A method for detecting and/or quantifying clonal expansion of a cell in a cell population following an engineered genomic editing event, comprising:
    (a) duplex sequencing one or more target double-stranded DNA molecules originating from a cell population following the engineered genomic editing event;
    (b) identifying one or more variants among the target double-stranded DNA molecules;
    (c) determining a variant frequency of the one or more variants among the target double-stranded DNA molecules originating from the cell population; and
    (d) comparing the variant frequency for each of the one or more variants to an expected variant frequency.
49. The method of example 48, wherein the step of duplex sequencing comprises:
    (i) preparing a sequencing library from double-stranded DNA molecules originating from the cell population following the engineered genomic editing event, wherein preparing the sequence library comprises ligating adapter molecules to the plurality of double-stranded DNA fragments to generate a plurality of adapter-DNA molecules;
    (ii) sequencing first and second strands of the adapter-DNA molecules to provide a first strand sequence read and a second strand sequence read for each adapter-DNA molecule; and
    (iii) for each adapter-DNA molecule, comparing the first strand sequence read and the second strand sequence read to identify one or more correspondences between the first and second strand sequences reads.
50. The method of example 48 or example 49, wherein the variant frequency of the one or more variants is determined by calculating a number of duplex sequenced target double-stranded DNA molecules having a specified variant mapping to a genomic locus of interest per total number of duplex sequenced target double-stranded DNA molecules mapping to the genomic locus of interest.
51. The method of any one of examples 48-50, wherein the variant frequency of one or more variants is above a threshold variant frequency.
52. The method of any one of examples 48-51, wherein the one or more variants are identified relative to a sequence from a reference cell population.
53. The method of any one of examples 48-52, wherein the method steps (a) to (c) are performed at a first time point after the event and at a second time point after the event, wherein the second time point is after the first time point, and wherein the variant frequency from the first time point is the expected variant frequency.
54. The method of example 53, wherein the second time point is 2 to 90 days after the first time point.
55. The method of example 53, wherein both the first and second time points are within about 30 days, within about 45 days, within about 60 days, within about 75 days, or within about 90 days following the engineered genomic editing event.
56. The method of any one of examples 53-55, wherein clonal expansion of a cell in the cell population is determined to have occurred if the variant frequency from the second time point is greater than the variant frequency from the first time point.
57. The method of any one of examples 48-56, wherein clonal expansion of a cell in the cell population is determined to have occurred if the variant frequency is greater than the expected variant frequency.
58. The method of example 56 or example 57, wherein the clonal expansion of the cell indicates an abnormal cell proliferative sate, a cancer-like state, a pre-cancerous state or a field effect.
59. The method of example 48, wherein the expected variant frequency is determined from a comparable cell population that has not undergone the engineered genomic editing event.
60. The method of any one of examples 48-59, wherein the one or more variants are at one or more locations outside an intended locus for genomic editing.
61. The method of any one of examples 48-60, wherein the one or more variants are in a sequence of a tumor suppressor gene, an oncogene, a proto-oncogene, and/or a cancer driver.
62. The method of any one of examples 48-61, wherein the one or more variants comprise a functionally disruptive mutation.
63. The method of any one of examples 48-62, wherein at least one variant is in TP53.
64. The method of any one of examples 47-63, wherein at least one variant is in HRAS, NBAS or KRAS.
65. The method of any one of examples 48-64, wherein at least one variant is a passenger mutation.
66. The method of any one of examples 48-65, wherein at least one variant is a non-cancer driver variant.
67. The method of any one of examples 1-66, wherein the population of cells or cell population are or comprise pluripotent stem cells, embryonic stem cells, immune cells, or plant cells.

68. The method of any one of examples 1-67, wherein the population of cells or cell population is derived from a human patient.
69. The method of example 68, wherein the double-stranded DNA molecules obtained from the human patient is obtained from tissue, from circulating cells, from cell-free DNA in plasma, from cell-free DNA in other bodily fluids, from exosomal DNA, from cells shed by a tissue, and/or from a biopsy.
70. The method of any one of examples 1-68, wherein the population of cells or cell population is grown in a cell culture.
71. The method of any one of examples 1-68 and 70, wherein the population of cells or cell population is derived from a human or animal subject.
72. The method of any one of examples 1-71, wherein the population of cells or cell population is derived from a xenograft.
73. The method of any one of examples 1-72, wherein the engineered genomic editing event is a target endonuclease-mediated editing event.
74. The method of any one of examples 1-73, wherein the engineered genomic editing event is a Cas9-mediated editing event.
75. The method of any one of examples 1-73, wherein the engineered genomic editing event is a CPF1-mediated editing event.
76. The method of any one of examples 1-73, wherein the engineered genomic editing event is a modified CAS or CPF-1 mediated event.
77. The method of any one of examples 1-73, wherein the engineered genomic editing event is carried out by a TALON, MEGATAL, Zinc-fingered nuclease, a homing endonuclease, or a restriction endonuclease.
78. The method of any one of examples 1-73, wherein the engineered genomic editing event is a polynucleotide substrate-mediated homologous recombination event.
79. The method of any one examples 1-73, wherein the engineered genomic editing event is carried out by a retrovirus or another virus.
80. The method of any one of examples 1-73, wherein the engineered genomic editing event introduces one or more of a DNA break, a DNA adduct, a site of DNA oxidative damage, a DNA nick, or a site of DNA deamination.
81. The method of any one of examples 1-72, wherein the population of cells or the cell population was edited using a CRISPR/Cas9 system.
82. The method of any one of examples 11, 25, 42 and 48, wherein the variant frequency of one or more variants is greater than a background variant frequency of a reference population of double-stranded DNA molecules extracted from a reference population of cells that have not undergone an engineered genomic editing event.
83. The method of any one of examples 1-82, wherein the engineered genomic editing event results in the death or damage of a subset of cells in the population of cells or cell population.
84. The method of any one of examples 1-82, wherein a subset of cells in the population of cells or cell population has one or more pre-existing genetic mutations, and wherein following the engineered genomic editing event, the subset of cells selectively proliferate at a greater rate than other cells in the population of cells or cell population.
85. The method of any one of examples 1-82, wherein a subset of cells in the population of cells or cell population has a pre-existing epigenetic state unique to said cells, and wherein following the engineered genomic editing event, the subset of cells selectively proliferate at a greater rate than other cells in the population of cells or cell population.
86. The method of any one of examples 1-85, wherein the engineered genomic editing event causes mutations to DNA.
87. The method of any one of examples 1-86, wherein the engineered genomic editing event repairs a mutation in the genomic DNA.
88. A method for monitoring neoplastic potential of a cell population following an engineered genomic editing event, comprising:
 (a) duplex sequencing one or more target double-stranded DNA molecules originating from a cell population following the engineered genomic editing event at a first time point;
 (b) identifying one or more variants among the target double-stranded DNA molecules;
 (c) determining a variant frequency of the one or more variants among the target double-stranded DNA molecules originating from the cell population at the first time point;
 (d) duplex sequencing one or more target double-stranded DNA molecules originating from a cell population following the engineered genomic editing event at a second time point;
 (e) determining a variant frequency of the same one or more variants among the target double-stranded DNA molecules originating from the cell population at a second time point; and
 (f) comparing the variant frequency for each of the one or more variants from the first time point to the variant frequency for each of the one or more variants from the second time point.
89. The method of example 88, wherein the steps of duplex sequencing each comprise:
 (i) preparing a sequencing library from double-stranded DNA molecules originating from the cell population, wherein preparing the sequence library comprises ligating adapter molecules to the plurality of double-stranded DNA fragments to generate a plurality of adapter-DNA molecules;
 (ii) sequencing first and second strands of the adapter-DNA molecules to provide a first strand sequence read and a second strand sequence read for each adapter-DNA molecule; and
 (iii) for each adapter-DNA molecule, comparing the first strand sequence read and the second strand sequence read to identify one or more correspondences between the first and second strand sequences reads.
90. The method of example 88 or example 89, wherein the population of genome edited cells are or comprise genome-edited immune cells.
91. The method of any one of examples 88-90, wherein the population of genome edited cells are administered to a subject between the first and second time point.
92. The method of example 91, wherein clonal expansion of a cell in the cell population is determined to have occurred if the variant frequency from the second time point is greater than the variant frequency from the first time point.

93. The method of example 92, wherein the one or more variants are in a sequence of a tumor suppressor gene, an oncogene, a proto-oncogene, and/or a cancer driver.

94. The method of example 92, wherein the one or more variants comprise a functionally disruptive mutation.

95. The method of any one of examples 92-94, wherein at least one variant is in TP53.

96. The method of any one of examples 92-95, wherein at least one variant is in HRAS, NRAS or KRAS.

97. The method of any one of examples 92-96, wherein at least one variant is a passenger mutation.

98. The method of any one of examples 92-97, wherein at least one variant is a non-cancer driver variant.

99. A kit able to be used in error corrected duplex sequencing of double stranded polynucleotides to characterize a population of cells following an engineered genomic editing event, the kit comprising:
at least one set of polymerase chain reaction (PCR) primers and at least one set of adaptor molecules, wherein the primers and adaptor molecules are able to be used in error corrected duplex sequencing experiments; and
instructions on methods of use of the kit in conducting error corrected duplex sequencing of DNA extracted from a sample derived from the population of cells to identify one or more of:
an anticipated genomic sequence at an intended genomic locus;
a variant at an unintended genomic locus;
a mutation in a cancer driver; and
a variant frequency of one or more variants.

100. The kit of example 99, wherein the reagent comprises a DNA repair enzyme.

101. The kit of example 99, wherein each of the adapter molecules in the set of adaptor molecules comprises at least one single molecule identifier (SMI) sequence and at least one strand defining element.

102. The kit of example 99, further comprises a computer program product embodied in a non-transitory computer readable medium that, when executed on a computer, performs steps of determining an error-corrected duplex sequencing read for one or more double-stranded DNA molecules in a sample, and determining a sequence at the intended genomic locus, a sequence at one or more unintended genomic loci, a variant, a variant frequency, and/or a genome edited spectrum following the genomic editing event using the error-corrected duplex sequencing read.

103. A system for characterizing a population of cells following an engineered genomic editing event and/or detecting clonal expansion of a cell within the population of cells, comprising:
a computer network for transmitting information relating to sequencing data and genome editing data, wherein the information includes one or more of raw sequencing data, duplex sequencing data, sample information, and genome editing information;
a client computer associated with one or more user computing devices and in communication with the computer network;
a database connected to the computer network for storing a plurality of genome editing profiles and user results records;
a duplex sequencing module in communication with the computer network and configured to receive raw sequencing data and requests from the client computer for generating duplex sequencing data, group sequence reads from families representing an original double-stranded nucleic acid molecule and compare representative sequences from individual strands to each other to generate duplex sequencing data; and
a genome editing module in communication with the computer network and configured to compare duplex sequencing data to reference sequence information to identify variants and generate genome editing data comprising at least one of a genomic alteration at an intended and/or unintended genomic locus.

104. The system of example 103, wherein the genome editing profiles comprise sequence information from one or more intended genomic loci.

105. The system of example 103, wherein the genome editing profiles comprise sequence information from one or more unintended genomic loci.

106. The system of example 103, wherein the genome editing profiles comprise a variant frequency for one or more variants in the genome of the populations of cells.

107. A non-transitory computer-readable storage medium comprising instructions that, when executed by one or more processors, performs a method of any one of examples 1-98 for characterizing a population of cells following an engineered genomic editing event and/or detecting clonal expansion of a cell within the population of cells.

108. A computer system for performing a method of any one of examples 1-98 for characterizing a population of cells following an engineered genomic editing event and/or detecting clonal expansion of a cell within the population of cells, the system comprising: at least one computer with a processor, memory, database, and a non-transitory computer readable storage medium comprising instructions for the processor(s), wherein said processor(s) are configured to execute said instructions to perform operations comprising the methods of any one of examples 1-98.

109. The system of example 108, further comprising a networked computer system comprising:
a. a wired or wireless network;
b. a plurality of user electronic computing devices able to receive data derived from use of a kit comprising reagents to extract, amplify, and produce a polynucleotide sequence of a sample, and to transmit the polynucleotide sequence via a network to a remote server; and
c. a remote server comprising the processor, memory, database, and the non-transitory computer readable storage medium comprising instructions for the processor(s), wherein said processor(s) are configured to execute said instructions to perform operations comprising the methods of any one of examples 1-98; and
d. wherein said remote server is able to detect and identify variants and/or clonal expansion events resulting from the genomic editing event.

110. The system of example 109, wherein the database and/or a third-party database accessible via the network, further comprises a plurality of records comprising one or more of a genome editing profile of a population of cells, a reference sequence, an anticipated genome edited sequence, and a variant frequency at one or more time points.

111. A non-transitory computer-readable medium whose contents cause at least one computer to perform a method for providing duplex sequencing data for double-stranded nucleic acid molecules in a sample from a genome edited cell population, the method comprising:
  receiving raw sequence data from a user computing device; and
  creating a sample-specific data set comprising a plurality of raw sequence reads derived from a plurality of nucleic acid molecules in the sample;
  grouping sequence reads from families representing an original double-stranded nucleic acid molecule, wherein the grouping is based on a shared single molecule identifier sequence;
  comparing a first strand sequence read and a second strand sequence read from an original double-stranded nucleic acid molecule to identify one or more correspondences between the first and second strand sequences reads; and
  providing duplex sequencing data for the double-stranded nucleic acid molecules in the sample.

112. The computer-readable medium of example 111, further comprising identifying nucleotide positions of non-complementarity between the compared first and second sequence reads, wherein the method further comprises in positions of non-complementarity, identifying and eliminating or discounting process errors.

113. A non-transitory computer-readable medium whose contents cause at least one computer to perform a method detecting and identifying edited sequences at intended genomic loci resulting from a genomic editing event in a cell population, the method comprising:
  comparing duplex sequence data comprising a plurality of subject sequences to reference sequence information;
  identifying sequence correspondences and/or variations in the duplex sequence data, wherein a variation is identified as a region of non-agreement with the reference information at the intended genomic loci;
  determining a frequency of anticipated genome edited sequences among the plurality of subject sequences in the duplex sequence data;
  generating a genome edited spectrum from the duplex sequence data; and
  providing genome editing data.

114. A non-transitory computer-readable medium whose contents cause at least one computer to perform a method for detecting and identifying edited sequences at unintended genomic loci resulting from a genomic editing event in a cell population, the method comprising:
  comparing duplex sequence data comprising a plurality of subject sequences to reference sequence information;
  identifying sequence correspondences and/or variations in the duplex sequence data, wherein a variation is identified as a region of non-agreement with the reference information at the unintended genomic loci;
  determining if a subject sequence comprises a variant at an unintended genomic locus;
  if a variant is present, determining a variant frequency of the variant within the duplex sequence data;
  generating a genome edited spectrum from the duplex sequence data; and
  providing genome editing data.

115. A non-transitory computer-readable medium whose contents cause at least one computer to perform a method for detecting and identifying clonal expansion of a cell in a cell population following a genomic editing event, the method comprising:
  identifying sequence variants in a target genomic region using duplex sequencing data generated from a sample originating from the genome edited cell population;
  calculating a variant allele frequency (VAF) of a test sample and a control sample;
  determining if a VAF is higher in a test group than in a control group;
  in samples having a higher VAF, determining if a sequence variant is a non-singlet;
  in samples having a higher VAF, determining if the sequence variant is a driver mutation; and
  characterizing samples having a non-singlet and/or a driver mutation as being suspicious for of undergoing clonal expansion.

116. A non-transitory computer-readable medium of example 115, further comprising assessing a safety threshold for the genome edited cell population and/or determining a risk associated with treating a subject with the genome edited cell population.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for monitoring neoplastic potential of a cell population following an engineered genomic editing event, comprising:
   (a) duplex sequencing one or more target double-stranded DNA molecules originating from the cell population following the engineered genomic editing event at a first time point;
   (b) identifying one or more variants among the target double-stranded DNA molecules;
   (c) determining a first variant frequency of the one or more variants among the target double-stranded DNA molecules originating from the cell population at the first time point;
   (d) duplex sequencing one or more target double-stranded DNA molecules originating from the cell population following the engineered genomic editing event at a second time point following the first time point;
   (e) determining a second variant frequency of the same one or more variants among the target double-stranded DNA molecules originating from the cell population at the second time point; and
   (f) comparing the first variant frequency for the one or more variants to the second variant frequency for the one or more variants.

2. The method of claim 1, wherein the step of duplex sequencing comprises:
   (i) preparing a sequencing library from double-stranded DNA molecules originating from the cell population, wherein preparing the sequence library comprises ligating adapter molecules to the plurality of double-stranded DNA fragments to generate a plurality of adapter-DNA molecules;
   for at least some of the plurality of adapter-DNA molecules:
   (ii) sequencing first and second strands of the adapter-DNA molecules to provide a first strand sequence read and a second strand sequence read for the adapter-DNA molecules; and
   (iii) for the adapter-DNA molecules, comparing the first strand sequence read and the second strand sequence read to identify one or more correspondences between the first and second strand sequences reads.

3. The method of claim 1, wherein the cell population comprises genome-edited immune cells.

4. The method of claim 1, wherein the cell population is administered to a subject between the first and second time points.

5. The method of claim 1, wherein the engineered genomic editing event is a target endonuclease-mediated editing event; is a Cas-mediated editing event; is a Cas9-mediated editing event; is a CPF1-mediated editing event; is a modified CAS or CPF-1 mediated event; is carried out by a TALON, MEGATAL, Zinc-fingered nuclease, a homing endonuclease, or a restriction endonuclease; is a polynucleotide substrate-mediated homologous recombination event; is carried out by a retrovirus or another virus; or any combination of one or more of the foregoing.

6. The method of claim 1, wherein the second variant frequency for the one or more variants is a safe threshold variant frequency.

7. The method of claim 1, wherein following step (f), the method further comprises identifying a variant from the one or more variants identified in step (b) as a variant with a positive growth bias.

8. The method of claim 1, wherein the cell population is a cell-based therapy.

9. The method of claim 1, wherein the one or more variants identified in step (b) comprise a cell-cycle mutation.

10. The method of claim 1, wherein the one or more variants identified in step (b) are detected in one or more cancer drivers.

11. The method of claim 10, wherein the one or more cancer drivers comprises ABL, ACC, BCR, BLCA, BRCA, CESC, CHOL, COAD, DLBC, DNMT3A, EGFR, ESCA, GBM, HNSC, RICH, KIRC, KIRP, LAML, LGG, LIHC, LUAD, LUSC, MESO, OV, PAAD, PCPG, PI3K, PIK3CA, BRAD, PTEN READ, SARC, SKCM, STAD, TGCT, THCA, THUM, UCEC, UCS, and/or UVM.

12. The method of claim 10, wherein the cancer driver comprises TP53.

13. The method of claim 10, wherein the cancer driver comprises HRAS, NRAS or KRAS.

14. The method of claim 1, wherein the one more variants are in a sequence of a tumor suppressor gene, an oncogene, and/or a proto-oncogene.

15. The method of claim 1, wherein the cell population is determined to have neoplastic potential if the second variant frequency is greater than the first variant frequency.

16. The method of claim 1, wherein the first and/or second variant frequency of the one or more variants is above a threshold variant frequency.

17. The method of claim 1, wherein the one or more variants are identified relative to a sequence from a reference cell population.

18. The method of claim 1, wherein both the first and second time points are within about 30 days, within about 45 days, within about 60 days, within about 75 days, or within about 90 days following the engineered genomic editing event.

19. The method of claim 1, wherein the second time point is 2 to about 90 days after the first time point.

20. The method of claim 1, wherein a clonal expansion of a cell in the cell population is determined to have occurred if the second variant frequency is greater than the first variant frequency.

21. The method of claim 1, further comprising comparing the first variant frequency and/or the second variant frequency for the one or more variants to an expected variant frequency.

22. The method of claim 21, wherein the expected variant frequency is determined from a comparable cell population that has not undergone the engineered genomic editing event.

23. The method of claim 21, wherein the cell population is determined to have neoplastic potential if the first and/or second variant frequency is greater than the expected variant frequency.

24. The method of claim 1, wherein the one or more variants are at one or more locations outside an intended locus for genomic editing.

25. The method of claim 1, wherein the variant frequency of the one or more variants is determined by calculating a number of duplex sequenced target double-stranded DNA molecules having a specified variant mapping to a genomic locus of interest per a total number of duplex sequenced target double-stranded DNA molecules mapping to the genomic locus of interest.

26. The method of claim 2, wherein prior to sequencing, the method further comprises selectively enriching the first and second strands for a subset of adapter-DNA molecules that map to one or more genomic loci of interest to provide an enriched sequencing library.

\* \* \* \* \*